(12) United States Patent
Chen et al.

(10) Patent No.: US 9,512,473 B2
(45) Date of Patent: Dec. 6, 2016

(54) METHODS, COMPOSITIONS, AND KITS FOR DETECTING ALLELIC VARIANTS

(71) Applicant: LIFE TECHNOLOGIES CORPORATION, Carlsbad, CA (US)

(72) Inventors: Caifu Chen, Palo Alto, CA (US); Ruoying Tan, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 102 days.

(21) Appl. No.: 14/445,046

(22) Filed: Jul. 28, 2014

(65) Prior Publication Data

US 2015/0140557 A1    May 21, 2015

Related U.S. Application Data

(63) Continuation of application No. 12/748,329, filed on Mar. 26, 2010, now abandoned, which is a continuation-in-part of application No. 12/641,321, filed on Dec. 17, 2009.

(60) Provisional application No. 61/258,582, filed on Nov. 5, 2009, provisional application No. 61/253,501, filed on Oct. 20, 2009, provisional application No. 61/251,623, filed on Oct. 14, 2009, provisional application No. 61/186,775, filed on Jun. 12, 2009, provisional application No. 61/164,230, filed on Mar. 27, 2009, provisional application No. 61/138,521, filed on Dec. 17, 2008.

(51) Int. Cl.
*C12Q 1/68* (2006.01)

(52) U.S. Cl.
CPC .............. *C12Q 1/6858* (2013.01); *C12Q 1/686* (2013.01); *C12Q 1/6883* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,419,966 A | 5/1995 | Reed et al. |
| 5,512,441 A | 4/1996 | Ronai |
| 5,512,677 A | 4/1996 | Chern et al. |
| 5,538,848 A | 7/1996 | Livak et al. |
| 5,585,481 A | 12/1996 | Arnold, Jr. et al. |
| 5,696,251 A | 12/1997 | Arnold, Jr. et al. |
| 5,736,626 A | 4/1998 | Mullah et al. |
| 5,801,155 A | 9/1998 | Kutyavin et al. |
| 5,891,625 A | 4/1999 | Buchardt et al. |
| 5,925,517 A | 7/1999 | Tyagi et al. |
| 5,928,907 A | 7/1999 | Woudenberg et al. |
| 5,942,610 A | 8/1999 | Nelson et al. |
| 5,972,601 A | 10/1999 | Buchardt et al. |
| 6,015,674 A | 1/2000 | Woudenberg et al. |
| 6,027,889 A | 2/2000 | Barany et al. |
| 6,030,813 A | 2/2000 | Ellis et al. |
| 6,084,102 A | 7/2000 | Kutyavin et al. |
| 6,103,476 A | 8/2000 | Tyagi et al. |
| 6,150,097 A | 11/2000 | Tyagi et al. |
| 6,174,670 B1 | 1/2001 | Wittwer et al. |
| 6,245,533 B1 | 6/2001 | Goldstein et al. |
| 6,303,305 B1 | 10/2001 | Wittwer et al. |
| 6,355,421 B1 | 3/2002 | Coull et al. |
| 6,383,752 B1 | 5/2002 | Agrawal et al. |
| 6,391,592 B1 | 5/2002 | Su et al. |
| 6,485,901 B1 | 11/2002 | Gildea et al. |
| 6,492,346 B1 | 12/2002 | Hedgpeth et al. |
| 6,503,720 B2 | 1/2003 | Wittwer et al. |
| 6,548,250 B1 | 4/2003 | Sorge et al. |
| 6,589,250 B2 | 7/2003 | Schendel |
| 6,589,743 B2 | 7/2003 | Sorge et al. |
| 6,590,091 B2 | 7/2003 | Albagli et al. |
| 6,593,091 B2 | 7/2003 | Keys et al. |
| 6,596,490 B2 | 7/2003 | Dattagupta |
| 6,605,451 B1 | 8/2003 | Marmaro et al. |
| 6,727,356 B1 | 4/2004 | Reed et al. |
| 6,783,934 B1 | 8/2004 | McMillan et al. |
| 6,814,934 B1 | 11/2004 | Higuchi et al. |
| 6,818,420 B2 | 11/2004 | Chou et al. |
| 6,852,487 B1 | 2/2005 | Barany et al. |

(Continued)

FOREIGN PATENT DOCUMENTS

| | | |
|---|---|---|
| EP | 1905842 | 4/2008 |
| JP | 2004-511215 | 4/2004 |

(Continued)

OTHER PUBLICATIONS

Bio-Rad, "PCR Tips", Real Time PCR, 1999, pp. 94-99 (no translation).
Kerkel, K., et al., "Genomic Surveys by methylation-sensitive SNP analysis identify sequence-dependent allele-specific DNA methylation," Nature Genetics, vol. 40 (7), 2008, pp. 904-908.
Stanley, et al., "TaqMan PreAmp Master Mix Kit for Real-Time Gene Expression Analysis with Sample Limited Specimens,", Jun. 11, 2006, http://www.gene-quantification.com/stanley-AB-2006.pdf).
Zhang, Y., et al., "Imprinting of Human H19: Allele-specific CpG Methylation, Loss of the Active Allele in Wilms Tumor, and Potential for Somatic Allele Switching," Am. J. Hum. Genet., vol. 53, 1993, pp. 113-124.
Afonina et al., "Sequence-specific arrest of primer extension on single-stranded DNA by an oligonucleotide-minor groove binder conjugate", *Proceedings of the National Academy of Sciences*, vol. 93, Apr. 1996, 3199-3204.

(Continued)

*Primary Examiner* — David Thomas

(57) ABSTRACT

In some embodiments, the present inventions relates generally to compositions, methods and kits for use in discriminating sequence variation between different alleles. More specifically, in some embodiments, the present invention provides for compositions, methods and kits for quantitating rare (e.g., mutant) allelic variants, such as SNPs, or nucleotide (NT) insertions or deletions, in samples comprising abundant (e.g., wild type) allelic variants with high specificity and selectivity. In particular, in some embodiments, the invention relates to a highly selective method for mutation detection referred to as competitive allele-specific TaqMan PCR ("cast-PCR").

21 Claims, 35 Drawing Sheets

(56) References Cited

U.S. PATENT DOCUMENTS

| | | |
|---|---|---|
| 7,160,997 B2 | 1/2007 | Chou et al. |
| 7,228,237 B2 | 6/2007 | Woo et al. |
| 7,556,923 B1 | 7/2009 | Hedgpeth et al. |
| 2002/0076767 A1 | 6/2002 | Su et al. |
| 2003/0082549 A1 | 5/2003 | Liu |
| 2003/0082600 A1 | 5/2003 | Olek et al. |
| 2004/0096819 A1 | 5/2004 | McMillan et al. |
| 2005/0118623 A1 | 6/2005 | Belousov et al. |
| 2005/0287553 A1 | 12/2005 | Guetig et al. |
| 2007/0087360 A1 | 4/2007 | Boyd |
| 2007/0184457 A1 | 8/2007 | Pont-Kingdon et al. |
| 2008/0090239 A1 | 4/2008 | Shoemaker et al. |
| 2008/0286778 A1 | 11/2008 | Lewin et al. |
| 2008/0286787 A1 | 11/2008 | Campan et al. |
| 2009/0048427 A1 | 2/2009 | Hedgpeth et al. |
| 2009/0053719 A1 | 2/2009 | Lo et al. |
| 2009/0054630 A1 | 2/2009 | Burns et al. |
| 2010/0009355 A1 | 1/2010 | Kolodney |
| 2010/0221717 A1 | 9/2010 | Chen et al. |
| 2010/0285478 A1 | 11/2010 | Chen et al. |
| 2011/0287424 A1 | 11/2011 | Chen |
| 2012/0214160 A1 | 8/2012 | Deng et al. |

FOREIGN PATENT DOCUMENTS

| | | |
|---|---|---|
| JP | 20044511215 | 4/2004 |
| JP | 2005-511096 | 4/2005 |
| JP | 2006-508662 | 3/2006 |
| JP | 20066508662 | 3/2006 |
| WO | WO-90/14353 | 11/1990 |
| WO | WO-99/21881 | 5/1999 |
| WO | WO-03/050305 | 6/2003 |
| WO | WO-2007/044091 | 4/2007 |
| WO | WO-2007/106534 | 9/2007 |
| WO | WO-2008/104794 | 9/2008 |
| WO | WO-2010/014920 | 2/2010 |
| WO | WO-2010/077324 | 7/2010 |
| WO | WO-2010/080559 | 7/2010 |
| WO | WO-2010/111682 | 9/2010 |
| WO | WO-2011/139920 | 11/2011 |
| WO | WO-2011/150075 | 12/2011 |
| WO | WO-2012/001007 | 1/2012 |
| WO | WO-2012/097353 | 7/2012 |
| WO | WO-2012/151560 | 11/2012 |
| WO | WO-2014/004726 | 1/2014 |

OTHER PUBLICATIONS

Aoyagi, "PCR", *Molecular Biology Problem Solver: A Laboratory Guide*, 2001, 291-329.

Applied Biosystems, "TaqMan PreAmp Master Mix Kit Protocol", downloaded from URL:hhtp://www3.appliedbiosystems.com/cms/groups/mcb_support/documents/generaldocuments/cms_039316.pdf, Jul. 2010, 33 pages.

Ayyadevara et al., "Discrimination of Primer 3'-Nucleotide Mismatch by Taq DNA Polymerase during Polymerase Chain Reaction", *Analytical Biochemistry*, vol. 284, Issue 1, Aug. 15, 2000, 11-18.

Ballantyne et al., "Locked nucleic acids in PCR primers increase sensitivity and performance", *Genomics*, vol. 91, No. 3, Mar. 2008, 301-305.

Beattie, "PCR Optimization Kit", *MP Biomedicals*, Catalog No. 824000, Mar. 19, 1998, 1-9.

Benner et al., "Evolution, language and analogy in functional genomics.", *Trends in Genetics*, vol. 17, No. 7, Jul. 1, 2001, 414-418.

Blons et al., "181 Accuracy of castPCR-based KRAS testing on paraffin embedded tissues", *European Journal of Cancer Supplements*, vol. 8, No. 5, Jun. 2010, 47-48.

Brock et al., "*Thermus aquaticus* gen. n. and sp. n., a Nonsporulating Extreme Thermophile", Journal of Bacteriology, vol. 1, No. 1, 1969, 289-297.

Broude et al., "Stem-loop oligonucleotides: a robust tool for molecular biology and biotechnology", *Trends in Biotechnology*, vol. 20, No. 6, Jun. 2002, 249-256.

Bustin et al.,"The MIQE: Minimum Information for Publication of Quantative Real-Time PCT Expirements", *Clinical Chemistry*, vol. 55, No. 4, Apr. 2009, 611-622.

Cantera et al., "Evolutionary relationship of phototrophic bacteria in the α-Proteobacteria based on farnesyl diphosphate synthase", *Microbiology*, vol. 148, No. 6, Jun. 2002, 1923-1929.

Chen et al., "Single nucleotide polymorphism genotyping: biochemistry, protocol, cost and throughput", *Pharmacogenomics Journal*, vol. 3, No. 2, 2003, 77-96.

Coen et al., "The Polymerase Chain Reaction", *Current Protocols in Molecular Biology*, Chs. 15, 15.0.1-15.1.14; Suppls. 88 and 56, 2009, 1-7.

Cottrell et al., "A real-time PCR assay for DNA-methylation using methylation-specific blockers", *Nucleic Acids Research*, vol. 32, No. 1, Jan. 13, 2004, e10 (1-8).

Dharmasiri et al., "Microsystems for the Capture of Low-Abundance Cells", *Annual Review of Analytical Chemistry*, vol. 3, No. 1, Jul. 2010, 409-431.

Diercks et al., "Resolving Cell Population Heterogeneity: Real-Time PCR for Simultaneous Multiplexed Gene Detection in Multiple Single-Cell Samples", *PLoS One*, vol. 4, No. 7, Jul. 27, 2009, 1-9.

EP Application No. 09836510.9, Supplementary EP Search Report mailed Jan. 2, 2013, 1-7.

EP Application No. 10756973.3, Extended European Search Report mailed Jan. 2, 2013, 1-8.

Gineikiene et al., "Single Nucleotide Polymorphism-Based System Improves the Applicability of Quantitative PCR for Chimerism Monitoring", *The Journal of Molecular Diagnostics*, vol. 11, No. 1, Jan. 2009, 66-74.

Gormally, "Circulating free DNA in plasma or serum as biomarker of carcinogenesis: Practical aspects and biological significance", *Mutation Research*, vol. 635, Nos. 2-3, Jan. 25, 2007, 105-117.

Gray-Schopfer et al., "The role of B-RAF in melanoma", *Cancer and Metastasis Reviews*, vol. 24, No. 1, Jan. 2005, 165-183.

Hecker et al., "High and Low Annealing Temperatures Increase Both Specificity and Yield in Touchdown and Stepdown PCR", *BioTechniques*, vol. 20, No. 3, Mar. 1996, 478-485.

Henegariu et al., "Multiplex Pcr: Critical Parameters and Step-By-Step Protocol", *Biotechniques*, vol. 23, No. 3, Sep. 1997, 504-511.

Hiratsuka et al., "Competitive allele-specific short oligonucleotide hybridization (CASSOH) with enzyme-linked immunosorbent assay (ELISA) for the detection of pharmacogenetic single nucleotide polymorphisms (SNPs)", *Journal of Biochemical and Biophysical Methods*, vol. 67, Nos. 2-3, Jun. 30, 2006, 87-94.

Huang et al., "Fluorescence Characteristics of Site-Specific and Stereochemically Distinct Benzo[a]pyrene Diol Epoxide-DNA Adducts as Probes of Adduct Conformation", *Chemical Research in Toxicology*, vol. 15, No. 2, Feb. 2002, 118-126.

Imyanitov et al., "Improved Reliability of Allele-specific PCR", *BioTechniques*, vol. 33, No. 3, Sep. 2002, 484-490.

Integrated DNA Technologies, "Modified Bases Catalog Page", downloaded from URL: http://www.idtdna.com/Catalog/Modifications/Modifications.aspx?catid=7, Mar. 13, 2006.

Intl Application No. PCT/US2009/006652, International Preliminary Report on Patentability mailed Jun. 30, 2011, 1-5.

Intl Application No. PCT/US2009/006652, International Search Report and Written Opinion mailed Aug. 31, 2010, 1-9.

Intl Application No. PCT/US2009/068610, International Preliminary Report on Patentability mailed Jun. 30, 2011, 1-5.

Intl Application No. PCT/US2009/068610, International Search Report and Written Opinion mailed Aug. 31, 2010, 1-9.

Intl Application No. PCT/US2010/028963, International Preliminary Report on Patentability mailed Oct. 6, 2011, 1-6.

Intl Application No. PCT/US2010/028963, International Search Report mailed Jan. 20, 2011, 1-9.

Intl Application No. PCT/US2011/034675, International Preliminary Report on Patentability mailed Nov. 8, 2012, 1-6.

Intl Application No. PCT/US2011/034675, International Search Report and the Written Opinion mailed Feb. 8, 2012, 1-7.

(56) References Cited

OTHER PUBLICATIONS

Intl Application No. PCT/US2012/021397, International Preliminary Report on Patentability mailed Jul. 16, 2013, 1-7.

Intl Application No. PCT/US2012/021397, International Search Report and the Written Opinion mailed Jun. 22, 2012, 1-10.

Intl Application No. PCT/US2013/047984, International Search Report and Written Opinion mailed Aug. 23, 2013, 1-11.

Isacsson et al., "Rapid and specific detection of PCR products using light-up probes", *Molecular Cell Probes*, vol. 14, No. 5, Oct. 2000, 321-328.

Itabashi et al., "Quantitative detection of mutant alleles of the K-ras gene with minor groove binder-conjugated fluorogenic DNA probes", *International Journal of Oncology*, vol. 24, No. 3, Mar. 1, 2004, 687-696.

Johnson et al., "Locked nucleic acid (LNA) single nucleotide polymorphism (SNP) genotype analysis and validation using real-time PCR", *Nucleic Acids Research*, vol. 32, No. 6, Mar. 26, 2004, e55 (1-9).

Josefsen et al., "Diagnostic PCR: Comparative sensitivity of four probe chemistries", *Molecular and Cellular Probes*, vol. 23, Nos. 2-4, Jun.-Aug. 2009, 201-203.

Koizumi et al., "Improvement of single nucleotide polymorphism genotyping by allele-specific PCR using primers modified with an ENA residue", *Analytical Biochemistry*, vol. 340, No. 2, Mar. 14, 2005, 287-294.

Kubista et al., "Light-up probe based real-time Q-PCR", *SPIE*, vol. 4264,, 2001, 53-58.

Kutyavin et al., "3'-Minor groove binder-DNA probes increase sequence specificity at PCR extension temperatures", *Nucleic Acids Research*, vol. 28, No. 2, Jan. 15, 2000, 655-661.

Kwok, "Methods for Genotyping Single Nucleotide Polymorphisms", *Annual Review of Genomics and Human Genetics*, vol. 2, 2001, 235-258.

Labrenz et al., "Development and Application of a Real-Time PCR Approach for Quantification of Uncultured Bacteria in the Central Baltic Sea", *Applied and Environmental Microbiology*, vol. 70, No. 8, Aug. 2004, 4971-4979.

Latorra, et al., "Enhanced Allele-Specific PCR Discrimination in SNP Genotyping Using 3' Locked Nucleic Acid (LNA) Primers", *Human Mutation*, vol. 22, No. 1, Jul. 1, 2003, 79-85.

Lee et al., "Increased Sensitivity and Specificity of Borrelia burgdorferi 16S Ribosomal DNA Detection", *American Journal of Clinical Pathology*, vol. 133, No. 4, Apr. 2010, 569-576.

Livak, "Allelic Discrimination Using Fluorogenic Probes and the 5' Nuclease Assay", *Genetic Analysis: Biomolecular Engineering*, vol. 14, Nos. 5-6, Feb. 1999, 143-149.

Lu et al., "Isolation of circulating epithelial and tumor progenitor cells with an invasive phenotype from breast cancer patients", *International Journal of Cancer*, vol. 126, No. 3, Feb. 1, 2010.

Lukhtanov et al., "Direct, Solid Phase Assembly of Dihydropyrroloindole Peptides with Conjugated Oligonucleotides", *Bioconjugate Chemistry*, vol. 7, No. 5, Sep. 26, 1996, 564-567.

Maxwell et al., "Self-Assembled Nanoparticle Probes for Recognition and Detection of Biomolecules", *Journal of the American Chemical Society*, vol. 124, No. 32, Aug. 14, 2002, 9606-9612.

May, "How Many Species Are There on Earth?", *Science, New Series*, vol. 241, No. 4872, Sep. 16, 1988, 1441-1449.

McKinzie et al., "ACB-PCR measurement of K-ras codon 12 mutant fractions in livers of Big Blue® rats treated with N-hydroxy-2-acetylaminofluorene", *Mutagenesis*, vol. 21, No. 6, Sep. 29, 2006, 391-397.

McKinzie et al., "Detection of rare K-ras codon 12 mutations using allele-specific competitive blocker PCR Mutat Res", *Mutation Research*, vol. 517, May 27, 2002, 209-220.

Mhlanga et al., "Using Molecular Beacons to Detect Single-Nucleotide Polymorphisms with Real-Time PCR", *Methods*, vol. 25, No. 4, Dec. 2001, 463-471.

Modrek et al., "Genome-wide detection of alternative splicing in expressed sequences of human genes", *Nucleic Acids Research*, vol. 29, No. 13., Jul. 1, 2001, 2850-2859.

Morlan et al., "Mutation Detection by Real-Time PCR: A Simple, Robust and Highly Selective Method", *PLoS One*, vol. 4, No. 2, Feb. 25, 2009, e4584 (1-11).

Nakitandwe et al., "Reliable allele detection using SNP-based PCR primers containing Locked Nucleic Acid: application in genetic mapping", *Plant Methods*, vol. 3, No. 2, 2007, 9 pages.

Noutsias et al., "Preamplification techniques for real-time RT-PCR analyses of endomyocardial biopsies", *BMC Molecular Biology*, vol. 9, No. 3, Jan. 14, 2008, 1-20.

Nybo, "Troubleshooting Forum: Molecular Biology Techniques Q&A", *DNA and General PCR Methods: Allele-specific PCR*, vol. 56, Feb. 2010, 101-102.

Orou et al., "Allele-specific competitive blocker PCR: a one-step method with applicability to pool screening", *Human Mutation*, vol. 6, No. 2, Jun. 1, 2005, 163-169.

Oshima et al., "Description of Thermus thermophilus (Yoshida and Oshima) comb. nov., a Nonsporulating Thermophilic Bacterium from a Japanese Thermal Spa", *International Journal of Systematic Bacteriology*, vol. 24, No. 1, 1974, 102-112.

Papp et al., "Single Nucleotide Polymorphism Genotyping Using Allele-Specific PCR and Fluorescence Melting Curves", *BioTechniques*, vol. 34, No. 5, May 2003, 1068-1072.

Parsons et al., "Allele-specific competitive blocker-PCR detection of rare base substitution", *Methods in Molecular Biology*, vol. 291, 2005, 235-245.

Parsons et al., "Detection of a mouse H-ras codon 61 mutation using a modified allele-specific competitive blocker PCR genotype selection method Mutagenesis", *Mutagenesis*, vol. 13, No. 6, Nov. 1998, 581-588.

Piggott et al., "A multiplex pre-amplification method that significantly improves microsatellite amplification and error rates for faecal DNA in limiting conditions", *Conservation Genetics*, vol. 5, No. 3, Jun. 2004, 417-420.

Reddy et al., "Synthetic DNA minor groove-binding drugs", *Pharmacology & Therapeutics*, vol. 84, No. 1, Oct. 1999, 1-111.

Riccelli et al., "Melting studies of dangling-ended DNA hairpins: effects of end length, loop sequence and biotynylationof loop bases", *Nucleic Acids Research*, vol. 30, No. 18,, Sep. 15, 2002, 4088-4093.

Roobol et al., "5-fluorouracil and 5-fluoro-2'-deoxyuridine follow different metabolic pathways in the induction of cell lethality in L1210 leukaemia", *British Journal of Cancer*, vol. 49, No. 6, Jun. 1984, 739-744.

Roux, "Optimization and Troubleshooting in PCR", *PCR Methods and Applications*; Downloaded from www.genome.org; Cold Spring Harbor Laboratory Press;, 1995, S185-S194.

Ruano et al., "PCR: The First Few Cycles", *Amplifications: A Forum for PCR Users*, Issue 7, Oct. 1991, 1-4.

Saunders, "Quantitative Real-Time PCR", *Current PCR*, www.horizonpress.com/pcrboooks, 2008, 1-22.

Seela et al., "The N8-(2'-deoxyribofuranoside) of 8-aza-7-deazaadenine: a universal nucleoside forming specific hydrogen bonds with the four canonical DNA constituents", *Nucleic Acids Research*, vol. 28, No. 17, 2000, 3224-3232.

Seyama et al., "A novel blocker-PCR method for detection of rare mutant alleles in the presence o f an excess amount of normal DNA", *Nucleic Acids Research*, vol. 20, No. 10, May 25, 1992, 2493-2496.

Shen et al., "Abnormal CpG island methylation occurs during in vitro differentiation of human embryonic stem cells", *Human Molecular Genetics*, vol. 15, No. 17, 2006, 2623-2635.

Solinas et al., "Duplex Scorpion primers in SNP analysis and FRET applications", *Nucleic Acids Research*, vol. 29, No. 20, E96, Oct. 15, 2001, 1-9.

Stathopoulou et al., "Real-Time Quantification of CK-19 mRNA-Positive Cells in Peripheral Blood of Breast Cancer Patients Using the Lightcycler System", *Clinical Cancer Research*, vol. 9, No. 14, Nov. 1, 2003, 5145-5151.

Svanvik et al., "Light-Up Probes: Thiazole Orange-Conjugated Peptide Nucleic Acid for Detection of Target Nucleic Acid in Homogenous Solution", *Analytical Biochemistry*, vol. 281,, 2000, 26-35.

(56) References Cited

OTHER PUBLICATIONS

Tabone et al., "Temperature Switch PCR (TSP): Robust assay design for reliable amplification and genotyping of SNPs", *BMC Genomics*, vol. 10, No. 580, Dec. 3, 2009, 1-14.

The International SNP Map Workin, "A map of human genome sequence variation containing 1.42 million single nucleotide polymorphisms", *Nature*, vol. 409, Feb. 15, 2001, 928-933.

Tsourkas et al., "Structure-function relationships of shared-stem and conventional molecular beacons", *Nucleic Acids Research*, vol. 30, No. 19, 2002, pp. 4208-4215.

Tyagi et al., "Molecular Beacons: Probes that Fluoresce upon Hybridization", *Nature Biotechnology*, vol. 14, No. 3, Mar. 1996, 303-308.

Unknown, Real Time PCR Tips, 1999, 94-99.

Uknown, "PCR principles and practices", downloaded from URL: http://irc.igd.cornell.edu/Protocols/PCR_principles.htm, Mar. 10, 2005, 1-3.

Van Der Auwera et al., "Circulating tumour cell detection: a direct comparison between the CellSearch System, the AdnaTest and CK-19/mammaglobin RT-PCR in patients with metastatic breast cancer", *British Journal of Cancer*, vol. 102, No. 2, Jan. 19, 2010, 276-284.

Van Hoeyveld et al., "Detection of signel nucleotide polymorphisms in the mannose-binding lectin gene using minor groove binder-DNA probes", *Journal of Immunological Methods*, vol. 287, 2004, 227-230.

Walker et al., "Progress in the design of DNA sequence-specific lexitropsins", *Biopolymers*, vol. 44, No. 4, 1997, 323-334.

Weighardt et al., "A simple procedure for enhancing PCR specificity", *Genome Research*, vol. 3, No. 1, Aug. 1993, 77-80.

Wemmer et al., "Targeting the minor groove of DNA", *Current Opinion in Structural Biology*, vol. 7, No. 3, 1997, 355-361.

Whitcombe et al., "Detection of PCR products using self-probing amplicons and fluorescence", *Nature Biotechnology*, vol. 17, No. 18, Aug. 1999, 804-807.

Wolffs et al., "PNA-Based Light-Up Probes for Real-Time Detection of Sequence-Specific PCR Products", *BioTechniques*, vol. 31, No. 4, Oct. 2001, 766-771.

Wu et al., "Allele-specific enzymatic amplification of β-globin genomic DNA for diagnosis of sickle cell anemia", *Proceedings of the National Academy of Sciences*, vol. 86, No. 8, Apr. 1989, 2757-2760.

Yao et al., "Evaluation of minor groove binding probe and Taqman probe PCR assays: Influence of mismatches and template complexity on quantification", *Molecular and Cellular Probes*, vol. 20, No. 5, Oct. 2006, 311-316.

Yu et al., "Electronic Detection of Single-Base Mismatches in DNA with Ferrocene-Modified Probes", *Journal of the American Chemical Society*, vol. 123, Issue 45, Nov. 14, 2001, 11155-11161.

Zhang et al., "Hairpin Probes for Real-time Assay of Restriction Endonucleases", *Acta Biochimica et Biophysica Sinic*, vol. 34, No. 2, Jun. 2002, 329-332 (abstract).

Ziegler et al., "Circulating DNA: a new diagnostic gold mine?", *Cancer Treatment Reviews*, vol. 28, No. 5, Oct. 2002, 255-271.

Zimmer et al., "Nonintercalating DNA-binding ligands: Specificity of the interaction and their use as tools in biophysical, biochemical and biological investigations of the genetic material", *Progress in Biophysics and Molecular Biology*, vol. 47, No. 1, 1986, 31-112.

Dominguez, P. et al. "Wild-type Blocking Polymerase Chain Reaction for detection of single nucleotide minority mutations from clinical specimens" Oncogene, vol. 24, 2005, pp. 6830-6834.

Johnson, M. "Italian Researchers Validate CastPCR as Companion to TKI Treatement for BRAF Mutated Melanoma", Genomeweb Jan. 20, 2016, https://www.genomeweb.com/pcr/italian-researchers-validate-castpcr-companion-tki-treatment-braf-mutated-melanoma; downloaded Feb. 24, 2016, pp. 1-4.

Punzel, M. et al. "The type of stromal feeder used in limiting dilution assays influences frequency and maintenance assessment of human long-term culture initiating cells", Leukemia, vol. 13, 1999, pp. 92-97.

KRAS mutations

```
  1 gtactggtgg agtatttgat agtgtattaa ccttatgtgt gacatgttct aatatagtca
 61 cattttcatt attttatta taacgcctgc tgaaaatgac tgaatataaa cttgtggtag
121 ttggagctgg tggcgtaggc aagagtgcct tgacgataca gctaattcag aatcattttg
181 tggacgaata tgatccaaca atagaggtaa atcttgtttt aatatgcata ttactggtgc
241 aggaccattc tttgatacag ataaaggttt ctctgaccat tttcatgagt
```
// CDS REGION         cod. 12-13

KRAS mutations

- 12 Asp (GGT>GAT)
- 12 Val (GGT>GTT)
- 12 Cys (GGT>TGT)
- 12 Ser (GGT>AGT)
- 12 Ala (GGT>GCT)
- 12 Arg (GGT>CGT)
- 13 Asp (GGC>GAC)

Fig. 6

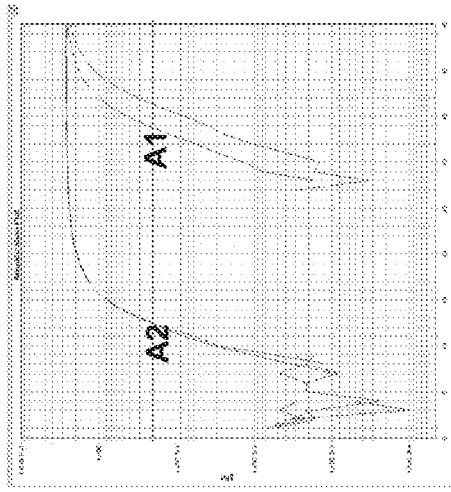
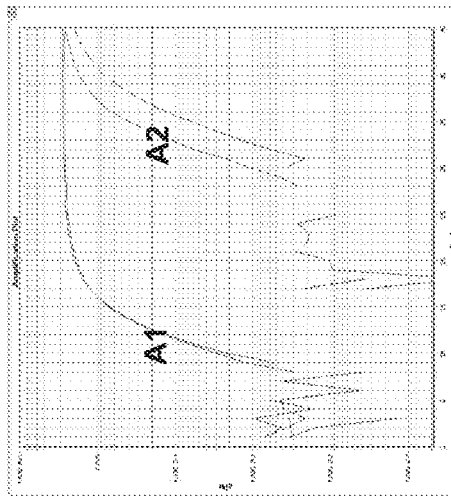
Fig. 7

Detection of Mutant DNA from Tumor Samples by cast-PCR

| SNP ID | Sample ID | Ct_WT | Ct_Mutant | Normalized ΔCt | Mutant cell DNA (%) |
|---|---|---|---|---|---|
| KRAS-38GA | Normal-1 | 23.2 | 40.0 | 16.8 | 0.00 |
| KRAS-38GA | Tumor-01 | 27.8 | 30.3 | 3.6 | 7.62 |
| EGFR-2573TG | Normal-1 | 22.9 | 40.0 | 17.1 | 0.00 |
| EGFR-2573TG | Tumor-02 | 27.7 | 25.4 | -2 | 80.00 |
| CTNNB1-134CT | Normal-1 | 22.8 | 40 | 17.2 | 0.00 |
| CTNNB1-134CT | Tumor-03 | 27.6 | 31.3 | -2.7 | 86.66 |
| KRAS-35GA | Normal-1 | 23.8 | 40 | 16.2 | 0.00 |
| KRAS-35GA | Tumor-04 | 30.9 | 31.7 | 0 | 50.00 |
| BRAF-1799TA | Normal-1 | 24.5 | 40 | 15.5 | 0.00 |
| BRAF-1799TA | Tumor-05 | 24.5 | 25 | 1.4 | 27.48 |
| NRAS-183AT | Normal-1 | 24.2 | 40 | 15.8 | 0.00 |
| NRAS-183AT | Tumor-06 | 29.8 | 40.0 | 5.9 | 1.65 |
| TP53-733GA | Normal-1 | 21.8 | 40 | 18.2 | 0.00 |
| TP53-733GA | Tumor-07 | 26.2 | 26.1 | 1.2 | 30.33 |

Fig. 10

List of Primers and Probes used in cast-PCR Assays

| SNP ID | Tailed Allele-specific Primer 1 (ASP1) | Sequence of ASP1 | Tailed Allele-specific Primer 2 (ASP2) | Sequence of ASP2 |
|---|---|---|---|---|
| CV11201742 | ASP1 | cccGCTGCTCCTGTGC | ASP2 | cccGGCTGCTCCTGTGT |
| CV11349123 | ASP1 | acccAACGCACAACTTAGCG | ASP2 | gccGAACGCACAACTTAGCA |
| CV1207700 | ASP1 | cccgCCTTGATGGATGGAGATTTAC | ASP2 | cccgCCTTGATGGATGGAGATTTAT |
| CV25594064 | ASP1 | gcacCCTTGGTGAAACAATTGTTG | ASP2 | tgcacCCTTGGTGAAACAATTGTTC |
| CV25639181 | ASP1 | cgccGAACTGGAAGTATTTTGACAG | ASP2 | cgccGAACTGGAAGTATTTTGACAT |

| SNP ID | Locus-specific Primer (LSP) | Sequence of LSP | Locus-specific TaqMan Probe (LST) | Sequence of LST |
|---|---|---|---|---|
| CV11201742 | LSP | TATCCCTCACAGAGAGAAGGGAG | LST | (6-FAM)ATGGCCCTGATAAGGGAGA(MGB) |
| CV11349123 | LSP | GCTTGCAATGGCTCCAACC | LST | (6-FAM)AGGGCGGTGCTCGAG(MGB) |
| CV1207700 | LSP | GGAGCCATTGCAAGCCAAG | LST | (6-FAM)TGTCACTCTACCCAGTAAA(MGB) |
| CV25594064 | LSP | TGGCAAGAGCGATGAGTACTC | LST | (6-FAM)AGAATCTGCCAATTACCTAGA(MGB) |
| CV25639181 | LSP | CTCTCAAAAGGTAACTGCCCACTTA | LST | (6-FAM)ACAAGTAGCTGATAATAAATG(MGB) |

| SNP ID | MGB Blocker 1 (MGB1) | Sequence of MGB1 | MGB Blocker 2 (MGB2) | Sequence of MGB2 |
|---|---|---|---|---|
| CV11201742 | MGB1 | CTCCTGTGCTGTCACC(MGB) | MGB2 | GCTCCTGTGTTGTCACC(MGB) |
| CV11349123 | MGB1 | CTTAGCGGCACGCAC(MGB) | MGB2 | CTTAGCAGCACGCACC(MGB) |
| CV1207700 | MGB1 | GGAGATTTACGCAATGTG(MGB) | MGB2 | TGGAGATTTATGCAATGTG(MGB) |
| CV25594064 | MGB1 | ACAATTGTTGAGGGGGG(MGB) | MGB2 | ACAATTGTTCAGGGGGG(MGB) |
| CV25639181 | MGB1 | AAGTATTTTGACAGCTTTAC(MGB) | MGB2 | AAGTATTTTGACATCTTTAC(MGB) |

Fig. 11A

| SNP ID | Tailed Allele-specific Primer 1 (ASP1) | Sequence of ASP1 with higher Tm | Tailed Allele-specific Primer 2 (ASP2) | Sequence of ASP2 with higher Tm |
|---|---|---|---|---|
| BRAF-1799TA | ASP1 | gccTGATTTTGGTCTAGCTACAGA | ASP2 | ccgGATTTTGGTCTAGCTACAGT |
| CTNNB1-121AG | ASP1 | cgcGAGAAGGAGCTGTGGT | ASP2 | gccAGAAGGAGCTGTGGC |
| CTNNB1-134CT | ASP1 | ccgTGCCTTTACCACTCAGAG | ASP2 | ccgTGCCTTTACCACTCAGAA |
| EGFR-2369CT | ASP1 | gcgCGTGCAGCTCATCAC | ASP2 | gcgCGTGCAGCTCATCAT |
| EGFR-2573TG | ASP1 | cggCAGCAGTTTGGCCC | ASP2 | cggCAGCAGTTTGGCCA |
| KRAS-176CG | ASP1 | gccGGATATTCTCGACACAGC | ASP2 | cgcTGGATATTCTCGACACAGG |
| KRAS-183AC | ASP1 | gcgGACACAGCAGGTCAA | ASP2 | gcgGACACAGCAGGTCAC |
| KRAS-183AT | ASP1 | gcgGACACAGCAGGTCAA | ASP2 | gcgGACACAGCAGGTCAT |
| KRAS-34GA | ASP1 | cgcCTTGCCTACGCCACT | ASP2 | gcgTTGCCTACGCCACC |
| KRAS-34GC | ASP1 | cgcTGCCTACGCCACG | ASP2 | gcgTTGCCTACGCCACC |
| KRAS-34GT | ASP1 | gcgTTGCCTACGCCACC | ASP2 | gcgTTGCCTACGCCACA |
| KRAS-35GA | ASP1 | cgcCTCTTGCCTACGCCAT | ASP2 | gcgTCTTGCCTACGCCAC |
| KRAS-35GC | ASP1 | gcgTCTTGCCTACGCCAG | ASP2 | gcgTCTTGCCTACGCCAC |
| KRAS-35GT | ASP1 | gcgTCTTGCCTACGCCAC | ASP2 | gcgTCTTGCCTACGCCAA |
| KRAS-38GA | ASP1 | cgcGTAGTTGGAGCTGGTGA | ASP2 | gccTAGTTGGAGCTGGTGG |
| NRAS-181CA | ASP1 | ccgATACTGGATACAGCTGGAA | ASP2 | ccgATACTGGATACAGCTGGAC |
| NRAS-183AT | ASP1 | ccgTGGATACAGCTGGACAA | ASP2 | cgcCTGGATACAGCTGGACAT |
| NRAS-35GA | ASP1 | ccgGGTGGTTGGAGCAGA | ASP2 | cgcGTGGTTGGAGCAGG |
| NRAS-38GA | ASP1 | ccgGGTTGGAGCAGGTGA | ASP2 | cgcGTTGGAGCAGGTGG |
| TP53-524GA | ASP1 | ccgGGAGGTTGTGAGGCA | ASP2 | ggcGAGGTTGTGAGGCG |
| TP53-637CT | ASP1 | gccGGATGACAGAAACACTTTTC | ASP2 | gccTGGATGACAGAAACACTTTTT |
| TP53-721TG | ASP1 | gcgTACAACTACATGTGTAACAGTG | ASP2 | ggcCTACAACTACATGTGTAACAGTT |
| TP53-733GA | ASP1 | gccTTCCTGCATGGGCA | ASP2 | gccTCCTGCATGGGCG |
| TP53-742CT | ASP1 | gccGGCGGCATGAACC | ASP2 | gccGGCGGCATGAACT |
| TP53-743GA | ASP1 | gccGCGGCATGAACCA | ASP2 | gccGCGGCATGAACCG |
| TP53-817CT | ASP1 | gccGCCAACAGCTTTGAGGTGC | ASP2 | cgcGAACAGCTTTGAGGTGT |

Fig. 11B

| SNP ID | Tailed Allele-specific Primer 1 (ASP1) | Sequence of ASP1 with lower Tm | Tailed Allele-specific Primer 2 (ASP2) | Sequence of ASP2 with lower Tm |
|---|---|---|---|---|
| BRAF-1799TA | ASP1 | cccgTGGTCTAGCTACAGA | ASP2 | cccgTGGTCTAGCTACAGT |
| CTNNB1-121AG | ASP1 | ccccAAGGAGCTGTGGT | ASP2 | ccccAGGAGCTGTGGC |
| CTNNB1-134CT | ASP1 | cgccCCTTTACCACTCAGAG | ASP2 | cgccCCTTTACCACTCAGAA |
| EGFR-2369CT | ASP1 | ggggaTGCAGCTCATCAC | ASP2 | ggggaGTGCAGCTCATCAT |
| EGFR-2573TG | ASP1 | ggcGCAGTTTGGCCC | ASP2 | gggGCAGTTTGGCCA |
| KRAS-176CG | ASP1 | cccgATTCTCGACACAGC | ASP2 | cccgATTCTCGACACAGG |
| KRAS-183AC | ASP1 | cgccCACAGCAGGTCAA | ASP2 | tgccCACAGCAGGTCAC |
| KRAS-183AT | ASP1 | tgccCACAGCAGGTCAA | ASP2 | cgccCACAGCAGGTCAT |
| KRAS-34GA | ASP1 | gccGCCTACGCCACT | ASP2 | accCCTACGCCACC |
| KRAS-34GC | ASP1 | agccCCTACGCCACG | ASP2 | agccCCTACGCCACC |
| KRAS-34GT | ASP1 | accCCTACGCCACC | ASP2 | accGCCTACGCCACA |
| KRAS-35GA | ASP1 | ggcTGCCTACGCCAT | ASP2 | ggggTGCCTACGCCAC |
| KRAS-35GC | ASP1 | gagcTGCCTACGCCAG | ASP2 | gggTGCCTACGCCAC |
| KRAS-35GT | ASP1 | ggcTGCCTACGCCAC | ASP2 | gggcTGCCTACGCCAA |
| KRAS-38GA | ASP1 | ccccGTTGGAGCTGGTGA | ASP2 | ccccTTGGAGCTGGTGG |
| NRAS-181CA | ASP1 | cgggTGGATACAGCTGGAA | ASP2 | cgggGGATACAGCTGGAC |
| NRAS-183AT | ASP1 | gggcGATACAGCTGGACAA | ASP2 | gggcGATACAGCTGGACAT |
| NRAS-35GA | ASP1 | gcccTGGTTGGAGCAGA | ASP2 | gcccGGTTGGAGCAGG |
| NRAS-38GA | ASP1 | cccGTTGGAGCAGGTGA | ASP2 | cccTTGGAGCAGGTGG |
| TP53-524GA | ASP1 | gccAGGTTGTGAGGCA | ASP2 | gccAGGTTGTGAGGCG |
| TP53-637CT | ASP1 | tgcccTGACAGAAACACTTTTC | ASP2 | tgccCTGACAGAAACACTTTTT |
| TP53-721TG | ASP1 | cgccCTACATGTGTAACAGTG | ASP2 | cgccCTACATGTGTAACAGTT |
| TP53-733GA | ASP1 | ccgCCTGCATGGGCA | ASP2 | ccgCTGCATGGGCG |
| TP53-742CT | ASP1 | cccGCGGCATGAACC | ASP2 | cccGCGGCATGAACT |
| TP53-743GA | ASP1 | cccCGGCATGAACCA | ASP2 | cccCGGCATGAACCG |
| TP53-817CT | ASP1 | cgcCAGCTTTGAGGTGC | ASP2 | cgcCAGCTTTGAGGTGT |

Fig. 11C

| SNP ID | Locus-specific Primer (LSP) | Sequence of LSP | Locus-specific TaqMan Probe (LST) | Sequence of LST |
|---|---|---|---|---|
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGCATGTCAAGATCAC(MGB) |
| KRAS-176CG | LSP | CCCTCCCCAGTCCTCATGTA | LST | (6-FAM)CTGGTCCCTCATTGCAC(MGB) |
| KRAS-183AC | LSP | TCTTCAAATGATTTAGTATTATTTATGGCAAATACACAAAG | LST | (6-FAM)CCCTCCCCAGTCCTCA(MGB) |
| KRAS-183AT | LSP | TCTTCAAATGATTTAGTATTATTTATGGCAAATACACAAAG | LST | (6-FAM)CCCTCCCCAGTCCTCA(MGB) |
| KRAS-34GA | LSP | TGTGTGACATGTTCTAATATAGTCACAT | LST | (6-FAM)CCTGCTGAAAATGAC(MGB) |
| KRAS-34GC | LSP | TGTGTGACATGTTCTAATATAGTCACAT | LST | (6-FAM)CCTGCTGAAAATGAC(MGB) |
| KRAS-34GT | LSP | TGTGTGACATGTTCTAATATAGTCACAT | LST | (6-FAM)CCTGCTGAAAATGAC(MGB) |
| KRAS-35GA | LSP | TGTGTGACATGTTCTAATATAGTCACAT | LST | (6-FAM)CCTGCTGAAAATGAC(MGB) |
| KRAS-35GC | LSP | TGTGTGACATGTTCTAATATAGTCACAT | LST | (6-FAM)CCTGCTGAAAATGAC(MGB) |
| KRAS-35GT | LSP | TGTGTGACATGTTCTAATATAGTCACAT | LST | (6-FAM)CCTGCTGAAAATGAC(MGB) |
| KRAS-38GA | LSP | GGTCCTGCACCAGTAATATGCA | LST | (6-FAM)TCGTCCACAAAATGATTC(MGB) |
| NRAS-181CA | LSP | GCAAATGACTTGCTATTATTGATGGCAAA | LST | (6-FAM)CCTTCGCCTGTCCTCATG(MGB) |
| NRAS-183AT | LSP | GCAAATGACTTGCTATTATTGATGGCAAA | LST | (6-FAM)CCTTCGCCTGTCCTCATG(MGB) |
| NRAS-35GA | LSP | AGTGGTTCTGGATTAGCTGGATTG | LST | (6-FAM)CAGTGCGCTTTTCC(MGB) |
| NRAS-38GA | LSP | GTGGTTCTGGATTAGCTGGATTGT | LST | (6-FAM)CAGTGCGCTTTTCC(MGB) |
| TP53-524GA | LSP | GCAACCAGCCCTGTCGTC | LST | (6-FAM)CTGCTCACCATCGCTATC(MGB) |
| TP53-637CT | LSP | AGACCCCAGTTGCAAACCAG | LST | (6-FAM)CCTCAGGCGGCTCATAG(MGB) |
| TP53-721TG | LSP | CTGGAGTCTTCCAGTGTGATGATG | LST | (6-FAM)ATGGGCCTCCGGTTCAT(MGB) |
| TP53-733GA | LSP | CTGGAGTCTTCCAGTGTGATGAT | LST | (6-FAM)ACGGAGGCCCATCCT(MGB) |
| TP53-742CT | LSP | TGTGCAGGGTGGCAAGT | LST | (6-FAM)CACACTGGAAGACTCC(MGB) |
| TP53-743GA | LSP | TGTGCAGGGTGGCAAGT | LST | (6-FAM)CACACTGGAAGACTCC(MGB) |
| TP53-817CT | LSP | CTTTCTTGCGGAGATTCTCTTCCT | LST | (6-FAM)CTGTGCGCCGGTCTC(MGB) |

Fig. 11D

| SNP ID | MGB Blocker 1 (MGB1) | Sequence of MGB1 | MGB Blocker 2 (MGB2) | Sequence of MGB2 |
|---|---|---|---|---|
| BRAF-1799TA | MGB1 | GCTACAGAGAAATCTC(MGB) | MGB2 | GCTACAGTGAAATCTC(MGB) |
| CTNNB1-121AG | MGB1 | GAGCTGTGGTAGTGGCA(MGB) | MGB2 | AGCTGTGGCAGTGGCA(MGB) |
| CTNNB1-134CT | MGB1 | CACTCAGAGAAGGAGC(MGB) | MGB2 | CACTCAGAAAGGAGC(MGB) |
| EGFR-2369CT | MGB1 | CATCACGCAGCTCATG(MGB) | MGB2 | TCATCATGCAGCTCATG(MGB) |
| EGFR-2573TG | MGB1 | AGTTTGGCCCGCCCAA(MGB) | MGB2 | AGTTTGGCCAGCCCAA(MGB) |
| KRAS-176CG | MGB1 | CTCGACACAGCAGGTCA(MGB) | MGB2 | CTCGACACAGGAGGTCA(MGB) |
| KRAS-183AC | MGB1 | GCAGGTCAAGAGGAGTAC(MGB) | MGB2 | CAGGTCACGAGGAGTAC(MGB) |
| KRAS-183AT | MGB1 | GCAGGTCAAGAGGAGTAC(MGB) | MGB2 | GCAGGTCATGAGGAGTAC(MGB) |
| KRAS-34GA | MGB1 | CGCCACTAGCTCCA(MGB) | MGB2 | CGCCACCAGCTCC(MGB) |
| KRAS-34GC | MGB1 | CCACGAGCTCCAACTA(MGB) | MGB2 | CCACCAGCTCCAACTA(MGB) |
| KRAS-34GT | MGB1 | ACGCCACCAGCTCC(MGB) | MGB2 | ACGCCACAAGCTCCAA(MGB) |
| KRAS-35GA | MGB1 | CGCCATCAGCTCC(MGB) | MGB2 | CGCCACCAGCTCC(MGB) |
| KRAS-35GC | MGB1 | CGCCAGCAGCTCC(MGB) | MGB2 | CGCCACCAGCTCC(MGB) |
| KRAS-35GT | MGB1 | CGCCACCAGCTCCA(MGB) | MGB2 | CGCCAACAGCTCCAA(MGB) |
| KRAS-38GA | MGB1 | GCTGGTGACGTAGGC(MGB) | MGB2 | GCTGGTGGCGTAGGC(MGB) |
| NRAS-181CA | MGB1 | GCTGGAAAAGAAGAGTAC(MGB) | MGB2 | GCTGGACAAGAAGAGTAC(MGB) |
| NRAS-183AT | MGB1 | CAGCTGGACAAGAAGAG(MGB) | MGB2 | CAGCTGGACATGAAGAG(MGB) |
| NRAS-35GA | MGB1 | TTGGAGCAGATGGTGTT(MGB) | MGB2 | TGGAGCAGGTGGTGTT(MGB) |
| NRAS-38GA | MGB1 | TGGAGCAGGTGATGTT(MGB) | MGB2 | TGGAGCAGGTGGTGTT(MGB) |
| TP53-524GA | MGB1 | TGAGGCACTGCCC(MGB) | MGB2 | TGAGGCGCTGCCC(MGB) |
| TP53-637CT | MGB1 | GAAACACTTTTCGACATAGTGTGGTG(MGB) | MGB2 | AGAAACACTTTTTGACATAGTGTGGTG(MGB) |
| TP53-721TG | MGB1 | TGTGTAACAGTGCCTGCATG(MGB) | MGB2 | ATGTGTAACAGTTCCTGCATG(MGB) |
| TP53-733GA | MGB1 | GCATGGGCAGCATG(MGB) | MGB2 | GCATGGGCGGCATG(MGB) |
| TP53-742CT | MGB1 | GCATGAACCGGAGGC(MGB) | MGB2 | GCATGAACTGGAGGCC(MGB) |
| TP53-743GA | MGB1 | CATGAACCAGAGGCC(MGB) | MGB2 | CATGAACCGGAGGCC(MGB) |
| TP53-817CT | MGB1 | TTGAGGTGCGTGTTTGTG(MGB) | MGB2 | TTTGAGGTGTGTGTTTGTGC(MGB) |

Fig. 11E

Pre-amplification of cast-PCR Reactions

| SNP ID | No Preamp | | | Preamp | | | Improvement |
|---|---|---|---|---|---|---|---|
| | Ct-A1 | Ct-A2 | ΔCt | Ct-A1 | Ct-A2 | ΔCt | ΔΔCt |
| KRAS-G12A_GC | 31.9 | 45.0 | 13.1 | 25.9 | 45.0 | 19.1 | 6.0 |
| KRAS-G12R_GC | 29.8 | 45.0 | 15.2 | 24.2 | 45.0 | 20.8 | 5.6 |
| KRAS-G12D_GA | 32.1 | 45.0 | 12.9 | 26.2 | 45.0 | 18.8 | 5.9 |
| KRAS-G12S_GA | 31.7 | 45.0 | 13.3 | 25.6 | 39.2 | 13.6 | 0.3 |
| KRAS-G13D_GA | 32.7 | 45.0 | 12.3 | 26.1 | 45.0 | 18.9 | 6.6 |
| KRAS-G12C_GT | 36.5 | 45.0 | 8.5 | 32.7 | 45.0 | 12.3 | 3.8 |
| KRAS-G12V_GT | 36.5 | 45.0 | 8.5 | 29.4 | 45.0 | 15.6 | 7.1 |
| Average | 33.0 | 45.0 | 12.0 | 27.2 | 44.2 | 17.0 | 5.0 |

Fig. 12

Effect of Tailed-ASP on cast-PCR

| SNP ID | Non-tailed ASP (ASP –tail) | | | Tailed ASP (ASP +tail) | | | Improvement |
|---|---|---|---|---|---|---|---|
| | ΔCt 10^6 A1/A1 | ΔCt 10^6 A2/A2 | Ave ΔCt | ΔCt 10^6 A1/A1 | ΔCt 10^6 A2/A2 | Ave ΔCt | ΔΔCt |
| BRAF-1799TA | 3.4 | 10.0 | 6.7 | 13.4 | 18.8 | 16.1 | 9.41 |
| CTNNB1-121AG | 10.6 | 6.8 | 8.7 | 10.1 | 16.2 | 13.2 | 4.46 |
| CTNNB1-134CT | 8.4 | 3.2 | 5.8 | 15.7 | 10.2 | 13.0 | 7.15 |
| EGFR-2369CT | 2.6 | 4.3 | 3.5 | 10.5 | 9.1 | 9.8 | 6.32 |
| EGFR-2573TG | 16.9 | 10.2 | 13.5 | 21.0 | 19.6 | 20.3 | 6.72 |
| KRAS-176CG | 7.2 | 17.9 | 12.5 | 23.0 | 20.8 | 21.9 | 9.37 |
| KRAS-183AC | 10.4 | 19.8 | 15.1 | 22.4 | 23.1 | 22.7 | 7.60 |
| KRAS-34GA | 11.0 | 9.5 | 10.2 | 11.0 | 16.4 | 13.7 | 3.42 |
| KRAS-35GA | 10.3 | 10.2 | 10.2 | 11.8 | 17.4 | 14.6 | 4.42 |
| KRAS-38GA | 5.6 | 9.1 | 7.3 | 10.8 | 13.8 | 12.3 | 4.92 |
| NRAS-181CA | 15.0 | 24.3 | 19.6 | 14.0 | 25.6 | 19.8 | 0.13 |
| NRAS-183AT | 9.5 | 11.2 | 10.3 | 16.2 | 20.6 | 18.4 | 8.06 |
| Average | | | 10.3 | | | 16.3 | 6.0 |

Fig. 13

Comparison of ASB-PCR and cast-PCR Assays

| SNP ID | ASB-PCR | | | cast-PCR | | | Improvement |
|---|---|---|---|---|---|---|---|
| | ΔCt 10^6 A1/A1 | ΔCt 10^6 A2/A2 | Ave ΔCt | ΔCt 10^6 A1/A1 | ΔCt 10^6 A2/A2 | Ave ΔCt | ΔΔCt |
| BRAF-1799TA | 10.6 | 15.7 | 13.2 | 13.4 | 18.8 | 16.1 | 2.93 |
| CTNNB1-121AG | 12.7 | 10.6 | 11.7 | 10.1 | 16.2 | 13.2 | 1.50 |
| CTNNB1-134CT | 13.2 | 7.9 | 10.6 | 15.7 | 10.2 | 13.0 | 2.38 |
| EGFR-2369CT | 7.6 | 10.0 | 8.8 | 10.5 | 9.1 | 9.8 | 1.00 |
| EGFR-2573TG | 17.8 | 17.1 | 17.5 | 21.0 | 19.6 | 20.3 | 2.81 |
| KRAS-176CG | 10.0 | 20.9 | 15.5 | 23.0 | 20.8 | 21.9 | 6.43 |
| KRAS-183AC | 19.7 | 21.5 | 20.6 | 22.4 | 23.1 | 22.7 | 2.15 |
| KRAS-34GA | 12.1 | 11.0 | 11.5 | 11.0 | 16.4 | 13.7 | 2.14 |
| KRAS-35GA | 12.7 | 13.7 | 13.2 | 11.8 | 17.4 | 14.6 | 1.42 |
| KRAS-38GA | 7.9 | 13.2 | 10.5 | 10.8 | 13.8 | 12.3 | 1.71 |
| NRAS-181CA | 15.1 | 24.6 | 19.9 | 14.0 | 25.6 | 19.8 | 0.09 |
| NRAS-183AT | 15.3 | 18.2 | 16.8 | 16.2 | 20.6 | 18.4 | 1.63 |
| Average | | | 14.1 | | | 16.3 | 2.2 |

Fig. 14

Comparison of MGB and Phosphate Blocker Probes in cast-PCR

| SNP ID | Phosphate blocker probe (PHOS1 and PHOS2) | | | MGB blocker probe (MGB1 and MGB2) | | | Improvement |
| --- | --- | --- | --- | --- | --- | --- | --- |
| | ΔCt 10^6 A1/A1 | ΔCt 10^6 A2/A2 | Ave ΔCt | ΔCt 10^6 A1/A1 | ΔCt 10^6 A2/A2 | Ave ΔCt | ΔΔCt |
| BRAF-1799TA | 10.1 | 14.1 | 12.12 | 10.2 | 14.1 | 12.10 | -0.02 |
| CTNNB1-121AG | 13.4 | 11.4 | 12.39 | 15.1 | 11.1 | 13.07 | 0.67 |
| CTNNB1-134CT | 13.3 | 8.3 | 10.80 | 14.0 | 12.2 | 13.13 | 2.34 |
| EGFR-2369CT | 9.7 | 11.3 | 10.50 | 11.3 | 9.9 | 10.59 | 0.09 |
| EGFR-2573TG | 18.4 | 23.1 | 20.71 | 18.9 | 21.7 | 20.29 | -0.42 |
| KRAS-176CG | 12.0 | 17.7 | 14.86 | 17.9 | 22.0 | 19.94 | 5.08 |
| KRAS-183AC | 26.6 | 22.1 | 24.39 | 30.2 | 20.7 | 25.44 | 1.06 |
| KRAS-34GA | 15.2 | 10.2 | 12.73 | 14.0 | 13.0 | 13.48 | 0.75 |
| KRAS-35GA | 15.4 | 11.8 | 13.58 | 15.4 | 12.2 | 13.83 | 0.25 |
| KRAS-38GA | 12.4 | 11.7 | 12.05 | 11.7 | 11.9 | 11.82 | -0.23 |
| NRAS-181CA | 17.1 | 22.1 | 19.59 | 16.2 | 24.4 | 20.30 | 0.71 |
| NRAS-183AT | 12.7 | 21.3 | 17.02 | 15.3 | 14.9 | 15.09 | -1.93 |
| Average | | | 15.1 | | | 15.8 | 0.7 |

Fig. 15

Effect of LNA Modified ASPs on cast-PCR

| SNP ID | cast-PCR | | | cast-PCR with LNA-modified ASP | | | Improvement |
|---|---|---|---|---|---|---|---|
| | ΔCt 10^6 A1/A1 | ΔCt 10^6 A2/A2 | Ave ΔCt | ΔCt 10^6 A1/A1 | ΔCt 10^6 A2/A2 | Ave ΔCt | ΔΔCt |
| BRAF-1799TA | 13.4 | 18.8 | 16.1 | 21.5 | 25.2 | 23.4 | 7.25 |
| CTNNB1-121AG | 10.1 | 16.2 | 13.2 | 9.4 | 19.0 | 14.2 | 1.02 |
| CTNNB1-134CT | 15.7 | 10.2 | 13.0 | 18.2 | 14.3 | 16.3 | 3.31 |
| EGFR-2369CT | 10.5 | 9.1 | 9.8 | 14.6 | 10.8 | 12.7 | 2.94 |
| EGFR-2573TG | 21.0 | 19.6 | 20.3 | 19.3 | 23.0 | 21.1 | 0.89 |
| KRAS-176CG | 23.0 | 20.8 | 21.9 | 26.6 | 21.9 | 24.3 | 2.37 |
| KRAS-183AC | 22.4 | 23.1 | 22.7 | 26.5 | 21.3 | 23.9 | 1.18 |
| KRAS-34GA | 11.0 | 16.4 | 13.7 | 8.9 | 17.2 | 13.1 | -0.59 |
| KRAS-35GA | 11.8 | 17.4 | 14.6 | 9.9 | 20.7 | 15.3 | 0.69 |
| KRAS-38GA | 10.8 | 13.8 | 12.3 | 15.9 | 12.5 | 14.2 | 1.91 |
| NRAS-181CA | 14.0 | 25.6 | 19.8 | 13.8 | 29.6 | 21.7 | 1.89 |
| NRAS-183AT | 16.2 | 20.6 | 18.4 | 18.0 | 24.7 | 21.3 | 2.96 |
| Average | | | 16.3 | | | 18.5 | 2.2 |

Fig. 16

Effect of Other Modified ASPs on cast-PCR

| | cast-PCR no modified ASP | | | cast-PCR with modified ASP* | | | | Improvement |
|---|---|---|---|---|---|---|---|---|
| SNP ID | ΔCt 10^6 A1/A1 | ΔCt 10^6 A2/A2 | Ave ΔCt | *Modified NT at 3' of ASP | ΔCt 10^6 A1/A1 | ΔCt 10^6 A2/A2 | Ave ΔCt | ΔΔCt |
| BRAF-1799TA | 13.2 | 19.5 | 16.4 | (ppA) | 14.1 | 23.2 | 18.6 | 2.2 |
| CTNNB1-121AG | 9.6 | 16.5 | 13.0 | (fdU) | 11.8 | 8.3 | 10.0 | -3.0 |
| CTNNB1-134CT | 15.2 | 10.5 | 12.8 | (ppG) | 15.6 | 14.9 | 15.3 | 2.4 |
| EGFR-2369CT | 8.9 | 9.1 | 9.0 | (iso dC) | 7.8 | 5.4 | 6.6 | -2.4 |
| EGFR-2573TG | 19.3 | 24.1 | 21.7 | (iso dC) | 19.2 | 27.2 | 23.2 | 1.5 |
| KRAS-176CG | 21.2 | 21.1 | 21.1 | (iso dC) | 25.5 | 16.5 | 21.0 | -0.1 |
| Average | | | 15.7 | | | | 15.8 | 0.1 |

Fig. 17

List of Primers and Probes used in Pre-amplification cast-PCR Assays

| SNP ID | Allele-1-specific Primer | Sequence of ASP1 | Allele-2-specific Primer | Sequence of ASP2 |
|---|---|---|---|---|
| KRAS-G12A_GC | ASP1 | CCCTGGTAGTTGGAGCTGG | ASP2 | CCCTGGTAGTTGGAGCTGC |
| KRAS-G12R_GC | ASP1 | CGCTGTGGTAGTTGGAGCTG | ASP2 | CGCTGTGGTAGTTGGAGCTC |
| KRAS-G12D_GA | ASP1 | GCCCGGTAGTTGGAGCTGG | ASP2 | GCCCGGTAGTTGGAGCTGA |
| KRAS-G12S_GA | ASP1 | CGCCGTGGTAGTTGGAGCTG | ASP2 | CGCCGTGGTAGTTGGAGCTA |
| KRAS-G13D_GA | ASP1 | CCCCAGTTGGAGCTGGTGG | ASP2 | CCCCAGTTGGAGCTGGTGA |
| KRAS-G12C_GT | ASP1 | GCCTTGCCTACGCCACA | ASP2 | GCCTTGCCTACGCCACC |
| KRAS-G12V_GT | ASP1 | GCCTCTTGCCTACGCCAA | ASP2 | GCCTCTTGCCTACGCCAC |

| SNP ID | Locus-specific Primer | Sequence of LSP | Locus-specific TaqMan Probe | Sequence of LST |
|---|---|---|---|---|
| KRAS-G12A_GC | LSP | AAAGAATGGTCCTGCACCAGTAA | LST | (6-FAM)ATGCATATTAAAACAAGATTTAC(MGB) |
| KRAS-G12R_GC | LSP | GGTCCTGCACCAGTAATATGCA | LST | (6-FAM)AACAATAGAGGTAAATCTTG(MGB) |
| KRAS-G12D_GA | LSP | AAAGAATGGTCCTGCACCAGTAA | LST | (6-FAM)ATGCATATTAAAACAAGATTTAC(MGB) |
| KRAS-G12S_GA | LSP | AAAGAATGGTCCTGCACCAGTAA | LST | (6-FAM)ATGCATATTAAAACAAGATTTAC(MGB) |
| KRAS-G13D_GA | LSP | AAAGAATGGTCCTGCACCAGTAA | LST | (6-FAM)ATGCATATTAAAACAAGATTTAC(MGB) |
| KRAS-G12C_GT | LSP | GAGTTTGTATTAAAAGGTACTGGTGGAGT | LST | (6-FAM)ACCTTATGTGTGACATGTTC(MGB) |
| KRAS-G12V_GT | LSP | GAGTTTGTATTAAAAGGTACTGGTGGAGT | LST | (6-FAM)ACCTTATGTGTGACATGTTC(MGB) |

Fig. 18A

List of Primers and Probes used in Pre-amplification cast-PCR Assays (Continued)

| SNP ID | Allele-1 MGB Blocker | Sequence of MGB1 | Allele-2 MGB Blocker | Sequence of MGB2 |
|---|---|---|---|---|
| KRAS-G12A_GC | MGB1 | TGGAGCTGCTGGCGTA(MGB) | MGB2 | TGGAGCTGGTGGCGTA(MGB) |
| KRAS-G12R_GC | MGB1 | TGGAGCTCGTGGCGTA(MGB) | MGB2 | TGGAGCTGGTGGCGTA(MGB) |
| KRAS-G12D_GA | MGB1 | TTGGAGCTGATGGCGTA(MGB) | MGB2 | TGGAGCTGGTGGCGTA(MGB) |
| KRAS-G12S_GA | MGB1 | TAGTTGGAGCTAGTGGCGTA(MGB) | MGB2 | TGGAGCTGGTGGCGTA(MGB) |
| KRAS-G13D_GA | MGB1 | TTGGAGCTGGTGACGTA(MGB) | MGB2 | TGGAGCTGGTGGCGTA(MGB) |
| KRAS-G12C_GT | MGB1 | CGCCACCAGCTCCA(MGB) | MGB2 | CGCCACAAGCTCCA(MGB) |
| KRAS-G12V_GT | MGB1 | CTACGCCACCAGCTC(MGB) | MGB2 | TACGCCAACAGCTC(MGB) |

Fig. 18B

List of Primers and Probes used in cast-PCR Assays

| SNP ID | Untailed Allele-1-specific Primer | Sequence of ASP1 without tails | Non-tailed Allele-2-specific Primer | Sequence of ASP2 without tails |
|---|---|---|---|---|
| BRAF-1799TA | ASP1-tail | TGATTTTGGTCTAGCTACAGA | ASP2-tail | GATTTTGGTCTAGCTACAGT |
| CTNNB1-121AG | ASP1-tail | GAGAAGGAGCTGTGGT | ASP2-tail | AGAAGGAGCTGTGGC |
| CTNNB1-134CT | ASP1-tail | TGCCTTTACCACTCAGAG | ASP2-tail | TGCCTTTACCACTCAGAA |
| EGFR-2369CT | ASP1-tail | CGTGCAGCTCATCAC | ASP2-tail | CGTGCAGCTCATCAT |
| EGFR-2573TG | ASP1-tail | CAGCAGTTTGGCCC | ASP2-tail | CAGCAGTTTGGCCA |
| KRAS-176CG | ASP1-tail | GGATATTCTCGACACAGC | ASP2-tail | TGGATATTCTCGACACAGG |
| KRAS-183AC | ASP1-tail | GACACAGCAGGTCAA | ASP2-tail | GACACAGCAGGTCAC |
| KRAS-34GA | ASP1-tail | CTTGCCTACGCCACT | ASP2-tail | TTGCCTACGCCACC |
| KRAS-35GA | ASP1-tail | CTCTTGCCTACGCCAT | ASP2-tail | TCTTGCCTACGCCAC |
| KRAS-3GA | ASP1-tail | GTAGTTGGAGCTGGTGA | ASP2-tail | TAGTTGGAGCTGGTGG |
| NRAS-181CA | ASP1-tail | ATACTGGATACAGCTGGAA | ASP2-tail | ATACTGGATACAGCTGGAC |
| NRAS-183AT | ASP1-tail | TGGATACAGCTGGACAA | ASP2-tail | CTGGATACAGCTGGACAT |

Fig. 19A

List of Primers and Probes used in cast-PCR Assays

| SNP ID | Tailed Allele-1-specific Primer | Sequence of ASP1 with tails | Tailed Allele-2-specific Primer | Sequence of ASP2 with tails |
|---|---|---|---|---|
| BRAF-1799TA | ASP1+tail | gccTGATTTTGGTCTAGCTACAGA | ASP2+tail | ccgGATTTTGGTCTAGCTACAGT |
| CTNNB1-121AG | ASP1+tail | cgcGAGAAGGAGCTGTGGT | ASP2+tail | gccAGAAGGAGCTGTGGC |
| CTNNB1-134CT | ASP1+tail | ccgTGCCTTTACCACTCAGAG | ASP2+tail | ccgTGCCTTTACCACTCAGAA |
| EGFR-2369CT | ASP1+tail | gcgCGTGCAGCTCATCAC | ASP2+tail | gcgCGTGCAGCTCATCAT |
| EGFR-2573TG | ASP1+tail | cggCAGCAGTTTGGCCC | ASP2+tail | cggCAGCAGTTTGGCCA |
| KRAS-176CG | ASP1+tail | gccGGATATTCTCGACACAGC | ASP2+tail | cgcTGGATATTCTCGACACAGG |
| KRAS-183AC | ASP1+tail | gcgGACACAGCAGGTCAA | ASP2+tail | gcgGACACAGCAGGTCAC |
| KRAS-34GA | ASP1+tail | cgcCTTGCCTACGCCACT | ASP2+tail | gcgTTGCCTACGCCACC |
| KRAS-35GA | ASP1+tail | cgcCTCTTGCCTACGCCAT | ASP2+tail | gcgTCTTGCCTACGCCAC |
| KRAS-38GA | ASP1+tail | cgcGTAGTTGGAGCTGGTGA | ASP2+tail | gccTAGTTGGAGCTGGTGG |
| NRAS-181CA | ASP1+tail | ccgATACTGGATACAGCTGGAA | ASP2+tail | ccgATACTGGATACAGCTGGAC |
| NRAS-183AT | ASP1+tail | ccgTGGATACAGCTGGACAA | ASP2+tail | cgcCTGGATACAGCTGGACAT |

Fig. 19B

List of Primers and Probes used in cast-PCR Assays

| SNP ID | Locus-specific Primer | Sequence of LSP | Locus-specific TaqMan Probe | Sequence of LST |
|---|---|---|---|---|
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGCATGTCAAGATCAC(MGB) |
| KRAS-176CG | LSP | CCCTCCCCAGTCCTCATGTA | LST | (6-FAM)CTGGTCCCTCATTGCAC(MGB) |
| KRAS-183AC | LSP | TCTTCAAATGATTTAGTATTATTTATGGCAAATACACAAAG | LST | (6-FAM)CCCTCCCCAGTCCTCA(MGB) |
| KRAS-34GA | LSP | TGTGTGACATGTTCTAATATAGTCACAT | LST | (6-FAM)CCTGCTGAAAATGAC(MGB) |
| KRAS-35GA | LSP | TGTGTGACATGTTCTAATATAGTCACAT | LST | (6-FAM)CCTGCTGAAAATGAC(MGB) |
| KRAS-38GA | LSP | GGTCCTGCACCAGTAATATGCA | LST | (6-FAM)TCGTCCACAAAATGATTC(MGB) |
| NRAS-181CA | LSP | GCAAATGACTTGCTATTATTGATGGCAAA | LST | (6-FAM)CCTTCGCCTGTCCTCATG(MGB) |
| NRAS-183AT | LSP | GCAAATGACTTGCTATTATTGATGGCAAA | LST | (6-FAM)CCTTCGCCTGTCCTCATG(MGB) |

Fig. 19C

List of Primers and Probes used in cast-PCR Assays

| SNP ID | Allele-1 MGB Blocker | Sequence of MGB1 | Allele-2 MGB Blocker | Sequence of MGB2 |
|---|---|---|---|---|
| BRAF-1799TA | MGB1 | CTACAGAGAAATCT(MGB) | MGB2 | CTACAGTGAAATCT(MGB) |
| CTNNB1-121AG | MGB1 | CTGTGGTAGTGGCA(MGB) | MGB2 | TGTGGCAGTGGCA(MGB) |
| CTNNB1-134CT | MGB1 | CTCAGAGAAGGAGC(MGB) | MGB2 | CTCAGAAAGGAGC(MGB) |
| EGFR-2369CT | MGB1 | ATCACGCAGCTCA(MGB) | MGB2 | CATCATGCAGCTCA(MGB) |
| EGFR-2573TG | MGB1 | GGCCCGCCCAA(MGB) | MGB2 | TGGCCAGCCCAA(MGB) |
| KRAS-176CG | MGB1 | GACACAGCAGGTCA(MGB) | MGB2 | GACACAGGAGGTCA(MGB) |
| KRAS-183AC | MGB1 | CAGGTCAAGAGGAGTA(MGB) | MGB2 | AGGTCACGAGGAGTA(MGB) |
| KRAS-34GA | MGB1 | GCCACTAGCTCCA(MGB) | MGB2 | CCACCAGCTCCA(MGB) |
| KRAS-35GA | MGB1 | GCCATCAGCTCC(MGB) | MGB2 | CCACCAGCTCC(MGB) |
| KRAS-38GA | MGB1 | TGGTGACGTAGGC(MGB) | MGB2 | TGGTGGCGTAGGC(MGB) |
| NRAS-181CA | MGB1 | GCTGGAAAAGAAGAG(MGB) | MGB2 | CTGGACAAGAAGAG(MGB) |
| NRAS-183AT | MGB1 | CTGGACAAGAAGAG(MGB) | MGB2 | CTGGACATGAAGAG(MGB) |

Fig. 19D

List of Primers and Probes used in ASB-PCR Assays

| SNP ID | Allele-1-Specific Primer (ASP1) | Sequence of ASP1 | Allele-2-Specific Primer (ASP2) | Sequence of ASP2 |
|---|---|---|---|---|
| BRAF-1799TA | ASP1 | GTGATTTTGGTCTAGCTACAGA | ASP2 | GTGATTTTGGTCTAGCTACAGT |
| CTNNB1-121AG | ASP1 | TCAGAGAAGGAGCTGTGGT | ASP2 | TCAGAGAAGGAGCTGTGGC |
| CTNNB1-134CT | ASP1 | GATTGCCTTTACCACTCAGAG | ASP2 | GATTGCCTTTACCACTCAGAA |
| EGFR-2369CT | ASP1 | CACCGTGCAGCTCATCAC | ASP2 | CACCGTGCAGCTCATCAT |
| EGFR-2573TG | ASP1 | CACCCAGCAGTTTGGCCC | ASP2 | CACCCAGCAGTTTGGCCA |
| KRAS-176CG | ASP1 | TTGGATATTCTCGACACAGC | ASP2 | CTTGGATATTCTCGACACAGG |
| KRAS-183AC | ASP1 | CTCGACACAGCAGGTCAA | ASP2 | TCTCGACACAGCAGGTCAC |
| KRAS-34GA | ASP1 | ACTCTTGCCTACGCCACT | ASP2 | ACTCTTGCCTACGCCACC |
| KRAS-35GA | ASP1 | CACTCTTGCCTACGCCAT | ASP2 | CACTCTTGCCTACGCCAC |
| KRAS-38GA | ASP1 | TGGTAGTTGGAGCTGGTGA | ASP2 | TGGTAGTTGGAGCTGGTGG |
| NRAS-181CA | ASP1 | CATACTGGATACAGCTGGAA | ASP2 | CATACTGGATACAGCTGGAC |
| NRAS-183AT | ASP1 | ATACTGGATACAGCTGGACAA | ASP2 | TACTGGATACAGCTGGACAT |

Fig. 20A

List of Primers and Probes used in ASB-PCR Assays

| SNP ID | Locus-specific Primer (LSP) | Sequence of LSP | Locus-specific TaqMan Probe (LST) | Sequence of LST |
|---|---|---|---|---|
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGCATGTCAAGATCAC(MGB) |
| KRAS-176CG | LSP | CCCTCCCCAGTCCTCATGTA | LST | (6-FAM)CTGGTCCCTCATTGCAC(MGB) |
| KRAS-183AC | LSP | TCTTCAAATGATTTAGTATTATTTATGGCAAATACACAAAG | LST | (6-FAM)CCCTCCCCAGTCCTCA(MGB) |
| KRAS-34GA | LSP | TGTGTGACATGTTCTAATATAGTCACAT | LST | (6-FAM)CCTGCTGAAAATGAC(MGB) |
| KRAS-35GA | LSP | TGTGTGACATGTTCTAATATAGTCACAT | LST | (6-FAM)CCTGCTGAAAATGAC(MGB) |
| KRAS-38GA | LSP | GGTCCTGCACCAGTAATATGCA | LST | (6-FAM)TCGTCCACAAAATGATTC(MGB) |
| NRAS-181CA | LSP | GCAAATGACTTGCTATTATTGATGGCAAA | LST | (6-FAM)CCTTCGCCTGTCCTCATG(MGB) |
| NRAS-183AT | LSP | GCAAATGACTTGCTATTATTGATGGCAAA | LST | (6-FAM)CCTTCGCCTGTCCTCATG(MGB) |

Fig. 20B

List of Primers and Probes used in ASB-PCR Assays – Phosphate Blocker Probes

| SNP ID | Allele-1 PO⁴ Blocker | Sequence of PHOS1 | Allele-2 PO⁴ Blocker | Sequence of PHOS2 |
|---|---|---|---|---|
| BRAF-1799TA | PHOS1 | GCTACAGAGAAATCTCGATGG(Phos) | PHOS2 | TAGCTACAGTGAAATCTCGATG(Phos) |
| CTNNB1-121AG | PHOS1 | GAGCTGTGGTAGTGGCA(Phos) | PHOS2 | GAGCTGTGGCAGTGG(Phos) |
| CTNNB1-134CT | PHOS1 | TTACCACTCAGAGAAGGAGC(Phos) | PHOS2 | TTACCACTCAGAAAAGGAGCT(Phos) |
| EGFR-2369CT | PHOS1 | GCTCATCACGCAGCTCA(Phos) | PHOS2 | CAGCTCATCATGCAGCTCAT(Phos) |
| EGFR-2573TG | PHOS1 | TTGGCCCGCCCAAAAT(Phos) | PHOS2 | GTTTGGCCAGCCCAAAATC(Phos) |
| KRAS-176CG | PHOS1 | GACACAGCAGGTCACGAG(Phos) | PHOS2 | GACACAGGAGGTCAGGAG(Phos) |
| KRAS-183AC | PHOS1 | CAGCAGGTCAAGAGGAGTAC(Phos) | PHOS2 | CAGCAGGTCACGAGGAGTA(Phos) |
| KRAS-34GA | PHOS1 | CTACGCCACTAGCTCCAAC(Phos) | PHOS2 | TACGCCACCAGCTCCAA(Phos) |
| KRAS-35GA | PHOS1 | CTACGCCATCAGCTCC(Phos) | PHOS2 | TACGCCACCAGCTCCA(Phos) |
| KRAS-38GA | PHOS1 | CTGGTGACGTAGGCAAG(Phos) | PHOS2 | CTGGTGGCGTAGGCAAG(Phos) |
| NRAS-181CA | PHOS1 | GGATACAGCTGGAAAAGAAGAG(Phos) | PHOS2 | ATACAGCTGGACAAGAAGAGT(Phos) |
| NRAS-183AT | PHOS1 | AGCTGGACAAGAAGAGTACA(Phos) | PHOS2 | AGCTGGACATGAAGAGTACA(Phos) |

Fig. 20C

List of Primers and Probes for cast-PCR Assays using LNA-modified ASPs

| SNP ID | Allele-1-specific Primer | Sequence of ASP1 | Allele-2-specific Primer | Sequence of ASP2 |
|---|---|---|---|---|
| BRAF-1799TA | ASP1 | CCCCTTTTGGTCTAGCTACAG(+A) | ASP2 | CCCCTTTTGGTCTAGCTACAG(+T) |
| CTNNB1-121AG | ASP1 | GCCCGAAGGAGCTGTGG(+T) | ASP2 | GCCCGAAGGAGCTGTGG(+C) |
| CTNNB1-134CT | ASP1 | CGCCCCTTTACCACTCAGA(+G) | ASP2 | CGCCCCTTTACCACTCAGA(+A) |
| EGFR-2369CT | ASP1 | GCGGGTGCAGCTCATCA(+C) | ASP2 | GCGGGTGCAGCTCATCA(+T) |
| EGFR-2573TG | ASP1 | CGGGAGCAGTTTGGCC(+C) | ASP2 | CGGGAGCAGTTTGGCC(+A) |
| KRAS-176CG | ASP1 | GCCCGATATTCTCGACACAG(+C) | ASP2 | GCCCGATATTCTCGACACAG(+G) |
| KRAS-183AC | ASP1 | GCGGACACAGCAGGTCA(+A) | ASP2 | GCGGACACAGCAGGTCA(+C) |
| KRAS-34GA | ASP1 | CGGTGCCTACGCCAC(+T) | ASP2 | CGGTGCCTACGCCAC(+C) |
| KRAS-35GA | ASP1 | CGCCTTGCCTACGCCA(+T) | ASP2 | CGCCTTGCCTACGCCA(+C) |
| KRAS-38GA | ASP1 | GCCCAGTTGGAGCTGGTG(+A) | ASP2 | GCCCAGTTGGAGCTGGTG(+G) |
| NRAS-181CA | ASP1 | CGCCACTGGATACAGCTGGA(+A) | ASP2 | CGCCACTGGATACAGCTGGA(+C) |
| NRAS-183AT | ASP1 | CCGCGGATACAGCTGGACA(+A) | ASP2 | CCGCGGATACAGCTGGACA(+T) |

"+" indicates an LNA modification

Fig. 21A

List of Primers and Probes for cast-PCR Assays using LNA-modified ASPs

| SNP ID | Locus-specific Primer (LSP) | Sequence of LSP | Locus-specific TaqMan Probe (LST) | Sequence of LST |
|---|---|---|---|---|
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGCATGTCAAGATCAC(MGB) |
| KRAS-176CG | LSP | CCCTCCCCAGTCCTCATGTA | LST | (6-FAM)CTGGTCCCTCATTGCAC(MGB) |
| KRAS-183AC | LSP | TCTTCAAATGATTTAGTATTATTTATGGCAAATACACAAAG | LST | (6-FAM)CCCTCCCCAGTCCTCA(MGB) |
| KRAS-34GA | LSP | TGTGTGACATGTTCTAATATAGTCACAT | LST | (6-FAM)CCTGCTGAAAATGAC(MGB) |
| KRAS-35GA | LSP | TGTGTGACATGTTCTAATATAGTCACAT | LST | (6-FAM)CCTGCTGAAAATGAC(MGB) |
| KRAS-38GA | LSP | GGTCCTGCACCAGTAATATGCA | LST | (6-FAM)TCGTCCACAAAATGATTC(MGB) |
| NRAS-181CA | LSP | GCAAATGACTTGCTATTATTGATGGCAAA | LST | (6-FAM)CCTTCGCCTGTCCTCATG(MGB) |
| NRAS-183AT | LSP | GCAAATGACTTGCTATTATTGATGGCAAA | LST | (6-FAM)CCTTCGCCTGTCCTCATG(MGB) |

Fig. 21B

List of Primers and Probes for cast-PCR Assays using LNA-modified ASPs

| SNP ID | Allele-1 MGB Blocker | Sequence of MGB1 | Allele-2 MGB Blocker | Sequence of MGB2 |
|---|---|---|---|---|
| BRAF-1799TA | MGB1 | CTACAGAGAAATCT(MGB) | MGB2 | CTACAGTGAAATCT(MGB) |
| CTNNB1-121AG | MGB1 | CTGTGGTAGTGGCA(MGB) | MGB2 | TGTGGCAGTGGCA(MGB) |
| CTNNB1-134CT | MGB1 | CTCAGAGAAGGAGC(MGB) | MGB2 | CTCAGAAAAGGAGC(MGB) |
| EGFR-2369CT | MGB1 | ATCACGCAGCTCA(MGB) | MGB2 | CATCATGCAGCTCA(MGB) |
| EGFR-2573TG | MGB1 | GGCCCGCCCAA(MGB) | MGB2 | TGGCCAGCCCAA(MGB) |
| KRAS-176CG | MGB1 | GACACAGCAGGTCA(MGB) | MGB2 | GACACAGGAGGTCA(MGB) |
| KRAS-183AC | MGB1 | CAGGTCAAGAGGAGTA(MGB) | MGB2 | AGGTCACGAGGAGTA(MGB) |
| KRAS-34GA | MGB1 | GCCACTAGCTCCA(MGB) | MGB2 | CCACCAGCTCCA(MGB) |
| KRAS-35GA | MGB1 | GCCATCAGCTCC(MGB) | MGB2 | CCACCAGCTCC(MGB) |
| KRAS-38GA | MGB1 | TGGTGACGTAGGC(MGB) | MGB2 | TGGTGGCGTAGGC(MGB) |
| NRAS-181CA | MGB1 | GCTGGAAAAGAAGAG(MGB) | MGB2 | CTGGACAAGAAGAG(MGB) |
| NRAS-183AT | MGB1 | CTGGACAAGAAGAG(MGB) | MGB2 | CTGGACATGAAGAG(MGB) |

Fig. 21C

List of Primers and Probes for cast-PCR Assays using chemically modified ASPs

| SNP ID | Allele-1-specific Primer | Sequence of ASP1 | Allele-2-specific Primer | Sequence of ASP2 |
|---|---|---|---|---|
| BRAF-1799TA | ASP1 | CCCCTTTTGGTCTAGCTACAG(ppA) | ASP2 | CCCCTTTTGGTCTAGCTACAG(fdU) |
| CTNNB1-121AG | ASP1 | GCCCGAAGGAGCTGTGG(fdU) | ASP2 | GCCCGAAGGAGCTGTGG(iso dC) |
| CTNNB1-134CT | ASP1 | CGCCCCTTTACCACTCAGA(ppG) | ASP2 | CGCCCCTTTACCACTCAGA(ppA) |
| EGFR-2369CT | ASP1 | GCGGGTGCAGCTCATCA(iso dC) | ASP2 | GCGGGTGCAGCTCATCA(fdU) |
| EGFR-2573TG | ASP1 | CGGGAGCAGTTTGGCC(iso dC) | ASP2 | CGGGAGCAGTTTGGCC(ppA) |
| KRAS-176CG | ASP1 | GCCCGATATTCTCGACACAG(iso dC) | ASP2 | GCCCGATATTCTCGACACAG(ppG) |
| SNP ID | Locus-specific Primer (LSP) | Sequence of LSP | Locus-specific TaqMan Probe (LST) | Sequence of LST |
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGCATGTCAAGATCAC(MGB) |
| KRAS-176CG | LSP | CCCTCCCCAGTCCTCATGTA | LST | (6-FAM)CTGGTCCCTCATTGCAC(MGB) |
| SNP ID | Allele-1 MGB Blocker | Sequence of MGB1 | Allele-2 MGB Blocker | Sequence of MGB2 |
| BRAF-1799TA | MGB1 | CTACAGAGAAATCT(MGB) | MGB2 | CTACAGTGAAATCT(MGB) |
| CTNNB1-121AG | MGB1 | CTGTGGTAGTGGCA(MGB) | MGB2 | TGTGGCAGTGGCA(MGB) |
| CTNNB1-134CT | MGB1 | CTCAGAGAAGGAGC(MGB) | MGB2 | CTCAGAAAGGAGC(MGB) |
| EGFR-2369CT | MGB1 | ATCACGCAGCTCA(MGB) | MGB2 | CATCATGCAGCTCA(MGB) |
| EGFR-2573TG | MGB1 | GGCCCGCCCAA(MGB) | MGB2 | TGGCCAGCCCAA(MGB) |
| KRAS-176CG | MGB1 | GACACAGCAGGTCA(MGB) | MGB2 | GACACAGGAGGTCA(MGB) |

Fig. 22

SEQUENCE LISTING

<160> NUMBER OF SEQ ID NOS: 635

<210> SEQ ID NO 1
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gctctgcttc attcctgtct gaagaagggc agatagtttg gctgctcctg tgytgtcacc     60
tgcaattctc ccttatcagg gccattggcc tctcccttct ctctgtgagg gatattttct   120
ctgacttgtc aatccacatc ttcc                                          144

<210> SEQ ID NO 2
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcttgcaat ggctccaacc ggaagggcgg tgctcgagct gtggtgcgtg cygctaagtt     60
gtgcgttcca gggtgcactc gc                                            82

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaactatac ccttgatgga tggagattta ygcaatgtgt tttactgggt agagtgacag     60
acctt                                                               65

<210> SEQ ID NO 4
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cctgaactta tttggcaaga gcgatgagta ctcttaaaat tactatctgg aaattatatt     60
atttagaatc tgccaattac ctagatcccc cctsaacaat tgtttcacca aggaacttcc   120
tgaa                                                                124

<210> SEQ ID NO 5
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaattggttg tctccttatg ggaactggaa gtattttgac akctttacca catttcttca     60

```
tgggatagta agtgttaaac agctctgagc catttattat cagctacttg taaattagca    120
gtagaatttt atttttatac ttgtaagtgg gcagttacct tttgagagga atacctatag    180
```

<210> SEQ ID NO 6
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gcggagggaa gctcatcagt ggggccacga gctgagtgcg tcctgtcact ccactcccat    60
gtcccttggg aaggtctgag actaggg                                       87
```

<210> SEQ ID NO 7
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
tactacacct cagatatatt tcttcatgaa gacctcacag taaaaatagg tgattttggt    60
ctagctacag wgaaatctcg atggagtggg tcccatcagt ttgaacagtt gtctggatcc    120
attttgtgga tggtaagaat tgaggctatt tttccactga ttaaattttt ggccctgaga    180
tgctgctgag tt                                                       192
```

<210> SEQ ID NO 8
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tgctaatact gtttcgtatt tatagctgat ttgatggagt tggacatggc catggaacca    60
gacagaaaag cggctgttag tcactggcag caacagtctt acctggactc tggaatccat    120
tctggtgcca ctrccacagc tccttctctg agtggtaaag gcaatcctga ggaagaggat    180
gtggatacct cccaagtc                                                 198
```

<210> SEQ ID NO 9
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
tttgatggag ttggacatgg ccatggaacc agacagaaaa gcggctgtta gtcactggca    60
gcaacagtct tacctggact ctggaatcca ttctggtgcc actaccacag ctccttytct    120
gagtggtaaa ggcaatcctg aggaagagga tgtggatacc tcccaagtcc tgtatgagtg    180
ggaa                                                                184
```

<210> SEQ ID NO 10
<211> LENGTH: 181

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gtggacaacc cccacgtgtg ccgcctgctg ggcatctgcc tcacctccac cgtgcagctc    60
atcaygcagc tcatgccctt cggctgcctc ctggactatg tccgggaaca caaagacaat   120
attggctccc agtacctgct caactggtgt gtgcagatcg caaaggtaat cagggaaggg   180
a                                                                   181

<210> SEQ ID NO 11
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gcatgaacta cttggaggac cgtcgcttgg tgcaccgcga cctggcagcc aggaacgtac    60
tggtgaaaac accgcagcat gtcaagatca cagattttgg gckggccaaa ctgctgggtg   120
cggaagagaa agaataccat gcagaaggag gcaaagtaag gaggtg                  166

<210> SEQ ID NO 12
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggattcct acaggaagca agtagtaatt gatggagaaa cctgtctctt ggatattctc    60
gacacagsag gtcaagagga gtacagtgca atgagggacc agtacatgag gactggggag   120
ggctttcttt gtgtatttgc cataaataat actaaatcat ttgaagatat tc           172

<210> SEQ ID NO 13
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
acaggaagca agtagtaatt gatggagaaa cctgtctctt ggatattctc gacacagcag    60
gtcamgagga gtacagtgca atgagggacc agtacatgag gactggggag ggctttcttt   120
gtgtatttgc cataaataat actaaatcat ttgaagatat tcaccattat aggtgggttt   180
aaattgaata taataagctg acattaa                                       207

<210> SEQ ID NO 14
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
tattaacctt atgtgtgaca tgttctaata tagtcacatt ttcattattt ttattataag    60
gcctgctgaa aatgactgaa tataaacttg tggtagttgg agctrgtggc gtaggcaaga   120
gtgccttgac gatacagcta attcagaatc attttgtgga cgaatatga              169

<210> SEQ ID NO 15
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tattaacctt atgtgtgaca tgttctaata tagtcacatt ttcattattt ttattataag    60
gcctgctgaa aatgactgaa tataaacttg tggtagttgg agctgrtggc gtaggcaaga   120
gtgccttgac gatacagcta attcagaatc attttgtgga cgaatatgat c           171

<210> SEQ ID NO 16
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cattattttt attataaggc ctgctgaaaa tgactgaata taaacttgtg gtagttggag    60
ctggtgrcgt aggcaagagt gccttgacga tacagctaat tcagaatcat tttgtggacg   120
aatatgatcc aacaatagag gtaaatcttg ttttaatatg catattactg gtgcaggacc   180
attctttgat acagataaag gtttctctga ccatttttcat gagtacttat             230

<210> SEQ ID NO 17
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
attcttacag aaaacaagtg gttatagatg gtgaaacctg tttgttggac atactggata    60
cagctggama agaagagtac agtgccatga gagaccaata catgaggaca ggcgaaggct   120
tcctctgtgt atttgccatc aataatagca agtcatttgc ggatattaac ctctacaggt   180
actaggagca ttattttctc tgaaaggatg                                    210

<210> SEQ ID NO 18
<211> LENGTH: 206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ttacagaaaa caagtggtta tagatggtga aacctgtttg ttggacatac tggatacagc    60
tggacawgaa gagtacagtg ccatgagaga ccaatacatg aggacaggcg aaggcttcct   120
ctgtgtattt gccatcaata atagcaagtc atttgcggat attaacctct acaggtacta   180
```

```
ggagcattat tttctctgaa aggatg                                         206
```

<210> SEQ ID NO 19
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
tggtttccaa caggttcttg ctggtgtgaa atgactgagt acaaactggt ggtggttgga    60
gcagrtggtg ttgggaaaag cgcactgaca atccagctaa tccagaacca ctttgtagat   120
gaatatgatc ccaccataga ggtgaggccc agtggtagcc cg                      162
```

<210> SEQ ID NO 20
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
tttccaacag gttcttgctg gtgtgaaatg actgagtaca aactggtggt ggttggagca    60
ggtgrtgttg ggaaaagcgc actgacaatc cagctaatcc agaaccactt tgtagatgaa   120
tatgatccca ccatagaggt gaggcccagt ggtagccc                           158
```

<210> SEQ ID NO 21
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
ggcacccgcg tccgcgccat ggccatctac aagcagtcac agcacatgac ggaggttgtg    60
aggcrctgcc cccaccatga gcgctgctca gatagcgatg tgagcagct ggggctggag    120 agacgacagg gctggttgcc cagggtcccc aggcctctga ttcctcactg attgctctta   180
ggtctggcc                                                           189
```

<210> SEQ ID NO 22
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
cctcctcagc atcttatccg agtggaagga aatttgcgtg tggagtattt ggatgacaga    60
aacactttty gacatagtgt ggtggtgccc tatgagccgc ctgaggtctg gtttgcaact   120
ggggtctctg ggaggagggg ttaagggtgg ttgtcagtgg ccctc                   165
```

<210> SEQ ID NO 23
<211> LENGTH: 183
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
cttgggcctg tgttatctcc taggttggct ctgactgtac caccatccac tacaactaca     60
tgtgtaacag tkcctgcatg ggcggcatga accggaggcc catcctcacc atcatcacac    120
tggaagactc caggtcagga gccacttgcc accctgcaca ctggcctgct gtgcccagc     180 ctc                                                                   183

<210> SEQ ID NO 24
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
taggttggct ctgactgtac caccatccac tacaactaca tgtgtaacag ttcctgcatg     60
ggcrgcatga accggaggcc catcctcacc atcatcacac tggaagactc caggtcagga   120
gccacttgcc accctgcaca ctggcctgct gtgcccagc ctc                       163

<210> SEQ ID NO 25
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ctgactgtac caccatccac tacaactaca tgtgtaacag ttcctgcatg ggcggcatga     60
acyggaggcc catcctcacc atcatcacac tggaagactc caggtcagga gccacttgcc   120
accctgcaca ctggcctgct gtgcccagc ctctgcttgc ctc                       163

<210> SEQ ID NO 26
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tgactgtacc accatccact acaactacat gtgtaacagt tcctgcatgg gcggcatgaa     60
ccrgaggccc atcctcacca tcatcacact ggaagactcc aggtcaggag ccacttgcca   120
ccctgcacac tggcctgctg tgcccagcc tctgcttgcc tc                        162

<210> SEQ ID NO 27
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cctcttgctt ctcttttcct atcctgagta gtggtaatct actgggacgg aacagctttg     60
aggtgygtgt ttgtgcctgt cctggggagag accggcgcac agaggaagag aatctccgca   120
agaaagggga gcctcaccac gagctgcccc cagggagcac taagcgaggt aagcaa        176

<210> SEQ ID NO 28
<211> LENGTH: 601
<212> TYPE: DNA
<213> ORGANISM: Homo sapiens

<400> SEQUENCE: 28

```
agaaataac taagggaagg aggaaagtgg ggaggaagga agaacagtgt gaagacaatg      60
gcctgaaaac tgaaaaagtc tgttaaagtt aattatcagt ttttgagtcc aagaactggc    120
tttgctactt tctgtaagtt tctaatttac tgaataagca tgaaaaagat tgctttgagg    180
aatggttata aacacattct tagagcatag taagcagtag ggagtaacaa ataacactg     240
attagaatac tttactctac ttaattaatc aatcatattt agtttgactc accttcccag    300
haccttctag ttctttctta tctttcagtg cttgtccaga caacattttc atttcaacaa    360
ctcctgctat tgcaatgatg ggtacaattg ctaagagtaa cagtgttagt tgccaaccat    420
agatgaagga tataattatt cctgtcccaa gatttgctat attctgggta attacagcaa    480
gcctggaacc tatagcctgc aaaacaaaac aaattagaga aattttaaaa atattatctt    540
cacaactcat gcttctattt tctgaaaact caccttcatg agactatatt cattattta    600
t                                                                    601
```

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
atatttagtt tgactcacct tcccagc                                         27
```

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
accactcacc tttcccagc                                                  19
```

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
atatttagtt tgactcacct tcccaga                                         27
```

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 32
accactcacc tttcccaga                                                  19

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atatttagtt tgactcacct tcccagt                                         27

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
accactcacc tttcccagt                                                  19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
tggacaagca ctgaaaga                                                   18

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcaggagttg ttgaaatgaa aatgttg                                         27

<210> SEQ ID NO 37
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
tgactgaata taaacttgtg gtagttggag ctgstggcgt aggcaagagt gccttgacga     60
tacagctaat tcagaatcat tttgtggacg aatatgatcc aacaatagag gtaaatcttg    120
ttttaatatg catattactg gtgcaggacc attctttgat aca                      163

<210> SEQ ID NO 38
<211> LENGTH: 163
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 38
tgactgaata taaacttgtg gtagttggag ctsgtggcgt aggcaagagt gccttgacga    60
tacagctaat tcagaatcat tttgtggacg aatatgatcc aacaatagag gtaaatcttg   120
ttttaatatg catattactg gtgcaggacc attctttgat aca                     163

<210> SEQ ID NO 39
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
tgactgaata taaacttgtg gtagttggag ctgrtggcgt aggcaagagt gccttgacga    60
tacagctaat tcagaatcat tttgtggacg aatatgatcc aacaatagag gtaaatcttg   120
ttttaatatg catattactg gtgcaggacc attctttgat aca                     163

<210> SEQ ID NO 40
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
tgactgaata taaacttgtg gtagttggag ctrgtggcgt aggcaagagt gccttgacga    60
tacagctaat tcagaatcat tttgtggacg aatatgatcc aacaatagag gtaaatcttg   120
ttttaatatg catattactg gtgcaggacc attctttgat aca                     163

<210> SEQ ID NO 41
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
tgactgaata taaacttgtg gtagttggag ctggtgrcgt aggcaagagt gccttgacga    60
tacagctaat tcagaatcat tttgtggacg aatatgatcc aacaatagag gtaaatcttg   120
ttttaatatg catattactg gtgcaggacc attctttgat aca                     163

<210> SEQ ID NO 42
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (34)..(35)
<223> OTHER INFORMATION: a, c, t, g, unknown or other

<400> SEQUENCE: 42
gtgagtttgt attaaaaggt actggtggag tatnngatag tgtattaacc ttatgtgtga    60

```
catgttctaa tatagtcaca ttttcattat ttttattata aggcctgctg aaaatgactg      120
aatataaact tgtggtagtt ggagctkgtg gcgtaggcaa gagt                       164
```

<210> SEQ ID NO 43
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atatttcttc atgaagacct cacagtaaaa ataggtgatt ttggtctagc tacagwgaaa      60
tctcgatgga gtgggtccca tcagtttgaa cagttgtctg gatccatttt g              111
```

<210> SEQ ID NO 44
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other

<400> SEQUENCE: 44

```
gtatccacat cctcttcctc aggattgcct ttaccactca gagaaggagc tgtggragtg      60
gcaccagaat ggattncaga gtncaggtaa gactgttgct gccagtgact a              111
```

<210> SEQ ID NO 45
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other

<400> SEQUENCE: 45

```
caggacttgg gaggtatcca catcctcttc ctcaggattg cctttaccac tcagayaagg      60
agctgtggta gtggcaccag aatggattnc agagtncagg taagactgtt g              111
```

<210> SEQ ID NO 46
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
cccacgtgtg ccgcctgctg ggcatctgcc tcacctccac cgtgcagctc atcaygcagc      60
tcatgccctt cggctgcctc ctggactatg tccgggaaca caaagacaat a              111
```

<210> SEQ ID NO 47
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
ttactttgcc tccttctgca tggtattctt tctcttccgc acccagcagt ttggcckgcc      60
caaaatctgt gatcttgaca tgctgcggtg ttttcaccag tacgttcctg g              111

<210> SEQ ID NO 48
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (63)..(63)
<223> OTHER INFORMATION: a, c, t, g, unknown or other

<400> SEQUENCE: 48
aggaagcaag tagtaattga tggagaaacc tgtctcttgg atattctcga cacagsaggt      60
cangaggagt acagtgcaat gagggaccag tacatgagga ctggggaggg c              111

<210> SEQ ID NO 49
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aagtagtaat tgatggagaa acctgtctct tggatattct cgacacagca ggtcamgagg      60
agtacagtgc aatgagggac cagtacatga ggactgggga gggctttctt t              111

<210> SEQ ID NO 50
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
ccacaaaatg attctgaatt agctgtatcg tcaaggcact cttgcctacg ccacragctc      60
caactaccac aagtttatat tcagtcattt tcagcaggcc ttataataaa a              111

<210> SEQ ID NO 51
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
tccacaaaat gattctgaat tagctgtatc gtcaaggcac tcttgcctac gccarcagct      60
ccaactacca caagtttata ttcagtcatt ttcagcaggc cttataataa a               111

<210> SEQ ID NO 52
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
attataaggc ctgctgaaaa tgactgaata taaacttgtg gtagttggag ctggtgrcgt     60
aggcaagagt gccttgacga tacagctaat tcagaatcat tttgtggacg a             111

<210> SEQ ID NO 53
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
aacaagtggt tatagatggt gaaacctgtt tgttggacat actggataca gctggamaag     60
aagagtacag tgccatgaga gaccaataca tgaggacagg cgaaggcttc c              111

<210> SEQ ID NO 54
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caagtggtta tagatggtga aacctgtttg ttggacatac tggatacagc tggacawgaa     60
gagtacagtg ccatgagaga ccaatacatg aggacaggcg aaggcttcct c              111

<210> SEQ ID NO 55
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atatttcttc atgaagacct cacagtaaaa ataggtgatt ttggtctagc tacagwgaaa     60
tctcgatgga gtgggtccca tcagtttgaa cagttgtctg gatccatttt g              111

<210> SEQ ID NO 56
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other

<400> SEQUENCE: 56

```
gtatccacat cctcttcctc aggattgcct ttaccactca gagaaggagc tgtggragtg    60
gcaccagaat ggattncaga gtncaggtaa gactgttgct gccagtgact a            111
```

<210> SEQ ID NO 57
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other

<400> SEQUENCE: 57

```
caggacttgg gaggtatcca catcctcttc ctcaggattg cctttaccac tcagayaagg    60
agctgtggta gtggcaccag aatggattnc agagtncagg taagactgtt g            111
```

<210> SEQ ID NO 58
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
cccacgtgtg ccgcctgctg ggcatctgcc tcacctccac cgtgcagctc atcaygcagc    60
tcatgccctt cggctgcctc ctggactatg tccgggaaca caaagacaat a             111
```

<210> SEQ ID NO 59
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
ttactttgcc tccttctgca tggtattctt tctcttccgc acccagcagt ttggcckgcc    60
caaaatctgt gatcttgaca tgctgcggtg ttttcaccag tacgttcctg g             111
```

<210> SEQ ID NO 60
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (63)..(63)
<223> OTHER INFORMATION: a, c, t, g, unknown or other

<400> SEQUENCE: 60

```
aggaagcaag tagtaattga tggagaaacc tgtctcttgg atattctcga cacagsaggt    60
cangaggagt acagtgcaat gagggaccag tacatgagga ctggggaggg c             111
```

<210> SEQ ID NO 61

<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
aagtagtaat tgatggagaa acctgtctct tggatattct cgacacagca ggtcasgagg    60
agtacagtgc aatgagggac cagtacatga ggactgggga gggctttctt t            111

<210> SEQ ID NO 62
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ccacaaaatg attctgaatt agctgtatcg tcaaggcact cttgcctacg ccacragctc    60
caactaccac aagtttatat tcagtcattt tcagcaggcc ttataataaa a             111

<210> SEQ ID NO 63
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
tccacaaaat gattctgaat tagctgtatc gtcaaggcac tcttgcctac gccarcagct    60
ccaactacca caagtttata ttcagtcatt ttcagcaggc cttataataa a             111

<210> SEQ ID NO 64
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
attataaggc ctgctgaaaa tgactgaata taaacttgtg gtagttggag ctggtgrcgt    60
aggcaagagt gccttgacga tacagctaat tcagaatcat tttgtggacg a             111

<210> SEQ ID NO 65
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
aacaagtggt tatagatggt gaaacctgtt tgttggacat actggataca gctggamaag    60
aagagtacag tgccatgaga gaccaataca tgaggacagg cgaaggcttc c             111

<210> SEQ ID NO 66
<211> LENGTH: 111
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 66
caagtggtta tagatggtga aacctgtttg ttggacatac tggatacagc tggacawgaa      60
gagtacagtg ccatgagaga ccaatacatg aggacaggcg aaggcttcct c              111

<210> SEQ ID NO 67
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atatttcttc atgaagacct cacagtaaaa ataggtgatt ttggtctagc tacagwgaaa      60
tctcgatgga gtgggtccca tcagtttgaa cagttgtctg gatccatttt g              111

<210> SEQ ID NO 68
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other

<400> SEQUENCE: 68
gtatccacat cctcttcctc aggattgcct ttaccactca gagaaggagc tgtggragtg      60
gcaccagaat ggattncaga gtncaggtaa gactgttgct gccagtgact a              111

<210> SEQ ID NO 69
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other

<400> SEQUENCE: 69
caggacttgg gaggtatcca catcctcttc ctcaggattg cctttaccac tcagayaagg      60
agctgtggta gtggcaccag aatggattnc agagtncagg taagactgtt g              111

<210> SEQ ID NO 70
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
cccacgtgtg ccgcctgctg ggcatctgcc tcacctccac cgtgcagctc atcaygcagc    60
tcatgccctt cggctgcctc ctggactatg tccgggaaca caaagacaat a             111

<210> SEQ ID NO 71
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
ttactttgcc tccttctgca tggtattctt tctcttccgc acccagcagt ttggccygcc    60
caaaatctgt gatcttgaca tgctgcggtg ttttcaccag tacgttcctg g             111

<210> SEQ ID NO 72
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (63)..(63)
<223> OTHER INFORMATION: a, c, t, g, unknown or other

<400> SEQUENCE: 72
aggaagcaag tagtaattga tggagaaacc tgtctcttgg atattctcga cacagkaggt    60
cangaggagt acagtgcaat gagggaccag tacatgagga ctggggaggg c             111

<210> SEQ ID NO 73
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
aagtagtaat tgatggagaa acctgtctct tggatattct cgacacagca ggtcamgagg    60
agtacagtgc aatgagggac cagtacatga ggactgggga gggctttctt t             111

<210> SEQ ID NO 74
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
ccacaaaatg attctgaatt agctgtatcg tcaaggcact cttgcctacg ccacragctc    60
caactaccac aagtttatat tcagtcattt tcagcaggcc ttataataaa a             111

<210> SEQ ID NO 75
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
tccacaaaat gattctgaat tagctgtatc gtcaaggcac tcttgcctac gccarcagct    60
ccaactacca caagtttata ttcagtcatt ttcagcaggc cttataataa a             111

<210> SEQ ID NO 76
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
attataaggc ctgctgaaaa tgactgaata taaacttgtg gtagttggag ctggtgrcgt    60
aggcaagagt gccttgacga tacagctaat tcagaatcat tttgtggacg a             111

<210> SEQ ID NO 77
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
aacaagtggt tatagatggt gaaacctgtt tgttggacat actggataca gctggamaag    60
aagagtacag tgccatgaga gaccaataca tgaggacagg cgaaggcttc c             111

<210> SEQ ID NO 78
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
caagtggtta tagatggtga aacctgtttg ttggacatac tggatacagc tggacawgaa    60
gagtacagtg ccatgagaga ccaatacatg aggacaggcg aaggcttcct c             111

<210> SEQ ID NO 79
<211> LENGTH: 290
<212> TYPE: DNA
<213> ORGANISM: Homo sapiens

<400> SEQUENCE: 79
gtactggtgg agtatttgat agtgtattaa ccttatgtgt gacatgttct aatatagtca    60
cattttcatt atttttatta taaggcctgc tgaaaatgac tgaatataaa cttgtggtag    120
ttggagctgg tggcgtaggc aagagtgcct tgacgataca gctaattcag aatcattttg    180
tggacgaata tgatccaaca atagaggtaa atcttgtttt aatatgcata ttactggtgc    240
aggaccattc tttgatacag ataaaggttt ctctgaccat tttcatgagt              290

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cccgctgctc ctgtgc                                        16

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acccaacgca caacttagcg                                    20

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cccgccttga tggatggaga tttac                              25

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcacccttgg tgaaacaatt gttg                               24

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgccgaactg gaagtatttt gacag                              25

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tatccctcac agagagaagg gag                                23

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gcttgcaatg gctccaacc                                         19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggagccattg caagccaag                                         19

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tggcaagagc gatgagtact c                                      21

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctctcaaaag gtaactgccc actta                                  25

<210> SEQ ID NO 90
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
ctcctgtgct gtcacc                                            16

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
cttagcggca cgcac                                             15

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
ggagatttac gcaatgtg                                          18

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
acaattgttg agggggg                                                17

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
aagtattttg acagctttac                                             20

<210> SEQ ID NO 95
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cccggctgct cctgtgt                                                17

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gccgaacgca caacttagca                                             20

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cccgccttga tggatggaga tttat                                       25

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tgcacccttg gtgaaacaat tgttc                                       25

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgccgaactg gaagtatttt gacat                                        25

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
atggccctga taagggaga                                               19

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
agggcggtgc tcgag                                                   15

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
tgtcactcta cccagtaaa                                               19

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
agaatctgcc aattacctag a                                            21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
acaagtagct gataataaat g                                            21

```
<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
gctcctgtgt tgtcacc                                                       17

<210> SEQ ID NO 106
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
cttagcagca cgcacc                                                        16

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
tggagattta tgcaatgtg                                                     19

<210> SEQ ID NO 108
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
acaattgttc aggggggg                                                      17

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
aagtattttg acatctttac                                                    20

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gcctgatttt ggtctagcta caga                                               24

<210> SEQ ID NO 111
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgcgagaagg agctgtggt                                                    19

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ccgtgccttt accactcaga g                                                 21

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gcgcgtgcag ctcatcac                                                     18

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cggcagcagt ttggccc                                                      17

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gccggatatt ctcgacacag c                                                 21

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcggacacag caggtcaa                                                     18

<210> SEQ ID NO 117
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gcggacacag caggtcaa                                                  18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cgccttgcct acgccact                                                  18

<210> SEQ ID NO 119
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cgctgcctac gccacg                                                    16

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gcgttgccta cgccacc                                                   17

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cgcctcttgc ctacgccat                                                 19

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gcgtcttgcc tacgccag                                                  18

<210> SEQ ID NO 123
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 123
gcgtcttgcc tacgccac                                                   18

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
cgcgtagttg gagctggtga                                                 20

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ccgatactgg atacagctgg aa                                              22

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ccgtggatac agctggacaa                                                 20

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
ccgggtggtt ggagcaga                                                   18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ccggguugga gcaggtga                                                   18

<210> SEQ ID NO 129
<211> LENGTH: 18
<212> TYPE: DNA
<213> ORGANISM: Artificial Sequence
```

-continued

<220> FEATURE:
<223> OTHER INFORMATION: Description of Artificial Sequence: Synthetic
      primer

<400> SEQUENCE: 129
ccgggaggtt gtgaggca                                                      18

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gccggatgac agaaacactt ttc                                                23

<210> SEQ ID NO 131
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gcgtacaact acatgtgtaa cagtg                                              25

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gccttcctgc atgggca                                                       17

<210> SEQ ID NO 133
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gccggcggca tgaacc                                                        16

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gccgcggcat gaacca                                                        16

<210> SEQ ID NO 135
<211> LENGTH: 22
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 135
gccgccaaca gctttgaggt gc                                              22

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ccggattttg gtctagctac agt                                             23

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gccagaagga gctgtggc                                                   18

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ccgtgccttt accactcaga a                                               21

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gcgcgtgcag ctcatcat                                                   18

<210> SEQ ID NO 140
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cggcagcagt ttggcca                                                    17

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 141
cgctggatat tctcgacaca gg                                            22

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gcggacacag caggtcac                                                 18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcggacacag caggtcat                                                 18

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gcgttgccta cgccacc                                                  17

<210> SEQ ID NO 145
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gcgttgccta cgccacc                                                  17

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgttgccta cgccaca                                                  17

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 147
gcgtcttgcc tacgccac                                              18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcgtcttgcc tacgccac                                              18

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gcgtcttgcc tacgccaa                                              18

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gcctagttgg agctggtgg                                             19

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ccgatactgg atacagctgg ac                                         22

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cgcctggata cagctggaca t                                          21

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 153
cgcgtggttg gagcagg                                                    17

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cgcgttggag caggtgg                                                    17

<210> SEQ ID NO 155
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ggcgaggttg tgaggcg                                                    17

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gcctggatga cagaaacact tttt                                            24

<210> SEQ ID NO 157
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ggcctacaac tacatgtgta acagtt                                          26

<210> SEQ ID NO 158
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gcctcctgca tgggcg                                                     16

<210> SEQ ID NO 159
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
```
gccggcggca tgaact                                              16

<210> SEQ ID NO 160
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gccgcggcat gaaccg                                              16

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
cgcgaacagc tttgaggtgt                                          20

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
cccgtggtct agctacaga                                           19

<210> SEQ ID NO 163
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccccaaggag ctgtggt                                             17

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cgccccttta ccactcagag                                          20

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165

```
ggggatgcag ctcatcac                                                   18
```

<210> SEQ ID NO 166
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166

```
ggcgcagttt ggccc                                                      15
```

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167

```
cccgattctc gacacagc                                                   18
```

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
cgcccacagc aggtcaa                                                    17
```

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169

```
tgcccacagc aggtcaa                                                    17
```

<210> SEQ ID NO 170
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170

```
gccgcctacg ccact                                                      15
```

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171

```
agcccctacg ccacg                                                      15
```

<210> SEQ ID NO 172
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 172
accccctacg ccacc                                                15

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 173
ggctgcctac gccat                                                15

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 174
gggctgccta cgccag                                               16

<210> SEQ ID NO 175
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 175
ggctgcctac gccac                                                15

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
ccccgttgga gctggtga                                             18

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
cgggtggata cagctggaa                                            19

```
<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gggcgataca gctggacaa                                                    19

<210> SEQ ID NO 179
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gccctggttg gagcaga                                                      17

<210> SEQ ID NO 180
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
cccgttggag caggtga                                                      17

<210> SEQ ID NO 181
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gccaggttgt gaggca                                                       16

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tgccctgaca gaaacacttt tc                                                22

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cgccctacat gtgtaacagt g                                                 21
```

```
<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccgcctgcat gggca                                                          15

<210> SEQ ID NO 185
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cccgcggcat gaacc                                                          15

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ccccggcatg aacca                                                          15

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
cgccagcttt gaggtgc                                                        17

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
cccgtggtct agctacagt                                                      19

<210> SEQ ID NO 189
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ccccaggagc tgtggc                                                         16

<210> SEQ ID NO 190
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cgccccttta ccactcagaa                                                20

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ggggagtgca gctcatcat                                                 19

<210> SEQ ID NO 192
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ggcgcagttt ggcca                                                     15

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
cccgattctc gacacagg                                                  18

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
tgcccacagc aggtcac                                                   17

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cgcccacagc aggtcat                                                   17

<210> SEQ ID NO 196
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196 gccccctacgc cacc                                                        14

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
agcccctacg ccacc                                                        15

<210> SEQ ID NO 198
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
accgcctacg ccaca                                                        15

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
gggctgccta cgccac                                                       16

<210> SEQ ID NO 200
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ggctgcctac gccac                                                        15

<210> SEQ ID NO 201
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
gggctgccta cgccaa                                                       16

<210> SEQ ID NO 202
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 202
ccccttggag ctggtgg                                                    17

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203 cggggatac agctggac                                                    18

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gggcgataca gctggacat                                                  19

<210> SEQ ID NO 205
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
gcccggttgg agcagg                                                     16

<210> SEQ ID NO 206
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
cccttggagc aggtgg                                                     16

<210> SEQ ID NO 207
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gccaggttgt gaggcg                                                     16

<210> SEQ ID NO 208
<211> LENGTH: 22
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 208
tgccctgaca gaaacactt tt                                          22

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
cgccctacat gtgtaacagt t                                          21

<210> SEQ ID NO 210
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
ccgctgcatg ggcg                                                  14

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
cccgcggcat gaact                                                 15

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ccccggcatg aaccg                                                 15

<210> SEQ ID NO 213
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
cgccagcttt gaggtgt                                               17

<210> SEQ ID NO 214
<211> LENGTH: 26
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 214
agcctcaatt cttaccatcc acaaaa                                          26

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
catggaacca gacagaaaag cg                                              22

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
gtcactggca gcaacagtct ta                                              22

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tgggagccaa tattgtcttt gtgtt                                           25

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
aggaacgtac tggtgaaaac acc                                             23

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ccctccccag tcctcatgta                                                 20

<210> SEQ ID NO 220
<211> LENGTH: 41
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 220
tcttcaaatg atttagtatt atttatggca aatacacaaa g                           41

<210> SEQ ID NO 221
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tcttcaaatg atttagtatt atttatggca aatacacaaa g                           41

<210> SEQ ID NO 222
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tgtgtgacat gttctaatat agtcacat                                          28

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
tgtgtgacat gttctaatat agtcacat                                          28

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tgtgtgacat gttctaatat agtcacat                                          28

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tgtgtgacat gttctaatat agtcacat                                          28

<210> SEQ ID NO 226
<211> LENGTH: 28
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 226
tgtgtgacat gttctaatat agtcacat                                              28

<210> SEQ ID NO 227
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tgtgtgacat gttctaatat agtcacat                                              28

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
ggtcctgcac cagtaatatg ca                                                    22

<210> SEQ ID NO 229
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gcaaatgact tgctattatt gatggcaaa                                             29

<210> SEQ ID NO 230
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gcaaatgact tgctattatt gatggcaaa                                             29

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
agtggttctg gattagctgg attg                                                  24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 232
gtggttctgg attagctgga ttgt                                              24

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
gcaaccagcc ctgtcgtc                                                     18

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234 agacccagt tgcaaaccag                                                    20

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ctggagtctt ccagtgtgat gatg                                              24

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ctggagtctt ccagtgtgat gat                                               23

<210> SEQ ID NO 237
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgtgcagggt ggcaagt                                                      17

<210> SEQ ID NO 238
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
```
tgtgcagggt ggcaagt                                      17

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ctttcttgcg gagattctct tcct                              24

<210> SEQ ID NO 240
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
cagacaactg ttcaaactg                                    19

<210> SEQ ID NO 241
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
ctggcagcaa cagtct                                       16

<210> SEQ ID NO 242
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
tagtggcacc agaatgg                                      17

<210> SEQ ID NO 243
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
cccttcggct gcctcc                                       16

<210> SEQ ID NO 244
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244

```
cagcatgtca agatcac                                                    17

<210> SEQ ID NO 245
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
ctggtccctc attgcac                                                    17

<210> SEQ ID NO 246
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
ccctccccag tcctca                                                     16

<210> SEQ ID NO 247
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
ccctccccag tcctca                                                     16

<210> SEQ ID NO 248
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
cctgctgaaa atgac                                                      15

<210> SEQ ID NO 249
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
cctgctgaaa atgac                                                      15

<210> SEQ ID NO 250
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
cctgctgaaa atgac                                                      15
```

<210> SEQ ID NO 251
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
cctgctgaaa atgac                                                    15

<210> SEQ ID NO 252
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
cctgctgaaa atgac                                                    15

<210> SEQ ID NO 253
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
cctgctgaaa atgac                                                    15

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
tcgtccacaa aatgattc                                                 18

<210> SEQ ID NO 255
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
ccttcgcctg tcctcatg                                                 18

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
ccttcgcctg tcctcatg                                                 18

```
<210> SEQ ID NO 257
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
cagtgcgctt ttcc                                                         14

<210> SEQ ID NO 258
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
cagtgcgctt ttcc                                                         14

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
ctgctcacca tcgctatc                                                     18

<210> SEQ ID NO 260
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
cctcaggcgg ctcatag                                                      17

<210> SEQ ID NO 261
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
atgggcctcc ggttcat                                                      17

<210> SEQ ID NO 262
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
accggaggcc catcct                                                       16
```

-continued

<210> SEQ ID NO 263
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
cacactggaa gactcc                                                         16

<210> SEQ ID NO 264
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
cacactggaa gactcc                                                         16

<210> SEQ ID NO 265
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
ctgtgcgccg gtctc                                                          15

<210> SEQ ID NO 266
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
gctacagaga aatctc                                                         16

<210> SEQ ID NO 267
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
gagctgtggt agtggca                                                        17

<210> SEQ ID NO 268
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
cactcagaga aggagc                                                         16

<210> SEQ ID NO 269

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
catcacgcag ctcatg                                                   16

<210> SEQ ID NO 270
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
agtttggccc gcccaa                                                   16

<210> SEQ ID NO 271
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
ctcgacacag caggtca                                                  17

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
gcaggtcaag aggagtac                                                 18

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
gcaggtcaag aggagtac                                                 18

<210> SEQ ID NO 274
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
cgccactagc tcca                                                     14

<210> SEQ ID NO 275
<211> LENGTH: 16
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
ccacgagctc caacta                                                            16

<210> SEQ ID NO 276
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
acgccaccag ctcc                                                              14

<210> SEQ ID NO 277
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
cgccatcagc tcc                                                               13

<210> SEQ ID NO 278
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
cgccagcagc tcc                                                               13

<210> SEQ ID NO 279
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
cgccaccagc tcca                                                              14

<210> SEQ ID NO 280
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
gctggtgacg taggc                                                             15

<210> SEQ ID NO 281
<211> LENGTH: 18
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 281
gctggaaaag aagagtac                                                    18

<210> SEQ ID NO 282
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 282
cagctggaca agaagag                                                     17

<210> SEQ ID NO 283
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
ttggagcaga tggtgtt                                                     17

<210> SEQ ID NO 284
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
tggagcaggt gatgtt                                                      16

<210> SEQ ID NO 285
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
tgaggcactg ccc                                                         13

<210> SEQ ID NO 286
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
gaaacacttt tcgacatagt gtggtg                                           26

<210> SEQ ID NO 287
<211> LENGTH: 20
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 287
tgtgtaacag tgcctgcatg                                              20

<210> SEQ ID NO 288
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 288
gcatgggcag catg                                                    14

<210> SEQ ID NO 289
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 289
gcatgaaccg gaggc                                                   15

<210> SEQ ID NO 290
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 290
catgaaccag aggcc                                                   15

<210> SEQ ID NO 291
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 291
ttgaggtgcg tgtttgtg                                                18

<210> SEQ ID NO 292
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 292
gctacagtga aatctc                                                  16

<210> SEQ ID NO 293
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 293
agctgtggca gtggca                                                    16

<210> SEQ ID NO 294
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 294
cactcagaaa aggagc                                                    16

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 295
tcatcatgca gctcatg                                                   17

<210> SEQ ID NO 296
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 296
agtttggcca gcccaa                                                    16

<210> SEQ ID NO 297
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 297
ctcgacacag gaggtca                                                   17

<210> SEQ ID NO 298
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 298
caggtcacga ggagtac                                                   17

<210> SEQ ID NO 299
<211> LENGTH: 18
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 299
gcaggtcatg aggagtac                                                       18

<210> SEQ ID NO 300
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 300
cgccaccagc tcc                                                            13

<210> SEQ ID NO 301
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 301
ccaccagctc caacta                                                         16

<210> SEQ ID NO 302
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 302
acgccacaag ctccaa                                                         16

<210> SEQ ID NO 303
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 303
cgccaccagc tcc                                                            13

<210> SEQ ID NO 304
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 304
cgccaccagc tcc                                                            13

<210> SEQ ID NO 305
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 305
cgccaacagc tccaa                                                          15

<210> SEQ ID NO 306
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 306
gctggtggcg taggc                                                          15

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 307
gctggacaag aagagtac                                                       18

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 308
cagctggaca tgaagag                                                        17

<210> SEQ ID NO 309
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 309
tggagcaggt ggtgtt                                                         16

<210> SEQ ID NO 310
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 310
tggagcaggt ggtgtt                                                         16

<210> SEQ ID NO 311
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 311
tgaggcgctg ccc                                                          13

<210> SEQ ID NO 312
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 312
agaaacactt tttgacatag tgtggtg                                           27

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 313
atgtgtaaca gttcctgcat g                                                 21

<210> SEQ ID NO 314
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 314
gcatgggcgg catg                                                         14

<210> SEQ ID NO 315
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 315
gcatgaactg gaggcc                                                       16

<210> SEQ ID NO 316
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 316
catgaaccgg aggcc                                                        15

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 317

-continued tttgaggtgt gtgtttgtgc						20

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ccctggtagt tggagctgg						19

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
cgctgtggta gttggagctg						20

<210> SEQ ID NO 320
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
gcccggtagt tggagctgg						19

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
cgccgtggta gttggagctg						20

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
ccccagttgg agctggtgg						19

<210> SEQ ID NO 323
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gccttgccta cgccaca                                              17

<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gcctcttgcc tacgccaa                                             18

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
aaagaatggt cctgcaccag taa                                       23

<210> SEQ ID NO 326
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
ggtcctgcac cagtaatatg ca                                        22

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
aaagaatggt cctgcaccag taa                                       23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
aaagaatggt cctgcaccag taa                                       23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
aaagaatggt cctgcaccag taa                                       23

-continued

```
<210> SEQ ID NO 330
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gagtttgtat taaaaggtac tggtggagt                                       29

<210> SEQ ID NO 331
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gagtttgtat taaaaggtac tggtggagt                                       29

<210> SEQ ID NO 332
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
ccctggtagt tggagctgc                                                  19

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
cgctgtggta gttggagctc                                                 20

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
gcccggtagt tggagctga                                                  19

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
cgccgtggta gttggagcta                                                 20
```

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 336
ccccagttgg agctggtga                                            19

<210> SEQ ID NO 337
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 337
gccttgccta cgccacc                                              17

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 338
gcctcttgcc tacgccac                                             18

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 339
atgcatatta aaacaagatt tac                                       23

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 340
aacaatagag gtaaatcttg                                           20

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 341
atgcatatta aaacaagatt tac                                       23

```
<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 342
atgcatatta aaacaagatt tac                                              23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 343
atgcatatta aaacaagatt tac                                              23

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 344
accttatgtg tgacatgttc                                                  20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 345
accttatgtg tgacatgttc                                                  20

<210> SEQ ID NO 346
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 346
tggagctgct ggcgta                                                      16

<210> SEQ ID NO 347
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 347
tggagctcgt ggcgta                                                      16

<210> SEQ ID NO 348
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 348
ttggagctga tggcgta                                                      17

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 349
tagttggagc tagtggcgta                                                   20

<210> SEQ ID NO 350
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 350
ttggagctgg tgacgta                                                      17

<210> SEQ ID NO 351
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 351
cgccaccagc tcca                                                         14

<210> SEQ ID NO 352
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 352
ctacgccacc agctc                                                        15

<210> SEQ ID NO 353
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 353
tggagctggt ggcgta                                                       16

<210> SEQ ID NO 354
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 354
tggagctggt ggcgta                                                    16

<210> SEQ ID NO 355
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 355
tggagctggt ggcgta                                                    16

<210> SEQ ID NO 356
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 356
tggagctggt ggcgta                                                    16

<210> SEQ ID NO 357
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 357
tggagctggt ggcgta                                                    16

<210> SEQ ID NO 358
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 358
cgccacaagc tcca                                                      14

<210> SEQ ID NO 359
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 359
tacgccaaca gctc                                                      14

<210> SEQ ID NO 360
<211> LENGTH: 21
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 360
tgattttggt ctagctacag a                                              21

<210> SEQ ID NO 361
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 361
gagaaggagc tgtggt                                                    16

<210> SEQ ID NO 362
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 362
tgcctttacc actcagag                                                  18

<210> SEQ ID NO 363
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 363
cgtgcagctc atcac                                                     15

<210> SEQ ID NO 364
<211> LENGTH: 14
<212> TYPE: DNA
<213> ORGANISM: Artificial Sequence
<220> FEATURE:
<223> OTHER INFORMATION: Description of Artificial Sequence: Synthetic primer

<400> SEQUENCE: 364
cagcagtttg gccc                                                      14

<210> SEQ ID NO 365
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 365
ggatattctc gacacagc                                                  18

<210> SEQ ID NO 366
<211> LENGTH: 15
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 366
gacacagcag gtcaa                                                      15

<210> SEQ ID NO 367
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
cttgcctacg ccact                                                      15

<210> SEQ ID NO 368
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
ctcttgccta cgccat                                                     16

<210> SEQ ID NO 369
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
gtagttggag ctggtga                                                    17

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
atactggata cagctggaa                                                  19

<210> SEQ ID NO 371
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
tggatacagc tggacaa                                                    17

<210> SEQ ID NO 372
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 372
gattttggtc tagctacagt                                              20

<210> SEQ ID NO 373
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
agaaggagct gtggc                                                   15

<210> SEQ ID NO 374
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
tgcctttacc actcagaa                                                18

<210> SEQ ID NO 375
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
cgtgcagctc atcat                                                   15

<210> SEQ ID NO 376
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
cagcagtttg gcca                                                    14

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
tggatattct cgacacagg                                               19

<210> SEQ ID NO 378
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 378
gacacagcag gtcac                                                        15

<210> SEQ ID NO 379
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
ttgcctacgc cacc                                                         14

<210> SEQ ID NO 380
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
tcttgcctac gccac                                                        15

<210> SEQ ID NO 381
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
tagttggagc tggtgg                                                       16

<210> SEQ ID NO 382
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
atactggata cagctggac                                                    19

<210> SEQ ID NO 383
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
ctggatacag ctggacat                                                     18

<210> SEQ ID NO 384
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 384
gcctgatttt ggtctagcta caga                                        24

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
cgcgagaagg agctgtggt                                              19

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
ccgtgccttt accactcaga g                                           21

<210> SEQ ID NO 387
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
gcgcgtgcag ctcatcac                                               18

<210> SEQ ID NO 388
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
cggcagcagt ttggccc                                                17

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
gccggatatt ctcgacacag c                                           21

<210> SEQ ID NO 390
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 390
gcggacacag caggtcaa                                                      18

<210> SEQ ID NO 391
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
cgccttgcct acgccact                                                      18

<210> SEQ ID NO 392
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
cgcctcttgc ctacgccat                                                     19

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
cgcgtagttg gagctggtga                                                    20

<210> SEQ ID NO 394
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
ccgatactgg atacagctgg aa                                                 22

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
ccgtggatac agctggacaa                                                    20

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
```

```
ccggattttg gtctagctac agt                                         23
```

<210> SEQ ID NO 397
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397

```
gccagaagga gctgtggc                                               18
```

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398

```
ccgtgccttt accactcaga a                                           21
```

<210> SEQ ID NO 399
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399

```
gcgcgtgcag ctcatcat                                               18
```

<210> SEQ ID NO 400
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400

```
cggcagcagt ttggcca                                                17
```

<210> SEQ ID NO 401
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401

```
cgctggatat tctcgacaca gg                                          22
```

<210> SEQ ID NO 402
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402

```
gcggacacag caggtcac                                              18
```

<210> SEQ ID NO 403
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403

```
gcgttgccta cgccacc                                               17
```

<210> SEQ ID NO 404
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404

```
gcgtcttgcc tacgccac                                              18
```

<210> SEQ ID NO 405
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405

```
gcctagttgg agctggtgg                                             19
```

<210> SEQ ID NO 406
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406

```
ccgatactgg atacagctgg ac                                         22
```

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407

```
cgcctggata cagctggaca t                                          21
```

<210> SEQ ID NO 408
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408

```
agcctcaatt cttaccatcc acaaaa                                     26
```

<210> SEQ ID NO 409
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409
catggaacca gacagaaaag cg                                              22

<210> SEQ ID NO 410
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
gtcactggca gcaacagtct ta                                              22

<210> SEQ ID NO 411
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
tgggagccaa tattgtcttt gtgtt                                           25

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
aggaacgtac tggtgaaaac acc                                             23

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
ccctccccag tcctcatgta                                                 20

<210> SEQ ID NO 414
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
tcttcaaatg atttagtatt atttatggca aatacacaaa g                         41

<210> SEQ ID NO 415
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 415
tgtgtgacat gttctaatat agtcacat                                      28

<210> SEQ ID NO 416
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 416
tgtgtgacat gttctaatat agtcacat                                      28

<210> SEQ ID NO 417
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 417
ggtcctgcac cagtaatatg ca                                            22

<210> SEQ ID NO 418
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 418
gcaaatgact tgctattatt gatggcaaa                                     29

<210> SEQ ID NO 419
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
gcaaatgact tgctattatt gatggcaaa                                     29

<210> SEQ ID NO 420
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 420
cagacaactg ttcaaactg                                                19

<210> SEQ ID NO 421
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 421
ctggcagcaa cagtct                                                   16

<210> SEQ ID NO 422
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 422
tagtggcacc agaatgg                                                  17

<210> SEQ ID NO 423
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 423
cccttcggct gcctcc                                                   16

<210> SEQ ID NO 424
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 424
cagcatgtca agatcac                                                  17

<210> SEQ ID NO 425
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 425
ctggtccctc attgcac                                                  17

<210> SEQ ID NO 426
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 426
ccctccccag tcctca                                                   16

<210> SEQ ID NO 427

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 427
cctgctgaaa atgac                                                    15

<210> SEQ ID NO 428
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 428
cctgctgaaa atgac                                                    15

<210> SEQ ID NO 429
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 429
tcgtccacaa aatgattc                                                 18

<210> SEQ ID NO 430
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 430
ccttcgcctg tcctcatg                                                 18

<210> SEQ ID NO 431
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 431
ccttcgcctg tcctcatg                                                 18

<210> SEQ ID NO 432
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 432
ctacagagaa atct                                                     14

<210> SEQ ID NO 433
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 433
ctgtggtagt ggca                                                    14

<210> SEQ ID NO 434
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 434
ctcagagaag gagc                                                    14

<210> SEQ ID NO 435
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 435
atcacgcagc tca                                                     13

<210> SEQ ID NO 436
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 436
ggcccgccca a                                                       11

<210> SEQ ID NO 437
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 437
gacacagcag gtca                                                    14

<210> SEQ ID NO 438
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 438
caggtcaaga ggagta                                                  16

<210> SEQ ID NO 439
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 439
gccactagct cca                                                           13

<210> SEQ ID NO 440
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 440
gccatcagct cc                                                            12

<210> SEQ ID NO 441
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 441
tggtgacgta ggc                                                           13

<210> SEQ ID NO 442
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 442
gctggaaaag aagag                                                         15

<210> SEQ ID NO 443
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 443
ctggacaaga agag                                                          14

<210> SEQ ID NO 444
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 444
ctacagtgaa atct                                                          14

<210> SEQ ID NO 445
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 445
tgtggcagtg gca                                                          13

<210> SEQ ID NO 446
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 446
ctcagaaaag gagc                                                         14

<210> SEQ ID NO 447
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 447
catcatgcag ctca                                                         14

<210> SEQ ID NO 448
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 448
tggccagccc aa                                                           12

<210> SEQ ID NO 449
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 449
gacacaggag gtca                                                         14

<210> SEQ ID NO 450
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 450
aggtcacgag gagta                                                        15

<210> SEQ ID NO 451
<211> LENGTH: 12
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 451
ccaccagctc ca                                                         12

<210> SEQ ID NO 452
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 452
ccaccagctc c                                                          11

<210> SEQ ID NO 453
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 453
tggtggcgta ggc                                                        13

<210> SEQ ID NO 454
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 454
ctggacaaga agag                                                       14

<210> SEQ ID NO 455
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 455
ctggacatga agag                                                       14

<210> SEQ ID NO 456
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
gtgattttgg tctagctaca ga                                              22

<210> SEQ ID NO 457
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 457
tcagagaagg agctgtggt                                                    19

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
gattgccttt accactcaga g                                                 21

<210> SEQ ID NO 459
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
caccgtgcag ctcatcac                                                     18

<210> SEQ ID NO 460
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
cacccagcag tttggccc                                                     18

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
ttggatattc tcgacacagc                                                   20

<210> SEQ ID NO 462
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
ctcgacacag caggtcaa                                                     18

<210> SEQ ID NO 463
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
actcttgcct acgccact                                                    18

<210> SEQ ID NO 464
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
cactcttgcc tacgccat                                                    18

<210> SEQ ID NO 465
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
tggtagttgg agctggtga                                                   19

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
catactggat acagctggaa                                                  20

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
atactggata cagctggaca a                                                21

<210> SEQ ID NO 468
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 468
gtgattttgg tctagctaca gt                                               22

<210> SEQ ID NO 469
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 469
tcagagaagg agctgtggc                                                  19

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
gattgccttt accactcaga a                                               21

<210> SEQ ID NO 471
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 471
caccgtgcag ctcatcat                                                   18

<210> SEQ ID NO 472
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
cacccagcag tttggcca                                                   18

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 473
cttggatatt ctcgacacag g                                               21

<210> SEQ ID NO 474
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474
tctcgacaca gcaggtcac                                                  19

<210> SEQ ID NO 475
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
```

```
actcttgcct acgccacc                                             18

<210> SEQ ID NO 476
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 476
cactcttgcc tacgccac                                             18

<210> SEQ ID NO 477
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
tggtagttgg agctggtgg                                            19

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 478
catactggat acagctggac                                           20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 479
tactggatac agctggacat                                           20

<210> SEQ ID NO 480
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 480
agcctcaatt cttaccatcc acaaaa                                    26

<210> SEQ ID NO 481
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 481
```
catggaacca gacagaaaag cg                                          22

<210> SEQ ID NO 482
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 482
gtcactggca gcaacagtct ta                                          22

<210> SEQ ID NO 483
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 483
tgggagccaa tattgtcttt gtgtt                                       25

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
aggaacgtac tggtgaaaac acc                                         23

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
ccctccccag tcctcatgta                                             20

<210> SEQ ID NO 486
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
tcttcaaatg atttagtatt atttatggca aatacacaaa g                     41

<210> SEQ ID NO 487
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
tgtgtgacat gttctaatat agtcacat                                    28

<210> SEQ ID NO 488
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
tgtgtgacat gttctaatat agtcacat                                          28

<210> SEQ ID NO 489
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
ggtcctgcac cagtaatatg ca                                                22

<210> SEQ ID NO 490
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
gcaaatgact tgctattatt gatggcaaa                                         29

<210> SEQ ID NO 491
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
gcaaatgact tgctattatt gatggcaaa                                         29

<210> SEQ ID NO 492
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 492
cagacaactg ttcaaactg                                                    19

<210> SEQ ID NO 493
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 493
ctggcagcaa cagtct                                                       16

<210> SEQ ID NO 494
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 494
tagtggcacc agaatgg                                                17

<210> SEQ ID NO 495
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 495
cccttcggct gcctcc                                                 16

<210> SEQ ID NO 496
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 496
cagcatgtca agatcac                                                17

<210> SEQ ID NO 497
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 497
ctggtccctc attgcac                                                17

<210> SEQ ID NO 498
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 498
ccctccccag tcctca                                                 16

<210> SEQ ID NO 499
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 499
cctgctgaaa atgac                                                  15

```
<210> SEQ ID NO 500
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 500
cctgctgaaa atgac                                                     15

<210> SEQ ID NO 501
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 501
tcgtccacaa aatgattc                                                  18

<210> SEQ ID NO 502
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 502
ccttcgcctg tcctcatg                                                  18

<210> SEQ ID NO 503
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 503
ccttcgcctg tcctcatg                                                  18

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 504
gctacagaga aatctcgatg g                                              21

<210> SEQ ID NO 505
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 505
gagctgtggt agtggca                                                   17

<210> SEQ ID NO 506
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 506
ttaccactca gagaaggagc                                               20

<210> SEQ ID NO 507
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 507
gctcatcacg cagctca                                                  17

<210> SEQ ID NO 508
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 508
ttggcccgcc caaaat                                                   16

<210> SEQ ID NO 509
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 509
gacacagcag gtcacgag                                                 18

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 510
cagcaggtca agaggagtac                                               20

<210> SEQ ID NO 511
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 511
ctacgccact agctccaac                                                19

<210> SEQ ID NO 512
<211> LENGTH: 16
```

-continued

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 512
ctacgccatc agctcc                                                      16

<210> SEQ ID NO 513
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 513
ctggtgacgt aggcaag                                                     17

<210> SEQ ID NO 514
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 514
ggatacagct ggaaaagaag ag                                               22

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 515
agctggacaa gaagagtaca                                                  20

<210> SEQ ID NO 516
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 516
tagctacagt gaaatctcga tg                                               22

<210> SEQ ID NO 517
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 517
gagctgtggc agtgg                                                       15

<210> SEQ ID NO 518
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 518
ttaccactca gaaaaggagc t                                                   21

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 519
cagctcatca tgcagctcat                                                     20

<210> SEQ ID NO 520
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 520
gtttggccag cccaaaatc                                                      19

<210> SEQ ID NO 521
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 521
gacacaggag gtcaggag                                                       18

<210> SEQ ID NO 522
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 522
cagcaggtca cgaggagta                                                      19

<210> SEQ ID NO 523
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 523
tacgccacca gctccaa                                                        17

<210> SEQ ID NO 524
<211> LENGTH: 16
<212> TYPE: DNA
<213> ORGANISM: Artificial Sequence
```

<220> FEATURE:
<223> OTHER INFORMATION: Description of Artificial Sequence: Synthetic
      probe

<400> SEQUENCE: 524
tacgccacca gctcca                                                      16

<210> SEQ ID NO 525
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 525
ctggtggcgt aggcaag                                                     17

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 526
atacagctgg acaagaagag t                                                21

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 527
agctggacat gaagagtaca                                                  20

<210> SEQ ID NO 528
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 528
cccctttggg tctagctaca ga                                               22

<210> SEQ ID NO 529
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 529
gcccgaagga gctgtggt                                                    18

<210> SEQ ID NO 530
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 530
cgccccttta ccactcagag                                                 20

<210> SEQ ID NO 531
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 531
gcgggtgcag ctcatcac                                                   18

<210> SEQ ID NO 532
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 532
cgggagcagt ttggccc                                                    17

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 533
gcccgatatt ctcgacacag c                                               21

<210> SEQ ID NO 534
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 534
gcggacacag caggtcaa                                                   18

<210> SEQ ID NO 535
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 535
cggtgcctac gccact                                                     16

<210> SEQ ID NO 536
<211> LENGTH: 17
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 536
cgccttgcct acgccat                                                        17

<210> SEQ ID NO 537
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 537
gcccagttgg agctggtga                                                      19

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 538
cgccactgga tacagctgga a                                                   21

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 539
ccgcggatac agctggacaa                                                     20

<210> SEQ ID NO 540
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 540 cccctttttgg tctagctaca gt                                                 22

<210> SEQ ID NO 541
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 541
gcccgaagga gctgtggc                                                       18

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 542
cgccccttta ccactcagaa                                       20

<210> SEQ ID NO 543
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 543
gcgggtgcag ctcatcat                                         18

<210> SEQ ID NO 544
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 544
cgggagcagt ttggcca                                          17

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 545
gcccgatatt ctcgacacag g                                     21

<210> SEQ ID NO 546
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 546
gcggacacag caggtcac                                         18

<210> SEQ ID NO 547
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 547
cggtgcctac gccacc                                           16

<210> SEQ ID NO 548
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 548
cgccttgcct acgccac                                                   17

<210> SEQ ID NO 549
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 549
gcccagttgg agctggtgg                                                 19

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 550
cgccactgga tacagctgga c                                              21

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 551
ccgcggatac agctggacat                                                20

<210> SEQ ID NO 552
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 552
agcctcaatt cttaccatcc acaaaa                                         26

<210> SEQ ID NO 553
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 553
catggaacca gacagaaaag cg                                             22

<210> SEQ ID NO 554
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 554
```
gtcactggca gcaacagtct ta                                          22

<210> SEQ ID NO 555
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 555
tgggagccaa tattgtctt gtgtt                                        25

<210> SEQ ID NO 556
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 556
aggaacgtac tggtgaaaac acc                                         23

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 557
ccctccccag tcctcatgta                                             20

<210> SEQ ID NO 558
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 558
tcttcaaatg atttagtatt atttatggca aatacacaaa g                     41

<210> SEQ ID NO 559
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
tgtgtgacat gttctaatat agtcacat                                    28

<210> SEQ ID NO 560
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
tgtgtgacat gttctaatat agtcacat 28

<210> SEQ ID NO 561
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
ggtcctgcac cagtaatatg ca 22

<210> SEQ ID NO 562
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
gcaaatgact tgctattatt gatggcaaa 29

<210> SEQ ID NO 563
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 563
gcaaatgact tgctattatt gatggcaaa 29

<210> SEQ ID NO 564
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 564
cagacaactg ttcaaactg 19

<210> SEQ ID NO 565
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 565
ctggcagcaa cagtct 16

<210> SEQ ID NO 566
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 566
tagtggcacc agaatgg 17

<210> SEQ ID NO 567
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 567
cccttcggct gcctcc                                                    16

<210> SEQ ID NO 568
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 568
cagcatgtca agatcac                                                   17

<210> SEQ ID NO 569
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 569
ctggtccctc attgcac                                                   17

<210> SEQ ID NO 570
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 570
ccctccccag tcctca                                                    16

<210> SEQ ID NO 571
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 571
cctgctgaaa atgac                                                     15

<210> SEQ ID NO 572
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 572
cctgctgaaa atgac                                                     15

-continued

<210> SEQ ID NO 573
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 573
tcgtccacaa aatgattc                                                    18

<210> SEQ ID NO 574
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 574
ccttcgcctg tcctcatg                                                    18

<210> SEQ ID NO 575
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 575
ccttcgcctg tcctcatg                                                    18

<210> SEQ ID NO 576
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 576
ctacagagaa atct                                                        14

<210> SEQ ID NO 577
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 577
ctgtggtagt ggca                                                        14

<210> SEQ ID NO 578
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 578
ctcagagaag gagc                                                        14

```
<210> SEQ ID NO 579
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 579
atcacgcagc tca                                                      13

<210> SEQ ID NO 580
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 580
ggcccgccca a                                                        11

<210> SEQ ID NO 581
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 581
gacacagcag gtca                                                     14

<210> SEQ ID NO 582
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 582
caggtcaaga ggagta                                                   16

<210> SEQ ID NO 583
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 583
gccactagct cca                                                      13

<210> SEQ ID NO 584
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 584
gccatcagct cc                                                       12

<210> SEQ ID NO 585
```

```
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 585
tggtgacgta ggc                                                          13

<210> SEQ ID NO 586
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 586
gctggaaaag aagag                                                        15

<210> SEQ ID NO 587
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 587
ctggacaaga agag                                                         14

<210> SEQ ID NO 588
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 588
ctacagtgaa atct                                                         14

<210> SEQ ID NO 589
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 589
tgtggcagtg gca                                                          13

<210> SEQ ID NO 590
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 590
ctcagaaaag gagc                                                         14

<210> SEQ ID NO 591
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 591
catcatgcag ctca                                                        14

<210> SEQ ID NO 592
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 592
tggccagccc aa                                                          12

<210> SEQ ID NO 593
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 593
gacacaggag gtca                                                        14

<210> SEQ ID NO 594
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 594
aggtcacgag gagta                                                       15

<210> SEQ ID NO 595
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 595
ccaccagctc ca                                                          12

<210> SEQ ID NO 596
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 596
ccaccagctc c                                                           11

<210> SEQ ID NO 597
<211> LENGTH: 13
<212> TYPE: DNA
```

<213> ORGANISM: Artificial Sequence
<220> FEATURE:
<223> OTHER INFORMATION: Description of Artificial Sequence: Synthetic probe

<400> SEQUENCE: 597
tggtggcgta ggc                                                          13

<210> SEQ ID NO 598
<211> LENGTH: 14
<212> TYPE: DNA
<213> ORGANISM: Artificial Sequence
<220> FEATURE:
<223> OTHER INFORMATION: Description of Artificial Sequence: Synthetic probe

<400> SEQUENCE: 598
ctggacaaga agag                                                         14

<210> SEQ ID NO 599
<211> LENGTH: 14
<212> TYPE: DNA
<213> ORGANISM: Artificial Sequence
<220> FEATURE:
<223> OTHER INFORMATION: Description of Artificial Sequence: Synthetic probe

<400> SEQUENCE: 599
ctggacatga agag                                                         14

<210> SEQ ID NO 600
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 600 cccctttgg tctagctaca ga                                                 22

<210> SEQ ID NO 601
<211> LENGTH: 18
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 601
gcccgaagga gctgtggu                                                     18

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 602
cgccccttta ccactcagag                                                   20

<210> SEQ ID NO 603

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
gcgggtgcag ctcatcac                                                 18

<210> SEQ ID NO 604
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 604
cgggagcagt ttggccc                                                  17

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
gcccgatatt ctcgacacag c                                             21

<210> SEQ ID NO 606
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
agcctcaatt cttaccatcc acaaaa                                        26

<210> SEQ ID NO 607
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 607
catggaacca gacagaaaag cg                                            22

<210> SEQ ID NO 608
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 608
gtcactggca gcaacagtct ta                                            22

<210> SEQ ID NO 609
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 609
tgggagccaa tattgtcttt gtgtt                                          25

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 610
aggaacgtac tggtgaaaac acc                                            23

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 611
ccctccccag tcctcatgta                                                20

<210> SEQ ID NO 612
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
ctacagagaa atct                                                      14

<210> SEQ ID NO 613
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 613
ctgtggtagt ggca                                                      14

<210> SEQ ID NO 614
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 614
ctcagagaag gagc                                                      14

<210> SEQ ID NO 615
<211> LENGTH: 13
<212> TYPE: DNA
```

<213> ORGANISM: Artificial Sequence
<220> FEATURE:
<223> OTHER INFORMATION: Description of Artificial Sequence: Synthetic probe

<400> SEQUENCE: 615
atcacgcagc tca                                                        13

<210> SEQ ID NO 616
<211> LENGTH: 11
<212> TYPE: DNA
<213> ORGANISM: Artificial Sequence
<220> FEATURE:
<223> OTHER INFORMATION: Description of Artificial Sequence: Synthetic probe

<400> SEQUENCE: 616
ggcccgccca a                                                          11

<210> SEQ ID NO 617
<211> LENGTH: 14
<212> TYPE: DNA
<213> ORGANISM: Artificial Sequence
<220> FEATURE:
<223> OTHER INFORMATION: Description of Artificial Sequence: Synthetic probe

<400> SEQUENCE: 617
gacacagcag gtca                                                       14

<210> SEQ ID NO 618
<211> LENGTH: 22
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 618 cccctttttgg tctagctaca gu                                             22

<210> SEQ ID NO 619
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 619
gcccgaagga gctgtggc                                                   18

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 620 cgcccctttta ccactcagaa                                                20

<210> SEQ ID NO 621

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 621
gcgggtgcag ctcatcau                                                       18

<210> SEQ ID NO 622
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
cgggagcagt ttggcca                                                        17

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
gcccgatatt ctcgacacag g                                                   21

<210> SEQ ID NO 624
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 624
cagacaactg ttcaaactg                                                      19

<210> SEQ ID NO 625
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 625
ctggcagcaa cagtct                                                         16

<210> SEQ ID NO 626
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 626
tagtggcacc agaatgg                                                        17
```

<210> SEQ ID NO 627
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 627
cccttcggct gcctcc                                                    16

<210> SEQ ID NO 628
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 628
cagcatgtca agatcac                                                   17

<210> SEQ ID NO 629
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 629
ctggtccctc attgcac                                                   17

<210> SEQ ID NO 630
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 630
ctacagtgaa atct                                                      14

<210> SEQ ID NO 631
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 631
tgtggcagtg gca                                                       13

<210> SEQ ID NO 632
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 632
ctcagaaaag gagc                                                      14

```
<210> SEQ ID NO 633
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 633
catcatgcag ctca                                                       14

<210> SEQ ID NO 634
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 634
tggccagccc aa                                                         12

<210> SEQ ID NO 635
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 635
gacacaggag gtca                                                       14
```

METHODS, COMPOSITIONS, AND KITS FOR DETECTING ALLELIC VARIANTS

CROSS REFERENCE TO RELATED APPLICATIONS

The present application is a continuation of U.S. application Ser. No. 12/748,329 filed Feb. 26, 2010, which is continuation-in-part of U.S. application Ser. No. 12/641,321, filed Dec. 17, 2009 and claims the benefit of priority under 35 U.S.C. 119 to U.S. Provisional Application Nos. 61/138,521, filed Dec. 17, 2008; 61/258,582, filed Nov. 5, 2009; 61/253,501, filed Oct. 20, 2009; 61/251,623, filed Oct. 14, 2009; 61/186,775, filed Jun. 12, 2009; and 61/164,230, filed Mar. 27, 2009, all of which are incorporated herein by reference in their entireties.

SEQUENCE LISTING

The instant application contains a Sequence Listing which has been submitted via EFS-Web and is hereby incorporated by reference in its entirety. Said ASCII copy, created on Jun. 24, 2010, is named LT000051CIP.txt and is 156,489 bytes in size.

BACKGROUND

Single nucleotide polymorphisms (SNPs) are the most common type of genetic diversity in the human genome, occurring at a frequency of about one SNP in 1,000 nucleotides or less in human genomic DNA (Kwok, P-Y, Ann Rev Genom Hum Genet 2001, 2: 235-258). SNPs have been implicated in genetic disorders, susceptibility to different diseases, predisposition to adverse reactions to drugs, and for use in forensic investigations. Thus, SNP (or rare mutation) detection provides great potentials in diagnosing early phase diseases, such as detecting circulating tumor cells in blood, for prenatal diagnostics, as well as for detection of disease-associated mutations in a mixed cell population.

Numerous approaches for SNP genotyping have been developed based on methods involving hybridization, ligation, or DNA polymerases (Chen, X., and Sullivan, P F, The Pharmacogeonomics Journal 2003, 3, 77-96.). For example, allele-specific polymerase chain reaction (AS-PCR) is a widely used strategy for detecting DNA sequence variation (Wu D Y, Ugozzoli L, Pal B K, Wallace R B., Proc Natl Acad Sci USA 1989; 86:2757-2760). AS-PCR, as its name implies, is a PCR-based method whereby one or both primers are designed to anneal at sites of sequence variations which allows for the ability to differentiate among different alleles of the same gene. AS-PCR exploits the fidelity of DNA polymerases, which extend primers with a mismatched 3' base at much lower efficiency, from 100 to 100,000 fold less efficient, than that with a matched 3' base (Chen, X., and Sullivan, P F, The Pharmacogeonomics Journal 2003; 3:77-96). The difficulty in extending mismatched primers results in diminished PCR amplification that can be readily detected.

The specificity and selectivity of AS-PCR, however, is largely dependent on the nature of exponential amplification of PCR which makes the decay of allele discriminating power rapid. Even though primers are designed to match a specific variant to selectively amplify only that variant, in actuality significant mismatched amplification often occurs. Moreover, the ability of AS-PCR to differentiate between allelic variants can be influenced by the type of mutation or the sequence surrounding the mutation or SNP (Ayyadevara S, Thaden J J, Shmookler Reis R J., Anal Biochem 2000; 284:11-18), the amount of allelic variants present in the sample, as well as the ratio between alternative alleles. Collectively, these factors are often responsible for the frequent appearance of false-positive results, leading many researchers to attempt to increase the reliability of AS-PCR (Orou A, Fechner B, Utermann G, Menzel H J., Hum Mutat 1995; 6:163-169)(Imyanitov E N, Buslov K G, Suspitsin E N, Kuligina E S, Belogubova E V, Grigoriev M Y, et al., Biotechniques 2002; 33:484-490)(McKinzie P B, Parsons B L. Detection of rare K-ras codon 12 mutations using allele-specific competitive blocker PCR. Mutat Res 2002; 517: 209-220)(Latorra D, Campbell K, Wolter A, Hurley J M., Hum Mutat 2003; 22:79-85).

In some cases, the selectivity of AS-PCR has been increased anywhere from detection of 1 in 10 alleles to 1 in 100,000 alleles by using SNP-based PCR primers containing locked nucleic acids (LNAs) (Latorra, D., et al., Hum Mut 2003, 2:79-85; Nakiandwe, J. et al., Plant Method 2007, 3:2) or modified bases (Koizumi, M. et al. Anal Biochem. 2005, 340:287-294). However, these base "mimics" or modifications increase the overall cost of analysis and often require extensive optimization.

Another technology involving probe hybridization methods used for discriminating allelic variations is TaqMan® genotyping. However, like AS-PCR, selectivity using this method is limited and not suitable for detecting rare (1 in ≥1,000) alleles or mutations in a mixed sample.

SUMMARY

In some embodiments, the present inventions relates generally to compositions, methods and kits for use in discriminating sequence variation between different alleles. More specifically, in some embodiments, the present invention provides for compositions, methods and kits for quantitating rare (e.g., mutant) allelic variants, such as SNPs, or nucleotide (NT) insertions or deletions, in samples comprising abundant (e.g., wild type) allelic variants with high specificity. In particular, in some embodiments, the invention relates to a highly selective method for mutation detection referred to as competitive allele-specific TaqMan PCR ("cast-PCR").

In one aspect, the present invention provides compositions for use in identifying and/or quantitating allelic variants in nucleic acid samples. Some of these compositions can comprise: (a) an allele-specific primer; (b) an allele-specific blocker probe; (c) a detector probe; and/or (d) a locus-specific primer.

In some embodiments of the compositions, the allele-specific primer comprises a target-specific portion and an allele-specific nucleotide portion. In some embodiments, the allele-specific primer may further comprise a tail. In some exemplary embodiments, the tail is located at the 5' end of the allele-specific primer. In other embodiments, the tail of the allele-specific primer has repeated guanine and cytosine residues ("GC-rich"). In some embodiments, the melting temperature ("Tm") of the entire allele-specific primer ranges from about 50° C. to 67° C. In some embodiments, the allele-specific primer concentration is between about 20-900 nM.

In some embodiments of the compositions, the allele-specific nucleotide portion of the allele-specific primer is located at the 3' terminus. In some embodiments, the selection of the allele-specific nucleotide portion of the allele-specific primer involves the use of a highly discriminating base (e.g., for detection of A/A, A/G, G/A, G/G, A/C, or C/A alleles). In some embodiments, for example when the allele to be detected involves A/G or C/T SNPs, A or G is used as the 3' allele-specific nucleotide portion of the allele-specific primer (e.g., if A or T is the target allele), or C or T is used as the 3' allele-specific nucleotide portion of the allele-specific primer (e.g., if C or G is the target allele). In other embodiments, A is used as the discriminating base at the 3' end of the allele-specific primer when detecting and/or quantifying A/T SNPs. In other embodiments, G is used as the discriminating base at the 3' end of the allele-specific primer when detecting and/or quantifying C/G SNPs.

In some embodiments of the compositions, the allele-specific blocker probe comprises a non-extendable blocker moiety at the 3' terminus. In some exemplary embodiments, the non-extendable blocker moiety is a minor groove binder (MGB). In some embodiments, the target allele position is located about 6-10, such as about 6, about 7, about 8, about 9, or about 10 nucleotides away from the non-extendable blocker moiety of the allele-specific blocker probe. In some embodiments, the allele-specific blocker probe comprises an MGB moiety at the 5' terminus. In some exemplary embodiments, the allele-specific blocker probe is not cleaved during PCR amplification. In some embodiments, the Tm of the allele-specific blocker probe ranges from about 58° C. to 66° C.

In some embodiments of the compositions, the allele-specific blocker probe and/or allele-specific primer comprise at least one modified base. In some embodiments, the modified base(s) may increase the difference in the Tm between matched and mismatched target sequences and/or decrease mismatch priming efficiency, thereby improving not only assay specificity bust also selectivity. Such modified base(s) may include, for example, 8-Aza-7-deaza-dA (ppA), 8-Aza-7-deaza-dG (ppG), 2'-Deoxypseudoisocytidine (iso dC), 5-fluoro-2'-deoxyuridine (fdU), locked nucleic acid (LNA), or 2'-O,4'-C-ethylene bridged nucleic acid (ENA) bases (also see, for example, FIG. 4B). In some embodiments the modified base is located at (a) the 3'-end, (b) the 5'-end, (c) at an internal position or at any combination of (a), (b) or (c) within the allele-specific blocker probe and/or the allele-specific primer.

In some embodiments of the compositions, the detector probe is a sequence-based or locus-specific detector probe. In other embodiments the detector probe is a 5' nuclease probe. In some exemplary embodiments, the detector probe can comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the detector probe is designed according to the methods and principles described in U.S. Pat. No. 6,727,356 (the disclosure of which is incorporated herein by reference in its entirety). In some exemplary embodiments, the detector probe is a TaqMan® probe (Applied Biosystems, Foster City).

In some embodiments of the compositions, the composition can further comprise a polymerase; deoxyribonucleotide triphosphates (dNTPs); other reagents and/or buffers suitable for amplification; and/or a template sequence or nucleic acid sample. In some embodiments, the polymerase can be a DNA polymerase. In some other embodiments, the polymerase can be thermostable, such as Taq DNA polymerase. In other embodiments, the template sequence or nucleic acid sample can be DNA, such as genomic DNA (gDNA) or complementary DNA (cDNA). In other embodiments the template sequence or nucleic acid sample can be RNA, such as messenger RNA (mRNA).

In another aspect, the present disclosure provides methods for amplifying an allele-specific sequence. Some of these methods can include one or more of the following: (a) hybridizing an allele-specific primer to a first nucleic acid molecule comprising a first allele (allele-1); (b) hybridizing an allele-specific blocker probe to a second nucleic acid molecule comprising a second allele (allele-2), wherein allele-2 corresponds to the same loci as allele-1; (c) hybridizing a detector probe to the first nucleic acid molecule; (d) hybridizing a locus-specific primer to the extension product of the allele-specific primer; and (e) PCR amplifying the first nucleic acid molecule comprising allele-1.

In another aspect, the present invention provides methods for detecting and/or quantitating an allelic variant in a pooled or mixed sample comprising other alleles. Some of these methods can include one or more of the following: (a) in a first reaction mixture hybridizing a first allele-specific primer to a first nucleic acid molecule comprising a first allele (allele-1) and in a second reaction mixture hybridizing a second allele-specific primer to a first nucleic acid molecule comprising a second allele (allele-2), wherein allele-2 corresponds to the same locus as allele-1; (b) in the first reaction mixture hybridizing a first allele-specific blocker probe to a second nucleic acid molecule comprising allele-2 and in the second reaction mixture hybridizing a second allele-specific blocker probe to a second nucleic acid molecule comprising allele-1; (c) in the first reaction mixture, hybridizing a first detector probe to the first nucleic acid molecule and in the second reaction mixture and hybridizing a second detector probe to the first nucleic acid molecule; (d) in the first reaction mixture hybridizing a first locus-specific primer to the extension product of the first allele-specific primer and in the second reaction mixture hybridizing a second locus-specific primer to the extension product of the second allele-specific primer; and (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In some embodiments of the methods, the first and/or second allele-specific primer comprises a target-specific portion and an allele-specific nucleotide portion. In some embodiments, the first and/or second allele-specific primer may further comprise a tail. In some embodiments, the Tm of the entire first and/or second allele-specific primer ranges from about 50° C. to 67° C. In some embodiments the first and/or second allele-specific primer concentration is between about 20-900 nM.

In some embodiments of the methods, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments of the methods, the tail is located at the 5'-end of the first and/or second allele-specific primer. In some embodiments, the 5' tail of the first allele-specific primer and the 5' tail of the second allele-specific primer comprise the same sequence. In other embodiments, the 5' tail of the first allele-specific primer and the 5' tail of the second allele-specific primer are the same sequence. In other embodiments, the tail of the first and/or second allele-specific primer is GC-rich.

In some embodiments of the methods, the allele-specific nucleotide portion of the first allele-specific primer is specific to a first allele (allele-1) of a SNP and the allele-specific nucleotide portion of the second allele-specific primer is specific to a second allele (allele-2) of the same SNP. In some embodiments of the methods, the allele-specific nucleotide portion of the first and/or second allele-specific primer is located at the 3'-terminus. In some embodiments, the selection of the allele-specific nucleotide portion of the first and/or second allele-specific primer involves the use of a highly discriminating base (e.g., for detection of A/A, A/G, G/A, G/G, A/C, or C/A alleles). In some embodiments, for example when the allele to be detected involves A/G or C/T SNPs, A or G is used as the 3' allele-specific nucleotide portion of the first and/or second allele-specific primer (e.g., if A or T is the major allele), or C or T is used as the 3' allele-specific nucleotide portion of the first and/or second allele-specific primer (e.g., if C or G is the major allele). In other embodiments, A is used as the discriminating base at the 3' end of the first and/or second allele-specific primer when detecting and/or quantifying A/T SNPs. In other embodiments, G is used as the discriminating base at the 3' end of the first and/or second allele-specific primer when detecting and/or quantifying C/G SNPs.

In some embodiments of the methods, the first and/or second allele-specific blocker probe comprises a non-extendable blocker moiety at the 3' terminus. In some exemplary embodiments, the non-extendable blocker moiety is an MGB. In some embodiments, the target allele position is located about 6-10, such as about 6, about 7, about 8, about 9, or about 10 nucleotides away from the non-extendable blocker moiety of the first and/or second allele-specific blocker probe. In some embodiments, the first and/or second allele-specific blocker probe comprises an MGB moiety at the 5'-terminus. In other embodiments, the first and/or second allele-specific blocker probe is not cleaved during PCR amplification. In some embodiments, the Tm of the first and/or second allele-specific blocker probe ranges from about 58° C. to 66° C.

In some embodiments of the methods, the first and/or second allele-specific blocker probe and/or the first and/or second allele-specific primer comprises at least one modified base. In some embodiments, the modified base(s) may increase the difference in the Tm between matched and mismatched target sequences and/or decrease mismatch priming efficiency, thereby improving not only assay specificity, but also selectivity. Such modified base(s) may include, for example, 8-Aza-7-deaza-dA (ppA), 8-Aza-7-deaza-dG (ppG), 2'-Deoxypseudoisocytidine (iso dC), 5-fluoro-2'-deoxyuridine (fdU), locked nucleic acid (LNA), or 2'-O,4'-C-ethylene bridged nucleic acid (ENA) bases (see also, for example, FIG. 4B). In some embodiments the modified base is located at (a) the 3'-end, (b) the 5'-end, (c) at an internal position or at any combination of (a), (b) or (c) within said first and/or second allele-specific blocker probe and/or the first and/or second allele-specific primer.

In some embodiments of the methods, the specificity of allelic discrimination is improved by the inclusion of a modified base in the first and/or second allele-specific primer and/or first, and/or second allele-specific blocker probe as compared to the use of a non-modified allelic-specific primer or blocker probe. In some embodiments, the improvement in specificity is at least 2 fold.

In some embodiments of the methods, the specificity of allelic discrimination is at least 2 fold better than the specificity of allelic discrimination using Allele-Specific PCR with a Blocking reagent (ASB-PCR) methods.

In some embodiments, the methods further comprise a 2-stage cycling protocol. In some embodiments, the number of cycles in the first stage of the 2-stage cycling protocol comprises fewer cycles than the number of cycles used in the second stage. In other embodiments, the number of cycles in the first stage is about 90% fewer cycles than the number of cycles in the second stage. In yet other embodiments, the number of cycles in the first stage is between 3-7 cycles and the number of cycles in the second stage is between 42-48 cycles.

In some embodiments, the annealing/extension temperature used during the first cycling stage of the 2-stage cycling protocol is between 1-3° C. lower than the annealing/extension temperature used during the second stage. In preferred embodiments, the annealing/extension temperature used during the first cycling stage of the 2-stage cycling protocol is between 56-59° C. and the annealing/extension temperature used during the second stage is between 60-62° C.

In some embodiments, the methods further comprise a pre-amplification step. In preferred embodiments, the pre-amplification step comprises a multiplex amplification reaction that uses at least two complete sets of allele-specific primers and locus-specific primers, wherein each set is suitable or operative for amplifying a specific polynucleotide of interest. In other embodiments, the products of the multiplex amplification reaction are divided into secondary single-plex amplification reactions, such as a cast-PCR reaction, wherein each single-plex reaction contains at least one primer set previously used in the multiplex reaction. In other embodiments, the multiplex amplification reaction further comprises a plurality of allele-specific blocker probes. In some embodiments, the multiplex amplification reaction is carried out for a number of cycles suitable to keep the reaction within the linear phase of amplification.

In some embodiments of the methods, the first and/or second detector probes are the same. In some embodiments, the first and/or second detector probes are different. In some embodiments, the first and/or second detector probe is a sequence-based or locus-specific detector probe. In other embodiments the first and/or second detector probe is a 5' nuclease probe. In some exemplary embodiments, the first and/or second detector probes comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the first and/or second detector probe is designed according to the methods and principles described in U.S. Pat. No. 6,727,356 (the disclosure of which is incorporated herein by reference in its entirety). In some exemplary embodiments, the detector probe is a TaqMan® probe.

In some embodiments of the methods, the first locus-specific primer and the second locus-specific primer comprise the same sequence. In some embodiments the first locus-specific primer and the second locus-specific primer are the same sequence.

In some embodiments of the methods, the first and/or second reaction mixtures can further comprises a polymerase; dNTPs; other reagents and/or buffers suitable for PCR amplification; and/or a template sequence or nucleic acid sample. In some embodiments, the polymerase can be a DNA polymerase. In some embodiments, the polymerase can be thermostable, such as Taq DNA polymerase. In some embodiments, the template sequence or nucleic acid sample can be DNA, such as gDNA or cDNA. In other embodiments the template sequence or nucleic acid sample can be RNA, such as mRNA.

In some embodiments of the methods, the first allele-specific blocker probe binds to the same strand or sequence as the second allele-specific primer, while the second allele-specific blocker probe binds to the same strand or sequence as the first allele-specific primer. In some embodiments, the first and/or second allele-specific blocker probes are used to reduce the amount of background signal generated from either the second allele and/or the first allele, respectively. In some embodiments, first and/or second allele-specific blocker probes are non-extendable and preferentially anneal to either the second allele or the first allele, respectively, thereby blocking the annealing of, for example, the extendable first allele-specific primer to the second allele and/or the extendable second allele-specific primer to first allele.

In some exemplary embodiments, the first allele is a rare (e.g., minor) or mutant allele. In other exemplary embodiments the second allele is an abundant (e.g., major) or wild type allele.

In another aspect, the present invention provides kits for quantitating a first allelic variant in a sample comprising a second allelic variant involving: (a) a first allele-specific primer; (b) a second allele-specific primer; (c), a first locus-specific primer; (d) a second locus-specific primer; (e) a first allele-specific blocker probe; (f) a second allele-specific blocker probe; and (g) a first locus-specific detector probe and (h) a second locus-specific detector probe.

In some embodiments of the kits, the first and/or second allele-specific primer comprises a target-specific portion and an allele-specific nucleotide portion. In some embodiments, the first and/or second allele-specific primer may further comprise a tail. In some embodiments, the Tm of the entire first and/or second allele-specific primer ranges from about 50° C. to 67° C. In some embodiments the first and/or second allele-specific primer concentrations are between about 20-900 nM.

In some embodiments of the kits, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments of the kits, the tail is located at the 5' end of the first and/or second allele-specific primer. In some embodiments, the 5' tail of the first allele-specific primer and the 5' tail of the second allele-specific primer comprise the same sequence. In other embodiments, the 5' tail of the first allele-specific primer and the 5' tail of the second allele-specific primer are the same sequence. In other embodiments, the tail of the first and/or second allele-specific primer is GC rich.

In some embodiments of the kits, the allele-specific nucleotide portion of the first allele-specific primer is specific to a first allele (allele-1) of a SNP and the allele-specific nucleotide portion of the second allele-specific primer is specific to a second allele (allele-2) of the same SNP. In some embodiments of the disclosed methods, the allele-specific nucleotide portion of the first and/or second allele-specific primer is located at the 3' terminus. In some embodiments, the selection of the allele-specific nucleotide portion of the first and/or second allele-specific primer involves the use of a highly discriminating base (e.g., for detection of A/A, A/G, G/A, G/G, A/C, or C/A alleles) (FIG. 2). In some embodiments, for example when the allele to be detected involves A/G or C/T SNPs, A or G is used as the 3' allele-specific nucleotide portion of the first and/or second allele-specific primer (e.g., if A or T is the major allele), or C or T is used as the 3' allele-specific nucleotide portion of the first and/or second allele-specific primer (e.g., if C or G is the major allele). In other embodiments, A is used as the discriminating base at the 3' end of the first and/or second allele-specific primer when detecting and/or quantifying A/T SNPs. In other embodiments, G is used as the discriminating base at the 3' end of the first and/or second allele-specific primer when detecting and/or quantifying C/G SNPs.

In some embodiments of the kits, the first and/or second allele-specific blocker probe comprises a non-extendable blocker moiety at the 3' terminus. In some exemplary embodiments, the non-extendable blocker moiety is an MGB. In some embodiments, the target allele position is located about 6-10, such as about 6, about 7, about 8, about 9, or about 10 nucleotides away from the non-extendable blocker moiety of the first and/or second allele-specific blocker probe. In some embodiments, the first and/or second allele-specific blocker probe comprises an MGB moiety at the 5' terminus. In other embodiments, the first and/or second allele-specific blocker probe is not cleaved during PCR amplification. In some embodiments, the Tm of the first and/or second allele-specific blocker probe ranges from about 58° C. to 66° C.

In some embodiments of the kits, the allele-specific blocker probe and/or the first and/or second allele-specific primer comprises at least one modified base. In some embodiments, the modified base(s) may increase the difference in the Tm between matched and mismatched target sequences and/or decrease mismatch priming efficiency, thereby improving not only assay specificity bust also selectivity. Such modified base(s) may include, for example, 8-Aza-7-deaza-dA (ppA), 8-Aza-7-deaza-dG (ppG), 2'-Deoxypseudoisocytidine (iso dC), 5-fluoro-2'-deoxyuridine (fdU), locked nucleic acid (LNA), or 2'-O,4'-C-ethylene bridged nucleic acid (ENA) bases (see also, for example, FIG. 4B). In some embodiments the modified base is located at (a) the 3'-end, (b) the 5'-end, (c) at an internal position or at any combination of (a), (b) or (c) within said first and/or second allele-specific blocker probe and/or the first and/or second allele-specific primer.

In some embodiments of the kits, the first and/or second detector probes are the same. In some embodiments of the disclosed kits the first and/or second detector probes are different. In some embodiments of the disclosed kits, the first and/or second detector probes are sequence-based or locus-specific detector probes. In other embodiments the first and/or second detector probe are 5' nuclease probes. In some exemplary embodiments, the first and/or second detector probes comprise an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the first and/or second detector probe are designed according to the methods and principles described in U.S. Pat. No. 6,727,356 (the disclosure of which is incorporated herein by reference in its entirety). In some exemplary embodiments, the detector probe is a TaqMan® probe.

In some embodiments of the kits, the first locus-specific primer and the second locus-specific primer comprise the same sequence. In some embodiments the first locus-specific primer and the second locus-specific primer are the same sequence.

In some embodiments of the kits, the first and/or second reaction mixture can further comprise a polymerase; dNTPs; other reagents and/or buffers suitable for PCR amplification; and/or a template sequence or nucleic acid sample. In some embodiments, the polymerase can be a DNA polymerase. In some other embodiments, the polymerase can be thermostable, such as Taq DNA polymerase.

In some embodiments, the compositions, methods and kits of the present invention provide high allelic discrimination specificity and selectivity. In some embodiments, the quantitative determination of specificity and/or selectivity comprises a comparison of Ct values between a first set of amplicons and a second set of amplicons. In some embodiments, selectivity is at a level whereby a single copy of a given allele in about 1 million copies of another allele or alleles can be detected.

The foregoing has described various embodiments of the invention that provide improved detection and discrimination of allelic variants using one or more of the following: (a) tailed allele-specific primers; (b) low allele-specific primer concentration; (c) allele-specific primers designed to have lower Tms; (d) allele-specific primers designed to target discriminating bases; (e) allele-specific blocker probes containing MGB, designed to prevent amplification from alternative, and potentially more abundant, allelic variants in a sample; and (f) allele-specific blocker probes and/or allele-specific primers designed to comprise modified bases in order to increase the delta Tm between matched and mismatched target sequences.

While particular embodiments employing several of the above improvements have been discussed herein, it will be apparent to the skilled artisan that depending on the nature of the sample to be examined, various combinations of the above improvements can be combined to arrive at a favorable result. Thus, for example, non-MGB blocker probes can be used with an embodiment that include methods employing allele-specific primers containing modified bases to increase delta Tm; such primers can also be designed to target discriminating bases; and the primers can be used at low primer concentrations. Accordingly, alternative embodiments based upon the present disclosure can be used to achieve a suitable level of allelic detection.

The present disclosure provides the advantage that any of the combinations of listed improvements could be utilized by a skilled artisan in a particular situation. For example, the current invention can include a method or reaction mixture that employs improvements a, c, d and f; improvements b, c, and e; or improvements It is to be understood that both the foregoing general description and the following detailed description are exemplary and explanatory only and are not restrictive of the invention, as claimed.

The accompanying drawings, which are incorporated in and constitute a part of this specification, illustrate several exemplary embodiments of the disclosure and together with the description, serve to explain certain teachings.

BRIEF DESCRIPTION OF THE DRAWINGS

The skilled artisan will understand that the drawings described below are for illustration purposes only. The drawings are not intended to limit the scope of the present teachings in any way.

FIG. 6 depicts the sequence of KRAS mutations at codons 12 and 13 that are detectable using cast-PCR methods. KRAS mutations at codons 12 and 13 are associated with resistance to cetuxima or panitumumab in metastatic colorectal cancer (Di Nicolantonio F., et al., *J Clin Oncol.* 2008; 26:5705-12). FIG. 6 discloses SEQ ID NO: 79.

FIG. 7 depicts the specificity of KRAS mutation detection using cast-PCR assays in one exemplary embodiment.

FIG. 10 depicts a number of different tumor markers (SNPs) detected in tumor samples using one exemplary embodiment of cast-PCR.

FIG. 11A-E shows a list of exemplary primers and probes used in cast-PCR assays. Nucleotides shown in lower case are the tailed portion of the primers. The nucleotide-portion of allele-specific primers (ASP) is at the 3'-most terminus of each primer and are indicated in bold. The allele positions of the blocker probes (MGB) are located at various internal positions relative to the blocker moieties, in some cases, are indicated in bold. FIG. 11A discloses 'ASP1' as SEQ ID NOS 80-84, respectively, in order of appearance, 'LSP' as SEQ ID NOS 85-89, respectively, in order of appearance, 'MGB1' as SEQ ID NOS 90-94, respectively, in order of appearance, 'ASP2' as SEQ ID NOS 95-99, respectively, in order of appearance, 'LST' as SEQ ID NOS 100-104, respectively, in order of appearance, and 'MGB2' as SEQ ID NOS 105-109, respectively, in order of appearance. FIG. 11B discloses 'ASP1' as SEQ ID NOS 110-135, respectively, in order of appearance, and 'ASP2' as SEQ ID NOS 136-161, respectively, in order of appearance. FIG. 11C discloses 'ASP1' as SEQ ID NOS 162-187, respectively, in order of appearance, and 'ASP2' as SEQ ID NOS 188-213, respectively, in order of appearance. FIG. 11D discloses 'LSP' as SEQ ID NOS 214-239, respectively, in order of appearance, and 'LST' as SEQ ID NOS 240-265, respectively, in order of appearance. FIG. 11E discloses 'MGB1' as SEQ ID NOS 266-292, respectively, in order of appearance, 'MGB2' as SEQ ID NOS 293-317, respectively, in order of appearance.

FIG. 12 depicts, in one exemplary embodiment, the specificity of allelic discrimination for samples that were pre-amplified prior to analysis by cast-PCR.

FIG. 13 depicts, in on exemplary embodiment, the specificity of allelic discrimination for cast-PCR assays performed using tailed versus non-tailed allele-specific primers.

FIG. 14 depicts, in on exemplary embodiment, the specificity of allelic discrimination for samples analyzed by cast-PCR versus samples analyzed by ASB-PCR methods.

FIG. 15 depicts, in on exemplary embodiment, the specificity of allelic discrimination for cast-PCR assays performed using MGB blocker probes or phosphate blocker probes.

FIG. 16 depicts, in one exemplary embodiment, the specificity of allelic discrimination for cast-PCR assays performed using LNA-modified allele-specific primers.

FIG. 17 compares, in one exemplary embodiment, the specificity of allelic discrimination for cast-PCR assays performed using various chemically-modified allele-specific primers.

FIGS. 18A and 18B show a list of exemplary allele-specific primers and probes used in pre-amplification and cast-PCR assays. FIG. 18A discloses 'ASP1' as SEQ ID NOS 318-324, respectively, in order of appearance, 'LSP' as SEQ ID NOS 325-331, respectively, in order of appearance, 'ASP2' as SEQ ID NOS 332-338, respectively, in order of appearance, and 'LST' as SEQ ID NOS 339-345, respectively, in order of appearance. FIG. 18B discloses 'MGB1' as SEQ ID NOS 346-352, respectively, in order of appearance, and 'MGB2' as SEQ ID NOS 353-359, respectively, in order of appearance.

FIG. 19A-D shows a list of exemplary primers and probes used in cast-PCR assays using either tailed (ASP+tail) or non-tailed (ASP−tail) allele-specific primers. (The tailed portion of the ASP+tail primers are indicated in bold.). FIG. 19A discloses 'ASP1-tail' as SEQ ID NOS 360-371, respectively, in order of appearance, and 'ASP2-tail' as SEQ ID NOS 372-383, respectively, in order of appearance. FIG. 19B discloses 'ASP1+tail' as SEQ ID NOS 384-395, respectively, in order of appearance, and 'ASP2+tail' as SEQ ID NOS 396-407, respectively, in order of appearance. FIG. 19C discloses 'LSP' as SEQ ID NOS 408-419, respectively, in order of appearance, and 'LST' as SEQ ID NOS 420-431, respectively, in order of appearance. FIG. 19D discloses 'MGB1' as SEQ ID NOS 432-443, respectively, in order of appearance, and 'MGB2' as SEQ ID NOS 444-455, respectively, in order of appearance.

FIG. 20A-C shows a list of exemplary primers and probes used in ASB-PCR. The blocker probes used in ASB-PCR comprise a phosphate group at the 3'-end of the blocker probes (PHOS). FIG. 20A discloses 'ASP1' as SEQ ID NOS 456-467, respectively, in order of appearance, and 'ASP2' as SEQ ID NOS 468-479, respectively, in order of appearance. FIG. 20B discloses 'LSP' as SEQ ID NOS 480-491, respectively, in order of appearance, and 'LST' as SEQ ID NOS 492-503, respectively, in order of appearance. FIG. 20C discloses 'PHOS1' as SEQ ID NOS 504-515, respectively, in order of appearance, and 'PHOS2' as SEQ ID NOS 516-527, respectively, in order of appearance.

FIG. 21A-C shows a list of exemplary primers and probes used in cast-PCR assays performed using LNA-modified allele-specific primers. In this exemplary embodiment, the LNA modifications of the ASP are at the 3'-ends. ("+" indicates the LNA modified nucleotide and are notated in parentheses.) FIG. 21A discloses 'ASP1' as SEQ ID NOS 528-539, respectively, in order of appearance, and 'ASP2' as SEQ ID NOS 540-551, respectively, in order of appearance. FIG. 21B discloses 'LSP' as SEQ ID NOS 552-563, and 'LST' as SEQ ID NOS 564-575, respectively, in order of appearance. FIG. 21C discloses 'MGB1' as SEQ ID NOS 576-587, respectively, in order of appearance, and 'MGB2' as SEQ ID NOS 588-599, respectively, in order of appearance.

FIG. 22 shows a list of exemplary primers and probes used in cast-PCR assays performed using chemically modified allele-specific primers. In this exemplary embodiment, the chemical modifications (e.g., ppA, ppG, fdU, and iso dC) of the ASP are at the 3'-ends. (The chemically modified nucleotides are shown in parentheses.) FIG. 22 discloses 'ASP1' as SEQ ID NOS 600-605, respectively, in order of appearance, 'LSP' as SEQ ID NOS 606-611, respectively, in order of appearance, 'MGB1' as SEQ ID NOS 612-617, respectively, in order of appearance, 'ASP2' as SEQ ID NOS 618-623, respectively, in order of appearance, 'LST' as SEQ ID NOS 624-629, respectively, in order of appearance, and 'MGB2' as SEQ ID NOS 630-635, respectively, in order of appearance.

DETAILED DESCRIPTION

I. Introduction

Figure 1:
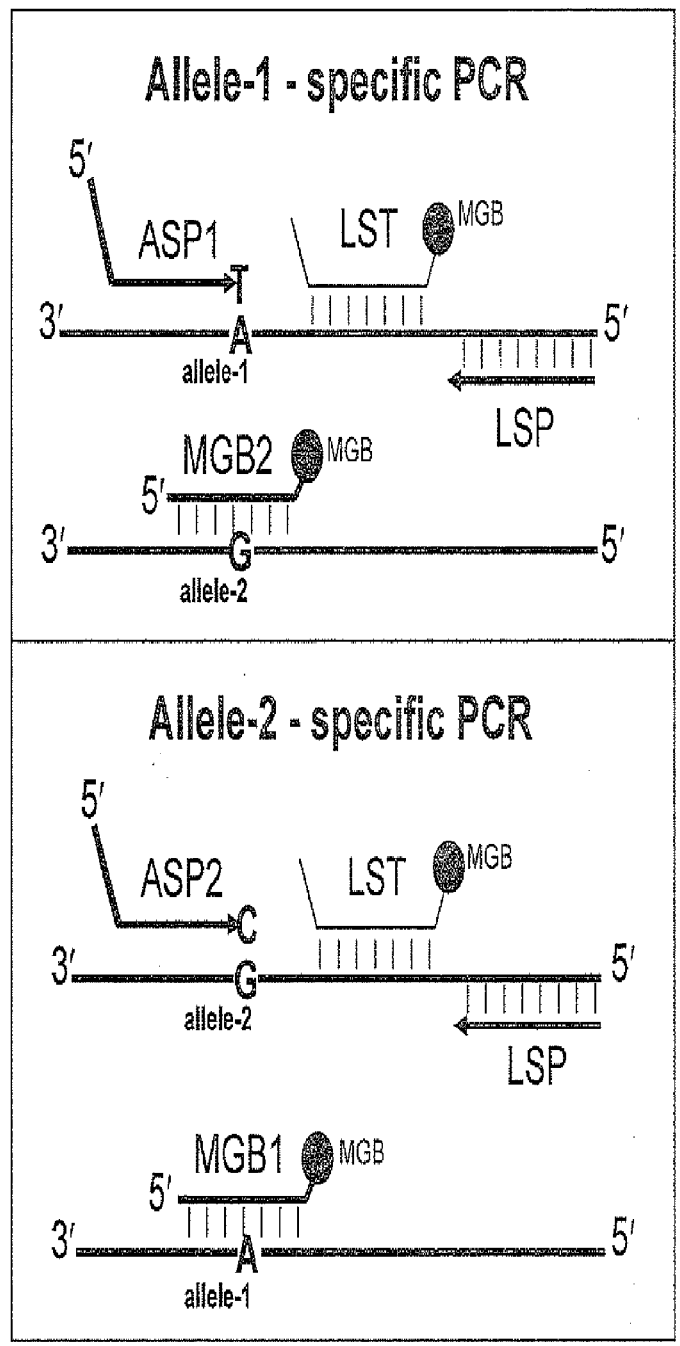
FIG. 1 depicts a schematic of an illustrative embodiment of cast-PCR. In some embodiments, components of cast-PCR include the following: one locus-specific TaqMan probe (LST); two MGB blockers: one allele-1-specific MGB blocker (MGB1) and one allele-2-specific MGB blocker (MGB2); 3 PCR primers: one locus-specific PCR primer (LSP); one allele-1-specific primer (ASP1) and one allele-2-specific primer (ASP2).
Figure 2:
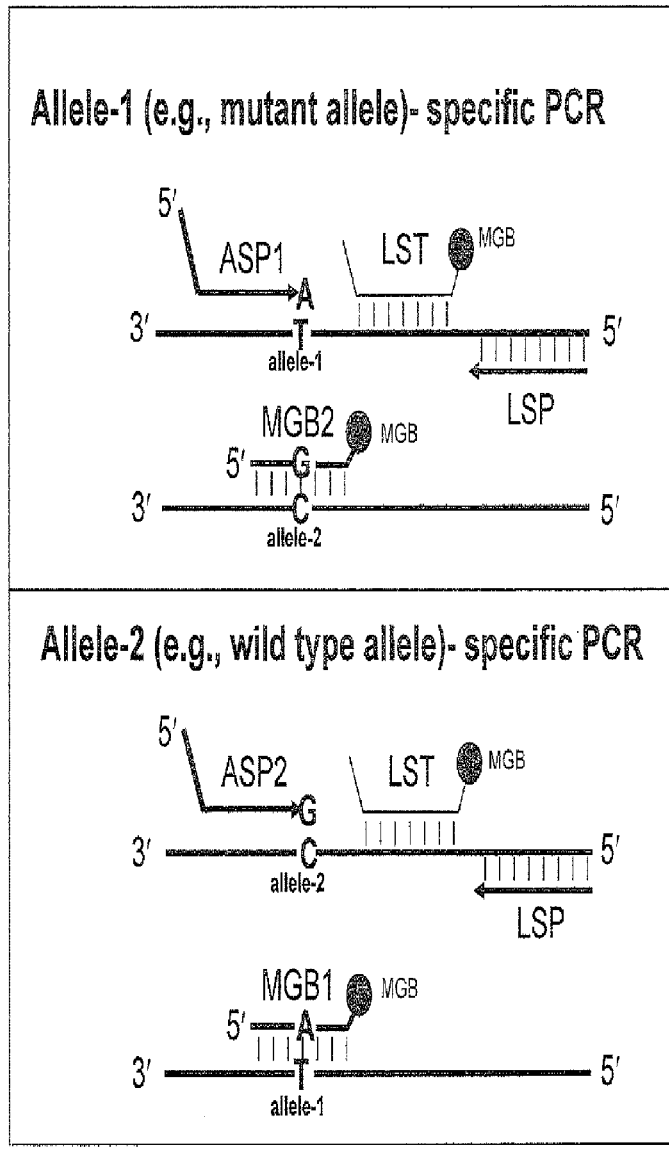
FIG. 2 depicts a schematic of an illustrative embodiment of cast-PCR using allele-specific blocker probes comprising highly discriminating bases for detecting rare allelic variants. Highly discriminating bases may include, for example, A/A, A/G, G/A, G/G, A/C, C/A. The least discriminating bases may include, for example, C/C, T/C, G/T, T/G, C/T. In some embodiments, for example, for detection of A-G or C-T SNPs, A & G are used as the discriminating base if A//T is allelic variant (e.g., mutant allele); or C & T are used as the discriminating base if C//G allelic variant (e.g., mutant allele).

The selective amplification of an allele of interest is often complicated by factors including the mispriming and extension of a mismatched allele-specific primer on an alternative allele. Such mispriming and extension can be especially problematic in the detection of rare alleles present in a sample populated by an excess of another allelic variant. When in sufficient excess, the mispriming and extension of the other allelic variant may obscure the detection of the allele of interest. When using PCR-based methods, the discrimination of a particular allele in a sample containing alternative allelic variants relies on the selective amplification of an allele of interest, while minimizing or preventing amplification of other alleles present in the sample.

A number of factors have been identified, which alone or in combination, contribute to the enhanced discriminating power of allele-specific PCR. As disclosed herein, a factor which provides a greater $\Delta Ct$ value between a mismatched and matched allele-specific primer is indicative of greater discriminating power between allelic variants. Such factors found to improve discrimination of allelic variants using the present methods include, for example, the use of one or more of the following: (a) tailed allele-specific primers; (b) low allele-specific primer concentration; (c) allele-specific primers designed to have lower Tms; (d) allele-specific primers designed to target discriminating bases; (e) allele-specific blocker probes designed to prevent amplification from alternative, and potentially more abundant, allelic variants in a sample; and (f) allele-specific blocker probes and/or allele-specific primers designed to comprise modified bases in order to increase the delta Tm between matched and mismatched target sequences.

The above-mentioned factors, especially when used in combination, can influence the ability of allele-specific PCR to discriminate between different alleles present in a sample. Thus, the present disclosure relates generally to novel amplification methods referred to as cast-PCR, which utilizes a combination of factors referred to above to improve discrimination of allelic variants during PCR by increasing $\Delta Ct$ values. In some embodiments, the present methods can involve high levels of selectivity, wherein one mutant molecule in a background of at least 1,000 to 1,000,000, such as about 1000-10,000, about 10,000 to 100,000, or about 100,000 to 1,000,000 wild type molecules, or any fractional ranges in between can be detected. In some embodiments, the comparison of a first set of amplicons and a second set of amplicons involving the disclosed methods provides improvements in specificity from 1,000× to 100,000,000× fold difference, such as about 1000-10,000×, about 10,000 to 100,000×, about 100,000 to 1,000,000× or about 1,000,000 to 100,000,000× fold difference, or any fractional ranges in between.

II. Definitions

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended.

As used herein, the term "allele" refers generally to alternative DNA sequences at the same physical locus on a segment of DNA, such as, for example, on homologous chromosomes. An allele can refer to DNA sequences which differ between the same physical locus found on homologous chromosomes within a single cell or organism or which differ at the same physical locus in multiple cells or organisms ("allelelic variant"). In some instances, an allele can correspond to a single nucleotide difference at a particular physical locus. In other embodiments and allele can correspond to nucleotide (single or multiple) insertion or deletion.

As used herein, the term "allele-specific primer" refers to an oligonucleotide sequence that hybridizes to a sequence comprising an allele of interest, and which when used in PCR can be extended to effectuate first strand cDNA synthesis. Allele-specific primers are specific for a particular allele of a given target DNA or loci and can be designed to detect a difference of as little as one nucleotide in the target sequence. Allele-specific primers may comprise an allele-specific nucleotide portion, a target-specific portion, and/or a tail.

As used herein, the terms "allele-specific nucleotide portion" or "allele-specific target nucleotide" refers to a nucleotide or nucleotides in an allele-specific primer that can selectively hybridize and be extended from one allele (for example, a minor or mutant allele) at a given locus to the exclusion of the other (for example, the corresponding major or wild type allele) at the same locus.

As used herein, the term "target-specific portion" refers to the region of an allele-specific primer that hybridizes to a target polynucleotide sequence. In some embodiments, the target-specific portion of the allele-specific primer is the priming segment that is complementary to the target sequence at a priming region 5' of the allelic variant to be detected. The target-specific portion of the allele-specific primer may comprise the allele-specific nucleotide portion. In other instances, the target-specific portion of the allele-specific primer is adjacent to the 3' allele-specific nucleotide portion.

As used herein, the terms "tail" or "5'-tail" refers to the non-3' end of a primer. This region typically will, although does not have to contain a sequence that is not complementary to the target polynucleotide sequence to be analyzed. The 5' tail can be any of about 2-30, 2-5, 4-6, 5-8, 6-12, 7-15, 10-20, 15-25 or 20-30 nucleotides, or any range in between, in length.

As used herein, the term "allele-specific blocker probe" (also referred to herein as "blocker probe," "blocker,") refers to an oligonucleotide sequence that binds to a strand of DNA comprising a particular allelic variant which is located on the same, opposite or complementary strand as that bound by an allelic-specific primer, and reduces or prevents amplification of that particular allelic variant. As discussed in greater detail herein, allele-specific blocker probes generally comprise modifications, e.g., at the 3'-OH of the ribose ring, which prevent primer extension by a polymerase. The allele-specific blocker probe can be designed to anneal to the same or opposing strand of what the allele-specific primer anneals to and can be modified with a blocking group (e.g., a "non-extendable blocker moiety") at its 3' terminal end. Thus, a blocker probe can be designed, for example, so as to tightly bind to a wild type allele (e.g., abundant allelic variant) in order to suppress amplification of the wild type allele while amplification is allowed to occur on the same or opposing strand comprising a mutant allele (e.g., rare allelic variant) by extension of an allele-specific primer. In illustrative examples, the allele-specific blocker probes do not include a label, such as a fluorescent, radioactive, or chemiluminescent label As used herein, the term "non-extendable blocker moiety" refers generally to a modification on an oligonucleotide sequence such as a probe and/or primer which renders it incapable of extension by a polymerase, for example, when hybridized to its complementary sequence in a PCR reaction. Common examples of blocker moieties include modifications of the ribose ring 3'-OH of the oligonucleotide, which prevents addition of further bases to the '3-end of the oligonucleotide sequence a polymerase. Such 3'-OH modifications are well known in the art. (See, e.g., Josefsen, M., et al., *Molecular and Cellular Probes*, 23 (2009):201-223; McKinzie, P. et al., *Mutagenesis*. 2006, 21(6):391-7; Parsons, B. et al., *Methods Mol Biol*. 2005, 291:235-45; Parsons, B. et al., *Nucleic Acids Res*. 1992, 25:20(10):2493-6; and Morlan, J. et al., *PLoS One* 2009, 4 (2): e4584, the disclosures of which are incorporated herein by reference in their entireties.)

As used herein, the terms "MGB," "MGB group," "MGB compound," or "MBG moiety" refers to a minor groove binder. When conjugated to the 3' end of an oligonucleotide, an MGB group can function as a non-extendable blocker moiety.

An MGB is a molecule that binds within the minor groove of double stranded DNA. Although a general chemical formula for all known MGB compounds cannot be provided because such compounds have widely varying chemical structures, compounds which are capable of binding in the minor groove of DNA, generally speaking, have a crescent shape three dimensional structure. Most MGB moieties have a strong preference for A-T (adenine and thymine) rich regions of the B form of double stranded DNA. Nevertheless, MGB compounds which would show preference to C-G (cytosine and guanine) rich regions are also theoretically possible. Therefore, oligonucleotides comprising a radical or moiety derived from minor groove binder molecules having preference for C-G regions are also within the scope of the present invention.

Some MGBs are capable of binding within the minor groove of double stranded DNA with an association constant of $10^3 M^{-1}$ or greater. This type of binding can be detected by well established spectrophotometric methods such as ultraviolet (UV) and nuclear magnetic resonance (NMR) spectroscopy and also by gel electrophoresis. Shifts in UV spectra upon binding of a minor groove binder molecule and NMR spectroscopy utilizing the "Nuclear Overhauser" (NOSEY) effect are particularly well known and useful techniques for this purpose. Gel electrophoresis detects binding of an MGB to double stranded DNA or fragment thereof, because upon such binding the mobility of the double stranded DNA changes.

A variety of suitable minor groove binders have been described in the literature. See, for example, Kutyavin, et al. U.S. Pat. No. 5,801,155; Wemmer, D. E., and Dervan P. B., Current Opinion in Structural Biology, 7:355-361 (1997); Walker, W. L., Kopka, J. L. and Goodsell, D. S., Biopolymers, 44:323-334 (1997); Zimmer, C.& Wahnert, U. Prog. Biophys. Molec. Bio. 47:31-112 (1986) and Reddy, B. S. P., Dondhi, S. M., and Lown, J. W., Pharmacol. Therap., 84:1-111 (1999) (the disclosures of which are herein incorporated by reference in their entireties). A preferred MGB in accordance with the present disclosure is $DPI_3$. Synthesis methods and/or sources for such MGBs are also well known in the art. (See, e.g., U.S. Pat. Nos. 5,801,155; 6,492,346; 6,084,102; and 6,727,356, the disclosures of which are incorporated herein by reference in their entireties.)

As used herein, the term "MGB blocker probe," "MBG blocker," or "MGB probe" is an oligonucleotide sequence and/or probe further attached to a minor groove binder moiety at its 3' and/or 5' end. Oligonucleotides conjugated to MGB moieties form extremely stable duplexes with single-stranded and double-stranded DNA targets, thus allowing shorter probes to be used for hybridization based assays. In comparison to unmodified DNA, MGB probes have higher melting temperatures (Tm) and increased specificity, especially when a mismatch is near the MGB region of the hybridized duplex. (See, e.g., Kutyavin, I. V., et al., Nucleic Acids Research, 2000, Vol. 28, No. 2: 655-661).

As used herein, the term "modified base" refers generally to any modification of a base or the chemical linkage of a base in a nucleic acid that differs in structure from that found in a naturally occurring nucleic acid. Such modifications can include changes in the chemical structures of bases or in the chemical linkage of a base in a nucleic acid, or in the backbone structure of the nucleic acid. (See, e.g., Latorra, D. et al., *Hum Mut* 2003, 2:79-85. Nakiandwe, J. et al., *Plant Method* 2007, 3:2.)

As used herein, the term "detector probe" refers to any of a variety of signaling molecules indicative of amplification. For example, SYBR® Green and other DNA-binding dyes are detector probes. Some detector probes can be sequence-based (also referred to herein as "locus-specific detector probe"), for example 5' nuclease probes. Various detector probes are known in the art, for example (TaqMan® probes described herein (See also U.S. Pat. No. 5,538,848) various stem-loop molecular beacons (See, e.g., U.S. Pat. Nos. 6,103,476 and 5,925,517 and Tyagi and Kramer, 1996, Nature Biotechnology 14:303-308), stemless or linear beacons (See, e.g., WO 99/21881), PNA Molecular Beacons™ (See, e.g., U.S. Pat. Nos. 6,355,421 and 6,593,091), linear PNA beacons (See, e.g., Kubista et al., 2001, SPIE 4264: 53-58), non-FRET probes (See, e.g., U.S. Pat. No. 6,150, 097), Sunrise®/Amplifluor® probes (U.S. Pat. No. 6,548, 250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can comprise reporter dyes such as, for example, 6-carboxyfluorescein (6-FAM) or tetrachlorofluorescein (TET). Detector probes can also comprise quencher moieties such as tetramethylrhodamine (TAMRA), Black Hole Quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher on the other, wherein hybridization of the two probes together on a target quenches the signal, or wherein hybridization on a target alters the signal signature via a change in fluorescence. Detector probes can also comprise sulfonate derivatives of fluorescein dyes with $SO_3$ instead of the carboxylate group, phosphoramidite forms of fluorescein, phosphoramidite forms of CY5 (available, for example, from Amersham Biosciences-GE Healthcare).

As used herein, the term "locus-specific primer" refers to an oligonucleotide sequence that hybridizes to products derived from the extension of a first primer (such as an allele-specific primer) in a PCR reaction, and which can effectuate second strand cDNA synthesis of said product. Accordingly, in some embodiments, the allele-specific primer serves as a forward PCR primer and the locus-specific primer serves as a reverse PCR primer, or vice versa. In some preferred embodiments, locus-specific primers are present at a higher concentration as compared to the allele-specific primers.

As used herein, the term "rare allelic variant" refers to a target polynucleotide present at a lower level in a sample as compared to an alternative allelic variant. The rare allelic variant may also be referred to as a "minor allelic variant" and/or a "mutant allelic variant." For instance, the rare allelic variant may be found at a frequency less than 1/10, 1/100, 1/1,000, 1/10,000, 1/100,000, 1/1,000,000, 1/10,000,000, 1/100,000,000 or 1/1,000,000,000 compared to another allelic variant for a given SNP or gene. Alternatively, the rare allelic variant can be, for example, less than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750, 000, or 1,000,000 copies per 1, 10, 100, 1,000 micro liters of a sample or a reaction volume.

As used herein, the terms "abundant allelic variant" may refer to a target polynucleotide present at a higher level in a sample as compared to an alternative allelic variant. The abundant allelic variant may also be referred to as a "major allelic variant" and/or a "wild type allelic variant." For instance, the abundant allelic variant may be found at a frequency greater than 10×, 100×, 1,000×, 10,000×, 100, 000×, 1,000,000×, 10,000,000×, 100,000,000× or 1,000, 000,000× compared to another allelic variant for a given SNP or gene. Alternatively, the abundant allelic variant can be, for example, greater than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters of a sample or a reaction volume.

As used herein, the terms "first" and "second" are used to distinguish the components of a first reaction (e.g., a "first" reaction; a "first" allele-specific primer) and a second reaction (e.g., a "second" reaction; a "second" allele-specific primer). By convention, as used herein the first reaction amplifies a first (for example, a rare) allelic variant and the second reaction amplifies a second (for example, an abundant) allelic variant or vice versa.

As used herein, both "first allelic variant" and "second allelic variant" can pertain to alleles of a given locus from the same organism. For example, as might be the case in human samples (e.g., cells) comprising wild type alleles, some of which have been mutated to form a minor or rare allele. The first and second allelic variants of the present teachings can also refer to alleles from different organisms. For example, the first allele can be an allele of a genetically modified organism, and the second allele can be the corresponding allele of a wild type organism. The first allelic variants and second allelic variants of the present teachings can be contained on gDNA, as well as mRNA and cDNA, and generally any target nucleic acids that exhibit sequence variability due to, for example, SNP or nucleotide(s) insertion and/or deletion mutations.

As used herein, the term "thermostable" or "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under conditions such as is typically required for PCR amplification.

As used herein, the term "PCR amplifying" or "PCR amplification" refers generally to cycling polymerase-mediated exponential amplification of nucleic acids employing primers that hybridize to complementary strands, as described for example in Innis et al., PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; 6,174,670; and 6,814,934 and include, but are not limited to, the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), the ABI GeneAmp® 7500 Sequence Detection System (Applied Biosystems, Foster City, Calif.), the StepOne™ Real-Time PCR System (Applied Biosystems, Foster City, Calif.) and the ABI GeneAmp® 7900 Sequence Detection System (Applied Biosystems, Foster City, Calif.).

As used herein, the term "Tm" or "melting temperature" of an oligonucleotide refers to the temperature (in degrees Celsius) at which 50% of the molecules in a population of a single-stranded oligonucleotide are hybridized to their complementary sequence and 50% of the molecules in the population are not-hybridized to said complementary sequence. The Tm of a primer or probe can be determined empirically by means of a melting curve. In some cases it can also be calculated using formulas well know in the art (See, e.g., Maniatis, T., et al., Molecular cloning: a laboratory manual/Cold Spring Harbor Laboratory, Cold Spring Harbor, N.Y.: 1982).

As used herein, the term "sensitivity" refers to the minimum amount (number of copies or mass) of a template that can be detected by a given assay. As used herein, the term "specificity" refers to the ability of an assay to distinguish between amplification from a matched template versus a mismatched template. Frequently, specificity is expressed as $\Delta C_t = Ct_{mismatch} - Ct_{match}$. An improvement in specificity or "specificity improvement" or "fold difference" is expressed herein as $2^{(\Delta Ct\_condition1 - \Delta Ct\_condition2)}$. The term "selectivity" refers to the extent to which an AS-PCR assay can be used to determine minor (often mutant) alleles in mixtures without interferences from major (often wild type) alleles. Selectivity is often expressed as a ratio or percentage. For example, an assay that can detect 1 mutant template in the presence of 100 wild type templates is said to have a selectivity of 1:100 or 1%. As used herein, assay selectivity can also be calculated as $\frac{1}{2}^{\Delta Ct}$ or as a percentage using $(\frac{1}{2}^{\Delta Ct} \times 100)$.

As used herein, the term "Ct" or "Ct value" refers to threshold cycle and signifies the cycle of a PCR amplification assay in which signal from a reporter that is indicative of amplicon generation (e.g., fluorescence) first becomes detectable above a background level. In some embodiments, the threshold cycle or "Ct" is the cycle number at which PCR amplification becomes exponential.

As used herein, the term "delta Ct" or "$\Delta$Ct" refers to the difference in the numerical cycle number at which the signal passes the fixed threshold between two different samples or reactions. In some embodiments delta Ct is the difference in numerical cycle number at which exponential amplification is reached between two different samples or reactions. The delta Ct can be used to identify the specificity between a matched primer to the corresponding target nucleic acid sequence and a mismatched primer to the same corresponding target nucleic acid sequence.

In some embodiments, the calculation of the delta Ct value between a mismatched primer and a matched primer is used as one measure of the discriminating power of allele-specific PCR. In general, any factor which increases the difference between the Ct value for an amplification reaction using a primer that is matched to a target sequence (e.g., a sequence comprising an allelic variant of interest) and that of a mismatched primer will result in greater allele discrimination power.

According to various embodiments, a Ct value may be determined using a derivative of a PCR curve. For example, a first, second, or nth order derivative method may be performed on a PCR curve in order to determine a Ct value. In various embodiments, a characteristic of a derivative may be used in the determination of a Ct value. Such characteristics may include, but are not limited by, a positive inflection of a second derivative, a negative inflection of a second derivative, a zero crossing of the second derivative, or a positive inflection of a first derivative. In various embodiments, a Ct value may be determined using a thresholding and baselining method. For example, an upper bound to an exponential phase of a PCR curve may be established using a derivative method, while a baseline for a PCR curve may be determined to establish a lower bound to an exponential phase of a PCR curve. From the upper and lower bound of a PCR curve, a threshold value may be established from which a Ct value is determined. Other methods for the determination of a Ct value known in the art, for example, but not limited by, various embodiments of a fit point method, and various embodiments of a sigmoidal method (See, e.g., U.S. Pat. Nos. 6,303,305; 6,503,720; 6,783,934, 7,228,237 and U.S. Application No. 2004/0096819; the disclosures of which are herein incorporated by reference in their entireties).

III. Compositions, Methods and Kits

In one aspect, the present invention provides compositions for use in identifying and/or quantitating an allelic variant in a nucleic acid sample. Some of these compositions can comprise: (a) an allele-specific primer; (b) an allele-specific blocker probe; (c) a detector probe; and (d) a locus-specific primer, or any combinations thereof. In some embodiments of the compositions, the compositions may further comprise a polymerase, dNTPs, reagents and/or buffers suitable for PCR amplification, and/or a template sequence or nucleic acid sample. In some embodiments, the polymerase can be thermostable.

In another aspect, the invention provides compositions comprising: (i) a first allele-specific primer, wherein an allele-specific nucleotide portion of the first allele-specific primer is complementary to the first allelic variant of a target sequence; and (ii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder.

In some illustrative embodiments, the compositions can further include a locus-specific primer that is complementary to a region of the target sequence that is 3' from the first allelic variant and on the opposite strand.

In further embodiments, the compositions can further include a detector probe.

In another aspect, the present invention provides methods for amplifying an allele-specific sequence. Some of these methods can include: (a) hybridizing an allele-specific primer to a first nucleic acid molecule comprising a target allele; (b) hybridizing an allele-specific blocker probe to a second nucleic acid molecule comprising an alternative allele wherein the alternative allele corresponds to the same loci as the target allele; (c) hybridizing a locus-specific detector probe to the first nucleic acid molecule; (d) hybridizing a locus-specific primer to the extension product of the allele-specific primer and (e) PCR amplifying the target allele.

In another aspect, the present invention provides methods for detecting and/or quantitating an allelic variant in a mixed sample. Some of these methods can involve: (a) in a first reaction mixture hybridizing a first allele-specific primer to a first nucleic acid molecule comprising a first allele (allele-1) and in a second reaction mixture hybridizing a second allele-specific primer to a first nucleic acid molecule comprising a second allele (allele-2), wherein the allele-2 corresponds to the same loci as allele-1; (b) in the first reaction mixture hybridizing a first allele-specific blocker probe to a second nucleic acid molecule comprising allele-2 and in the second reaction mixture hybridizing a second allele-specific blocker probe to a second nucleic acid molecule comprising allele-1; (c) in the first reaction mixture, hybridizing a first detector probe to the first nucleic acid molecule and in the second reaction mixture, hybridizing a second detector probe to the first nucleic acid molecule; (d) in the first reaction mixture hybridizing a first locus-specific primer to the extension product of the first allele-specific primer and in the second reaction mixture hybridizing a second locus-specific primer to the extension product of the second allele-specific primer; and (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In yet another aspect, the present invention provides methods for detecting and/or quantitating allelic variants. Some of these methods can comprise: (a) PCR amplifying a first allelic variant in a first reaction comprising (i) a low-concentration first allele-specific primer, (ii) a first locus-specific primer, and (iii) a first blocker probe to form first amplicons; (b) PCR amplifying a second allelic variant in a second reaction comprising (i) a low-concentration second allele-specific primer, (ii) a second locus-specific primer, and (iii) a second blocker probe to form second amplicons; and (d) comparing the first amplicons to the second amplicons to quantitate the first allelic variant in the sample comprising second allelic variants.

In yet another aspect, the present invention provides methods for detecting a first allelic variant of a target sequence in a nucleic acid sample suspected of comprising at least a second allelic variant of the target sequence. Methods of this aspect include forming a first reaction mixture by combining the following: (i) a nucleic acid sample; (ii) a first allele-specific primer, wherein an allele-specific nucleotide portion of the first allele-specific primer is complementary to the first allelic variant of the target sequence; (iii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder; (iv) a first locus-specific primer that is complementary to a region of the target sequence that is 3' from the first allelic variant and on the opposite strand; and (v) a first detector probe.

Next an amplification reaction, typically a PCR amplification reaction, is carried out on the first reaction mixture using the first locus-specific primer and the first allele-specific primer to form a first amplicon. Then, the first amplicon is detected by a change in a detectable property of the first detector probe upon binding to the amplicon, thereby detecting the first allelic variant of the target gene in the nucleic acid sample. The detector probe in some illustrative embodiments is a 5' nuclease probe. The detectable property in certain illustrative embodiments is fluorescence.

In some embodiments, the 3' nucleotide position of the 5' target region of the first allele-specific primer is an allele-specific nucleotide position. In certain other illustrative embodiments, including those embodiments where the 3' nucleotide position of the 5' target region of the first allele-specific primer is an allele-specific nucleotide position, the blocking region of the allele-specific primer encompasses the allele-specific nucleotide position. Furthermore, in illustrative embodiments, the first allele-specific blocker probe includes a minor groove binder. Furthermore, the allele-specific blocker probe in certain illustrative embodiments does not have a label, for example a fluorescent label, or a quencher.

In certain illustrative embodiments, the quantity of the first allelic variant is determined by evaluating the change in a detectable property of the first detector probe.

In certain illustrative embodiments, the method further includes forming a second reaction mixture by combining (i) the nucleic acid sample; (ii) a second allele-specific primer, wherein an allele-specific nucleotide portion of the second allele-specific primer is complementary to the second allelic variant of the target sequence; (iii) a second allele-specific blocker probe that is complementary to a region of the target sequence comprising the first allelic variant, wherein said region encompasses a position corresponding to the binding position of the allele-specific nucleotide portion of the second allele-specific primer, and wherein the second allele-specific blocker probe comprises a minor groove binder; (iv) a second locus-specific primer that is complementary to a region of the target sequence that is 3' from the second allelic variant and on the opposite strand; and (v) a second detector probe. Next, an amplification reaction is carried out on the second reaction mixture using the second allele-specific primer and the locus-specific primer, to form a second amplicon. Then the second amplicon is detected by a change in a detectable property of the detector probe.

In certain embodiments, the method further includes comparing the change in a detectable property of the first detector probe in the first reaction mixture to the change in a detectable property of the second detector probe in the second reaction mixture.

In preferred embodiments, the methods further include a 2-stage cycling protocol. In some embodiments, the cycling protocol comprises a first stage of amplification that employs an initial number of cycles at a lower annealing/extension temperature, followed by a second stage of amplification that employs a number of cycles at a higher annealing/extension temperature. Due to the lower Tm of cast-PCR allele-specific primers (e.g., 53-56° C.), PCR is not optimal at standard annealing/extension conditions (e.g., 60-64° C.). Consequently, lower annealing/extension temperatures are used during the initial cycling stage which improves cast-PCR efficiency significantly.

In some embodiments, the number of cycles used in the first stage of the cast-PCR cycling protocol is fewer than the number of cycles used in the second stage. In some embodiments of the cast-PCR methods, the number of cycles used in the first stage of the cycling protocol is about 2%-20%, 4%-18%, 6%-16%, 8%-14%, 10%-12%, or any percent in between, of the total number of cycles used in the second stage. In some embodiments, the first stage employs between 1 to 10 cycles, 2 to 8 cycles, 3 to 7 cycles, or 4 to 6 cycles, and all number of cycles in between, e.g., 2, 3, 4, 5, 6, or 7 cycles.

In some embodiments, the number of cycles used in the second stage of the cast-PCR cycling protocol is greater than the number of cycles used in the second stage. In some embodiments of the cast-PCR methods, the number of cycles used in the second stage of the cycling protocol is 5 times, 6 times, 8 times, 10 times, 12 times, 18 times, 25 times, or 30 times the number of cycles used in the first stage. In some embodiments, the second stage employs between 30 to 50 cycles, 35 to 48 cycles, 40 to 46 cycles, or any number of cycles in between, e.g., 42, 43, 44, 45, or 46 cycles.

In some embodiments, the lower annealing/extension temperature used during the first cycling stage is about 1° C., about 2° C., about 3° C., about 4° C., or about 5° C. lower than the annealing/extension temperature used during the second cycling stage. In some preferred embodiments, the annealing/extension temperature of the first stage is between 50° C. to 60° C., 52° C. to 58° C., or 54° C. to 56° C., e.g., 53° C., 54° C., 55° C. or 55° C. In some preferred embodiments the annealing/extension temperature of the second stage is between 56° C. to 66° C., 58° C. to 64° C., or 60° C. to 62° C., e.g., 58° C., 60° C., 62° C. or 64° C.

There are several major advantages of this 2-stage PCR cycling protocol used in cast-PCR that make it better than conventional AS-PCR methods. First, it improves the detection sensitivity by lowering the Ct value for matched targets or alleles. Next, it improves the specificity of cast-PCR by increasing the ΔCt between Ct values of matched and mismatched sequences. Finally, it can improve the uniformity of cast-PCR by making it equally efficient across various assays.

In yet another aspect, the present invention provides a reaction mixture that includes the following (i) nucleic acid molecule; (ii) an allele-specific primer, wherein an allele-specific nucleotide portion of the allele-specific primer is complementary to a first allelic variant of a target sequence; (iii) an allele-specific blocker probe that is complementary to a region of the target sequence comprising a second allelic variant, wherein said region encompasses a position corresponding to the binding position of the allele-specific nucleotide portion of the allele-specific primer, and wherein the allele-specific blocker probe comprises a minor groove binder; (iv) a locus-specific primer that is complementary to a region of the target sequence that is 3' from the first allelic variant and on the opposite strand; and (v) a detector probe.

In certain embodiments, the methods of the invention are used to detect a first allelic variant that is present at a frequency less than 1/10, 1/100, 1/1,000, 1/10,000, 1/100,000, 1/1,000,000, 1/10,000,000, 1/100,000,000 or 1/1,000,000,000, and any fractional ranges in between, of a second allelic variant for a given SNP or gene. In other embodiments, the methods are used to detect a first allelic variant that is present in less than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters, and any fractional ranges in between, of a sample or a reaction volume.

In some embodiments, the first allelic variant is a mutant. In some embodiments the second allelic variant is wild type. In some embodiments, the present methods can involve detecting one mutant molecule in a background of at least 1,000 to 1,000,000, such as about 1000 to 10,000, about 10,000 to 100,000, or about 100,000 to 1,000,000 wild type molecules, or any fractional ranges in between. In some embodiments, the methods can provide high sensitivity and the efficiency at least comparable to that of TaqMan®-based assays.

In some embodiments, the comparison of the first amplicons and the second amplicons involving the disclosed methods provides improvements in specificity from 1,000× to 1,000,000× fold difference, such as about 1000 to 10,000×, about 10,000 to 100,000×, or about 100,000 to 1,000,000× fold difference, or any fractional ranges in between. In some embodiments, the size of the amplicons range from about 60-120 nucleotides long.

In another aspect, the present invention provides kits for quantitating a first allelic variant in a sample comprising an alternative second allelic variants that include: (a) a first allele-specific primer; (b) a second allele-specific primer; (c), a first locus-specific primer; (d) a second locus-specific primer; (e) a first allele-specific blocker probe; (f) a second allele-specific blocker probe; and (g) a polymerase. In some embodiments of the disclosed kits, the kit further comprises a first locus-specific detector probe and a second locus-specific detector probe.

In another aspect, the present invention provides kits that include two or more containers comprising the following components independently distributed in one of the two or more containers: (i) a first allele-specific primer, wherein an allele-specific nucleotide portion of the first allele-specific primer is complementary to the first allelic variant of a target sequence; and (ii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder.

In some illustrative embodiments, the kits can further include a locus-specific primer that is complementary to a region of the target sequence that is 3' from the first allelic variant and on the opposite strand.

In other embodiments, the kits can further include a detector probe.

In some embodiments, the compositions, methods, and/or kits can be used in detecting circulating cells in diagnosis. In one embodiment, the compositions, methods, and/or kits can be used to detect tumor cells in blood for early cancer diagnosis. In some embodiments, the compositions, methods, and/or kits can be used for cancer or disease-associated genetic variation or somatic mutation detection and validation. In some embodiments, the compositions, methods, and/or kits can be used for genotyping tera-, tri- and di-allelic SNPs. In other embodiments, the compositions, methods, and/or kits can be used for identifying single or multiple nucleotide insertion or deletion mutations. In some embodiments, the compositions, methods, and/or kits can be used for DNA typing from mixed DNA samples for QC and human identification assays, cell line QC for cell contaminations, allelic gene expression analysis, virus typing/rare pathogen detection, mutation detection from pooled samples, detection of circulating tumor cells in blood, and/or prenatal diagnostics.

In some embodiments, the compositions, methods, and/or kits are compatible with various instruments such as, for example, SDS instruments from Applied Biosystems (Foster City, Calif.).

Allele-Specific Primers

Allele-specific primers (ASPs) designed with low Tms exhibit increased discrimination of allelic variants. In some embodiments, the allele-specific primers are short oligomers ranging from about 15-30, such as about 16-28, about 17-26, about 18-24, or about 20-22, or any range in between, nucleotides in length. In some embodiments, the Tm of the allele-specific primers range from about 50° C. to 70° C., such as about 52° C. to 68° C., about 54° C. to 66° C., about 56° C. to 64° C., about 58° C. to 62° C., or any temperature in between (e.g., 53° C., 54° C., 55° C., 56° C.). In other embodiments, the Tm of the allele-specific primers is about 3° C. to 6° C. higher than the anneal/extend temperature of the PCR cycling conditions employed during amplification.

Low allele-specific primer concentration can also improve selectivity. Reduction in concentration of allele-specific primers below 900 nM can increase the delta Ct between matched and mismatched sequences. In some embodiments of the disclosed compositions, the concentration of allele-specific primers ranges from about 20 nM to 900 nM, such as about 50 nM to 700 nM, about 100 nM to 500 nM, about 200 nM to 300 nM, about 400 nM to 500 nM, or any range in between. In some exemplary embodiments, the concentration of the allele-specific primers is between about 200 nM to 400 nM.

In some embodiments, allele-specific primers can comprise an allele-specific nucleotide portion that is specific to the target allele of interest. The allele-specific nucleotide portion of an allele-specific primer is complementary to one allele of a gene, but not another allele of the gene. In other words, the allele-specific nucleotide portion binds to one or more variable nucleotide positions of a gene that is nucleotide positions that are known to include different nucleotides for different allelic variants of a gene. The allele-specific nucleotide portion is at least one nucleotide in length. In exemplary embodiments, the allele-specific nucleotide portion is one nucleotide in length. In some embodiments, the allele-specific nucleotide portion of an allele-specific primer is located at the 3' terminus of the allele-specific primer. In other embodiments, the allele-specific nucleotide portion is located about 1-2, 3-4, 5-6, 7-8, 9-11, 12-15, or 16-20 nucleotides in from the 3'most-end of the allele-specific primer.

Allele-specific primers designed to target discriminating bases can also improve discrimination of allelic variants. In some embodiments, the nucleotide of the allele-specific nucleotide portion targets a highly discriminating base (e.g., for detection of A/A, A/G, G/A, G/G, A/C, or C/A alleles). Less discriminating bases, for example, may involve detection of C/C, T/C, G/T, T/G, C/T alleles. In some embodiments, for example when the allele to be detected involves A/G or C/T SNPs, A or G may be used as the 3' allele-specific nucleotide portion of the allele-specific primer (e.g., if A or T is the major allele), or C or T may be used as the 3' allele-specific nucleotide portion of the allele-specific primer (e.g., if C or G is the major allele). In other embodiments, A may be used as the nucleotide-specific portion at the 3' end of the allele specific primer (e.g., the allele-specific nucleotide portion) when detecting and/or quantifying A/T SNPs. In other embodiments, G may be used as the nucleotide-specific portion at the 3' end of the allele specific primer when detecting and/or quantifying C/G SNPs.

In some embodiments, the allele-specific primer can comprise a target-specific portion that is specific to the polynucleotide sequence (or locus) of interest. In some embodiments the target-specific portion is about 75-85%, 85-95%, 95-99% or 100% complementary to the target polynucleotide sequence of interest. In some embodiments, the target-specific portion of the allele-specific primer can comprise the allele-specific nucleotide portion. In other embodiments, the target-specific portion is located 5' to the allele-specific nucleotide portion. The target-specific portion can be about 4-30, about 5-25, about 6-20, about 7-15, or about 8-10 nucleotides in length. In some embodiments, the Tm of the target specific portion is about 5° C. below the anneal/extend temperature used for PCR cycling. In some embodiments, the Tm of the target specific portion of the allele-specific primer ranges from about 51° C. to 60° C., about 52° C. to 59° C., about 53° C. to 58° C., about 54° C. to 57° C., about 55° C. to 56° C., or about 50° C. to about 60° C.

In some embodiments of the disclosed methods and kits, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments, the allele-specific primer comprises a tail. Allele-specific primers comprising tails, enable the overall length of the primer to be reduced, thereby lowering the Tm without significant impact on assay sensitivity.

In some exemplary embodiments, the tail is on the 5' terminus of the allele-specific primer. In some embodiments, the tail is located 5' of the target-specific portion and/or allele-specific nucleotide portion of the allele-specific primer. In some embodiments, the tail is about 65-75%, about 75-85%, about 85-95%, about 95-99% or about 100% non-complementary to the target polynucleotide sequence of interest. In some embodiments the tail can be about 2-40, such as about 4-30, about 5-25, about 6-20, about 7-15, or about 8-10 nucleotides in length. In some embodiments the tail is GC-rich. For example, in some embodiments the tail sequence is comprised of about 50-100%, about 60-100%, about 70-100%, about 80-100%, about 90-100% or about 95-100% G and/or C nucleotides.

The tail of the allele-specific primer may be configured in a number of different ways, including, but not limited to a configuration whereby the tail region is available after primer extension to hybridize to a complementary sequence (if present) in a primer extension product. Thus, for example, the tail of the allele-specific primer can hybridize to the complementary sequence in an extension product resulting from extension of a locus-specific primer.

In some embodiments of the disclosed methods and kits, the tail of the first allele-specific primer and the tail of the second allele-specific primer comprise the same sequence. In other embodiments, the 5' tail of the first allele-specific primer and the 5' tail of the second allele-specific primer are the same sequence.

Allele-Specific Blocker Probes

Allele-specific blocker probes (or ASBs) (herein sometimes referred to as "blocker probes") may be designed as short oligomers that are single-stranded and have a length of 100 nucleotides or less, more preferably 50 nucleotides or less, still more preferably 30 nucleotides or less and most preferably 20 nucleotides or less with a lower limit being approximately 5 nucleotides.

In some embodiments, the Tm of the blocker probes range from 58° C. to 70° C., 61° C. to 69° C., 62° C. to 68° C., 63° C. to 67° C., 64° C. to 66° C., or about 60° C. to about 63° C., or any range in between. In yet other embodiments, the Tm of the allele-specific blocker probes is about 3° C. to 6° C. higher than the anneal/extend temperature in the PCR cycling conditions employed during amplification.

In some embodiments, the blocker probes are not cleaved during PCR amplification. In some embodiments, the blocker probes comprise a non-extendable blocker moiety at their 3'-ends. In some embodiments, the blocker probes can further comprise other moieties (including, but not limited to additional non-extendable blocker moieties, quencher moieties, fluorescent moieties, etc) at their 3'-end, 5'-end, and/or any internal position in between. In some embodiments, the allele position is located about 5-15, such as about 5-11, about 6-10, about 7-9, about 7-12, or about 9-11, such as about 6, about 7, about 8, about 9, about 10, or about 11 nucleotides away from the non-extendable blocker moiety of the allele-specific blocker probes when hybridized to their target sequences. In some embodiments, the non-extendable blocker moiety can be, but is not limited to, an amine ($NH_2$), biotin, PEG, $DPI_3$, or $PO_4$. In some preferred embodiments, the blocker moiety is a minor groove binder (MGB) moiety. (The oligonucleotide-MGB conjugates of the present invention are hereinafter sometimes referred to as "MGB blocker probes" or "MGB blockers.")

As disclosed herein, the use of MGB moieties in allele-specific blocker probes can increase the specificity of allele-specific PCR. One possibility for this effect is that, due to their strong affinity to hybridize and strongly bind to complementary sequences of single or double stranded nucleic acids, MGBs can lower the Tm of linked oligonucleotides (See, for example, Kutyavin, I., et al., Nucleic Acids Res., 2000, Vol. 28, No. 2: 655-661). Oligonucleotides comprising MGB moieties have strict geometric requirements since the linker between the oligonucleotide and the MGB moiety must be flexible enough to allow positioning of the MGB in the minor groove after DNA duplex formation. Thus, MGB blocker probes can provide larger Tm differences between matched versus mismatched alleles as compared to conventional DNA blocker probes.

In general, MGB moieties are molecules that bind within the minor groove of double stranded DNA. Although a generic chemical formula for all known MGB compounds cannot be provided because such compounds have widely varying chemical structures, compounds which are capable of binding in the minor groove of DNA, generally speaking, have a crescent shape three dimensional structure. Most MGB moieties have a strong preference for A-T (adenine and thymine) rich regions of the B form of double stranded DNA. Nevertheless, MGB compounds which would show preference to C-G (cytosine and guanine) rich regions are also theoretically possible. Therefore, oligonucleotides comprising a radical or moiety derived from minor groove binder molecules having preference for C-G regions are also within the scope of the present invention.

Some MGBs are capable of binding within the minor groove of double stranded DNA with an association constant of $10^3 M^{-1}$ or greater. This type of binding can be detected by well established spectrophotometric methods such as ultraviolet (UV) and nuclear magnetic resonance (NMR) spectroscopy and also by gel electrophoresis. Shifts in UV spectra upon binding of a minor groove binder molecule and NMR spectroscopy utilizing the "Nuclear Overhauser" (NOSEY) effect are particularly well known and useful techniques for this purpose. Gel electrophoresis detects binding of an MGB to double stranded DNA or fragment thereof, because upon such binding the mobility of the double stranded DNA changes.

A variety of suitable minor groove binders have been described in the literature. See, for example, Kutyavin, et al. U.S. Pat. No. 5,801,155; Wemmer, D. E., and Dervan P. B., Current Opinion in Structural Biology, 7:355-361 (1997); Walker, W. L., Kopka, J. L. and Goodsell, D. S., Biopolymers, 44:323-334 (1997); Zimmer, C.& Wahnert, U. Prog. Biophys. Molec. Bio. 47:31-112 (1986) and Reddy, B. S. P., Dondhi, S. M., and Lown, J. W., Pharmacol. Therap., 84:1-111 (1999). In one group of embodiments, the MGB is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepines. A preferred MGB in accordance with the present disclosure is $DPI_3$ (see U.S. Pat. No. 6,727,356, the disclosure of which is incorporated herein by reference in its entirety).

Suitable methods for attaching MGBs through linkers to oligonucleotides or probes and have been described in, for example, U.S. Pat. Nos. 5,512,677; 5,419,966; 5,696,251; 5,585,481; 5,942,610; 5,736,626; 5,801,155 and 6,727,356.

(The disclosures of each of which are incorporated herein by reference in their entireties.) For example, MGB-oligonucleotide conjugates can be synthesized using automated oligonucleotide synthesis methods from solid supports having cleavable linkers. In other examples, MGB probes can be prepared from an MGB modified solid support substantially in accordance with the procedure of Lukhtanov et al. Bioconjugate Chem., 7: 564-567 (1996). (The disclosure of which is also incorporated herein by reference in its entirety.) According to these methods, one or more MGB moieties can be attached at the 5'-end, the 3'-end and/or at any internal portion of the oligonucleotide.

The location of an MGB moiety within an MGB-oligonucleotide conjugate can affect the discriminatory properties of such a conjugate. An unpaired region within a duplex will likely result in changes in the shape of the minor groove in the vicinity of the mismatched base(s). Since MGBs fit best within the minor groove of a perfectly-matched DNA duplex, mismatches resulting in shape changes in the minor groove would reduce binding strength of an MGB to a region containing a mismatch. Hence, the ability of an MGB to stabilize such a hybrid would be decreased, thereby increasing the ability of an MGB-oligonucleotide conjugate to discriminate a mismatch from a perfectly-matched duplex. On the other hand, if a mismatch lies outside of the region complementary to an MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The first advantage of the use of MGB-oligonucleotides conjugates in this context lies in the fact that much shorter oligonucleotides compared to those used in the art (i.e., 20-mers or shorter), having greater discriminatory powers, can be used, due to the pronounced stabilizing effect of MGB conjugation. Consequently, larger delta Tms of allele-specific blocker probes can improve AS-PCR assay specificity and selectivity.

Figure 3:
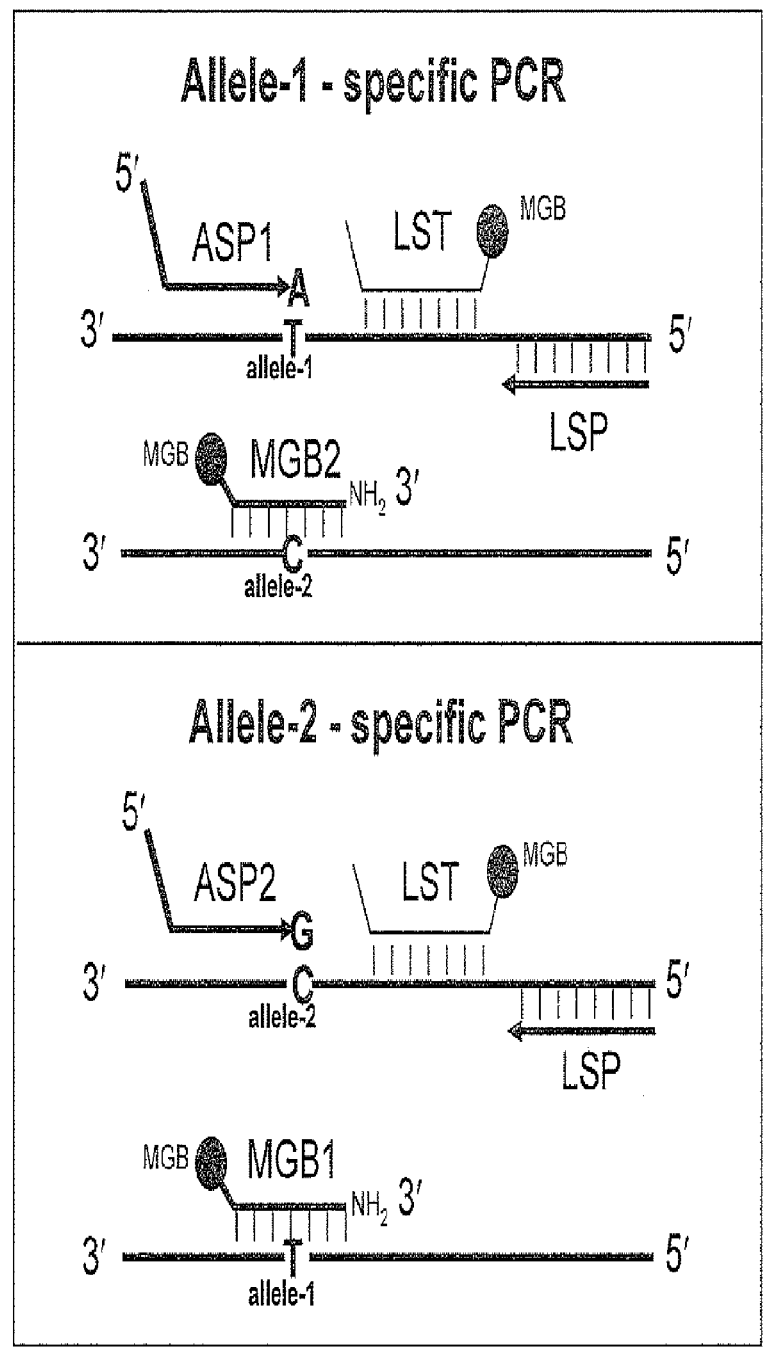
FIG. 3 depicts a schematic of an illustrative embodiment of cast-PCR using an allele-specific blocker probe with an MGB moiety at the 5' end. In some embodiments the blocker moiety at the 3'-end of the probe may include, for example, $NH_2$, biotin, MGB, $PO_4$, and PEG.

Blocker probes having MGB at the 5' termini may have additional advantages over other blocker probes having a blocker moiety (e.g., MGB, $PO_4$, $NH_2$, PEG, or biotin) only at the 3' terminus. This is at least because blocker probes having MGB at the 5' terminus (in addition to a blocking moiety at the 3'-end that prevents extension) will not be cleaved during PCR amplification. Thus, the probe concentration can be maintained at a constant level throughout PCR, which may help maintain the effectiveness of blocking non-specific priming, thereby increasing cast-PCR assay specificity and selectivity (FIG. 3).

Figure 4A:
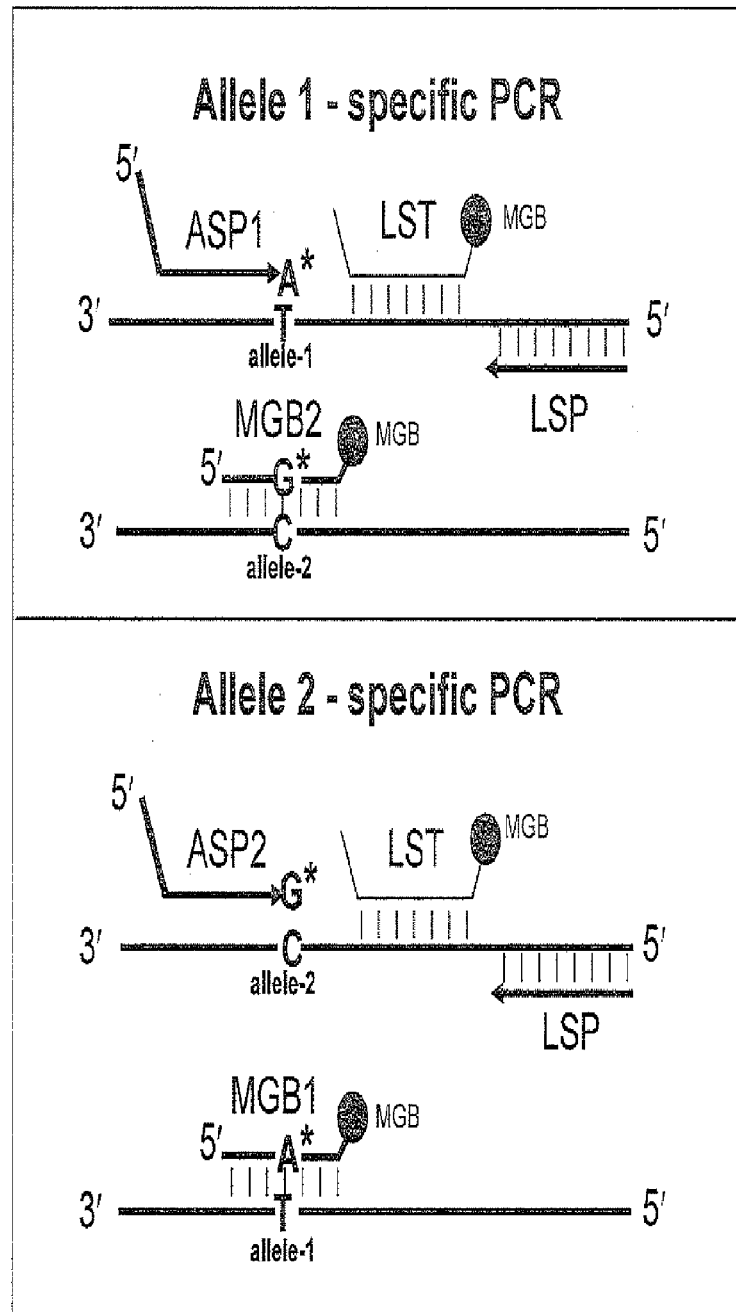
FIG. 4A depicts a schematic of an illustrative embodiment of cast-PCR using modified bases in an MGB blocker probe or allele-specific primer. (G* represents ppG.)

In some embodiments, as depicted in FIG. 4A, the allele-specific primer and/or the allele-specific blocker probe can comprise one or more modified nucleobases or nucleosidic bases different from the naturally occurring bases (i.e., adenine, cytosine, guanine, thymine and uracil). In some embodiments, the modified bases are still able to effectively hybridize to nucleic acid units that contain adenine, guanine, cytosine, uracil or thymine moieties. In some embodiments, the modified base(s) may increase the difference in the Tm between matched and mismatched target sequences and/or decrease mismatch priming efficiency, thereby improving not only assay specificity, bust also selectivity.

Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. In some embodiments, all tautomeric forms of naturally occurring bases, modified bases and base analogues may also be included in the oligonucleotide primers and probes of the invention.

Some examples of modified base(s) may include, for example, the general class of base analogues 7-deazapurines and their derivatives and pyrazolopyrimidines and their derivatives (described in PCT WO 90/14353; and U.S. application Ser. No. 09/054,630, the disclosures of each of which are incorporated herein by reference in their entireties). Examples of base analogues of this type include, for example, the guanine analogue 6-amino-1H-pyrazolo[3,4-d]pyrimidin-4(5H)-one (ppG), the adenine analogue 4-amino-1H-pyrazolo[3,4-d]pyrimidine (ppA), and the xanthine analogue 1H-pyrazolo[4,4-d]pyrimidin-4(5H)-6(7H)-dione (ppX). These base analogues, when present in an oligonucleotide of some embodiments of this invention, strengthen hybridization and can improve mismatch discrimination.

Additionally, in some embodiments, modified sugars or sugar analogues can be present in one or more of the nucleotide subunits of an oligonucleotide conjugate in accordance with the invention. Sugar modifications include, but are not limited to, attachment of substituents to the 2', 3' and/or 4' carbon atom of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl.

Locked nucleic acid (LNA)-type modifications, for example, typically involve alterations to the pentose sugar of ribo- and deoxyribonucleotides that constrains, or "locks," the sugar in the N-type conformation seen in A-form DNA. In some embodiments, this lock can be achieved via a 2'-O, 4'-C methylene linkage in 1,2:5,6-di-O-isopropylene-α-D-allofuranose. In other embodiments, this alteration then serves as the foundation for synthesizing locked nucleotide phosphoramidite monomers. (See, for example, Wengel J., *Acc. Chem. Res.*, 32:301-310 (1998), U.S. Pat. No. 7,060, 809; Obika, et al., *Tetrahedron Lett* 39: 5401-5405 (1998); Singh, et al., *Chem Commun* 4:455-456 (1998); Koshkin, et al., *Tetrahedron* 54: 3607-3630 (1998), the disclosures of each of which are incorporated herein by reference in their entireties.)

Figure 4B:
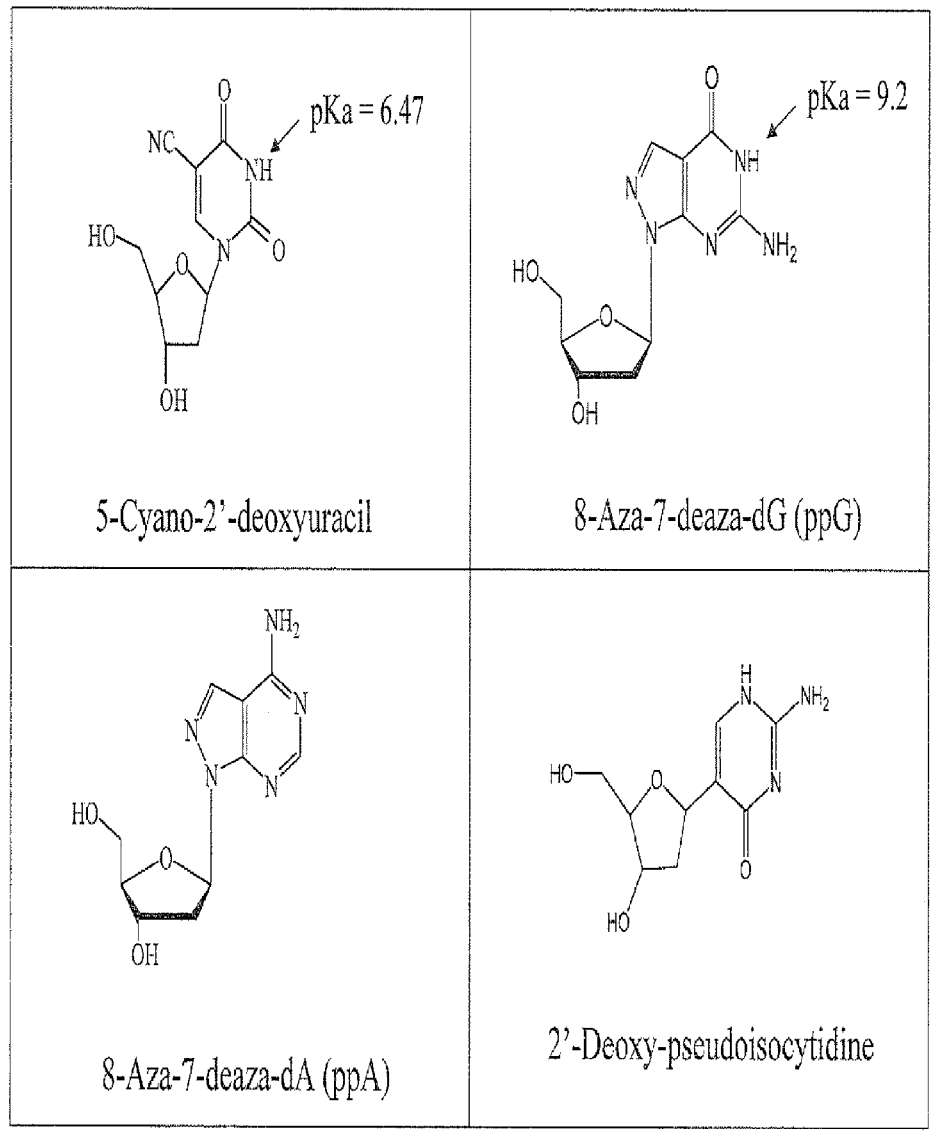
FIG. 4B depicts some examples of modified bases of an MGB blocker probe or allele-specific primer.

In some preferred embodiments, the modified bases include 8-Aza-7-deaza-dA (ppA), 8-Aza-7-deaza-dG (ppG), 2'-Deoxypseudoisocytidine (iso dC), 5-fluoro-2'-deoxyuridine (fdU), locked nucleic acid (LNA), or 2'-O,4'-C-ethylene bridged nucleic acid (ENA) bases. Other examples of modified bases that can be used in the invention are depicted in FIG. 4B and described in U.S. Pat. No. 7,517,978 (the disclosure of which is incorporated herein by reference in its entirety).

Many modified bases, including for example, LNA, ppA, ppG, 5-Fluoro-dU (fdU), are commercially available and can be used in oligonucleotide synthesis methods well known in the art. In some embodiments, synthesis of modified primers and probes can be carried out using standard chemical means also well known in the art. For example, in certain embodiments, the modified moiety or base can be introduced by use of a (a) modified nucleoside as a DNA synthesis support, (b) modified nucleoside as a phosphoramidite, (c) reagent during DNA synthesis (e.g., benzylamine treatment of a convertible amidite when incorporated into a DNA sequence), or (d) by post-synthetic modification.

In some embodiments, the primers or probes are synthesized so that the modified bases are positioned at the 3'end. In some embodiments, the modified base are located between, 1-6 nucleotides, e.g., 2, 3, 4 or 5 nucleotides away from the 3'-end of the allele-specific primer or blocker probe. In some preferred embodiments, the primers or probes are synthesized so that the modified bases are positioned at the 3'-most end of the allele-specific primer or blocker probe.

Modified internucleotide linkages can also be present in oligonucleotide conjugates of the invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

In addition, in some embodiments, the nucleotide units which are incorporated into the oligonucleotides of the allele-specific primers and/or blocker probes of the present invention may have a cross-linking function (an alkylating agent) covalently bound to one or more of the bases, through a linking arm.

In some embodiments of the methods and kits, the first allele-specific blocker probe binds to the same strand or sequence as the first allele-specific primer, while the second allele-specific blocker probe binds to the opposite strand and/or complementary sequence as the first allele-specific primer.

Detector Probes

In some embodiments, detector probe is designed as short oligomers ranging from about 15-30 nucleotides, such as about 16, about 18, about 22, about 24, about 30, or any number in between. In some embodiments, the Tm of the detector probe ranges from about 60° C. to 80° C., about 61° C. to 69° C., about 62° C. to 68° C., about 63° C. to 67° C., or about 64° C. to 66° C., or any range in between.

In some embodiments, the detector probe is a locus-specific detector probes (LST). In other embodiments the detector probe is a 5' nuclease probe. In some exemplary embodiments, the detector probe can comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the detector probe is designed according to the methods and principles described in U.S. Pat. No. 6,727,356 (the disclosure of which is incorporated herein by reference in its entirety). In some exemplary embodiments, the detector probe is a TaqMan® probe (Applied Biosystems, Foster City). In exemplary embodiments, the locus-specific detector probe can be designed according to the principles and methods described in U.S. Pat. No. 6,727,356 (the disclosure of which is incorporated herein by reference in its entirety). For example, fluorogenic probes can be prepared with a quencher at the 3' terminus of a single DNA strand and a fluorophore at the 5' terminus. In such an example, the 5'-nuclease activity of a Taq DNA polymerase can cleave the DNA strand, thereby separating the fluorophore from the quencher and releasing the fluorescent signal. In some embodiments, the detector probes are hybridized to the template strands during primer extension step of PCR amplification (e.g., at 60-65° C.). In yet other embodiments, an MGB is covalently attached to the quencher moiety of the locus-specific detector probes (e.g., through a linker).

In some embodiments of the disclosed methods and kits, the first and second detector probes are the same and/or comprise the same sequence or are the same sequence.

Locus-Specific Primers

In some embodiments, locus-specific primer (LSP) is designed as a short oligomer ranging from about 15-30 nucleotides, such as about 16, about 18, about 22, about 24, about 30, or any number in between. In some embodiments, the Tm of the locus-specific primer ranges from about 60° C. to 70° C., about 61° C. to 69° C., about 62° C. to 68° C., about 63° C. to 67° C., or about 64° C. to 66° C., or any range in between.

In some other embodiments of the disclosed methods and kits, the first locus-specific detector probe and/or second locus-specific detector probes comprise the same sequence or are the same sequence.

Additional Components

Polymerase enzymes suitable for the practice of the present invention are well known in the art and can be derived from a number of sources. Thermostable polymerases may be obtained, for example, from a variety of thermophilic bacteria that are commercially available (for example, from American Type Culture Collection, Rockville, Md.) using methods that are well-known to one of ordinary skill in the art (See, e.g., U.S. Pat. No. 6,245,533). Bacterial cells may be grown according to standard microbiological techniques, using culture media and incubation conditions suitable for growing active cultures of the particular species that are well-known to one of ordinary skill in the art (See, e.g., Brock, T. D., and Freeze, H., J. Bacteriol. 98(1):289-297 (1969); Oshima, T., and Imahori, K, Int. J. Syst. Bacteriol. 24(1):102-112 (1974)). Suitable for use as sources of thermostable polymerases are the thermophilic bacteria *Thermus aquaticus, Thermus thermophilus, Thermococcus litoralis, Pyrococcus furiosus, Pyrococcus woosii* and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants of each of these species. Preferable thermostable polymerases can include, but are not limited to, Taq DNA polymerase, Tne DNA polymerase, Tma DNA polymerase, or mutants, derivatives or fragments thereof.

Various Sources and/or Preparation Methods of Nucleic Acids

Sources of nucleic acid samples in the disclosed compositions, methods and/or kits include, but are not limited to, human cells such as circulating blood, buccal epithelial cells, cultured cells and tumor cells. Also other mammalian tissue, blood and cultured cells are suitable sources of template nucleic acids. In addition, viruses, bacteriophage, bacteria, fungi and other micro-organisms can be the source of nucleic acid for analysis. The DNA may be genomic or it may be cloned in plasmids, bacteriophage, bacterial artificial chromosomes (BACs), yeast artificial chromosomes (YACs) or other vectors. RNA may be isolated directly from the relevant cells or it may be produced by in vitro priming from a suitable RNA promoter or by in vitro transcription. The present invention may be used for the detection of variation in genomic DNA whether human, animal or other. It finds particular use in the analysis of inherited or acquired diseases or disorders. A particular use is in the detection of inherited diseases.

In some embodiments, template sequence or nucleic acid sample can be gDNA. In other embodiments, the template sequence or nucleic acid sample can be cDNA. In yet other embodiments, as in the case of simultaneous analysis of gene expression by RT-PCR, the template sequence or nucleic acid sample can be RNA. The DNA or RNA template sequence or nucleic acid sample can be extracted from any type of tissue including, for example, formalin-fixed paraffin-embedded tumor specimens.

Preamplification

In some embodiments, additional compositions, methods and kits are provided for "boosting" cast-PCR amplification reactions for limited quantity specimens having very low nucleic acid copy number. In some embodiments, said compositions, methods and kits involve a two-step amplification process comprising a first "booster" or pre-amplification multiplex reaction (see, for example, U.S. Pat. Nos. 6,605,451 and 7,087,414 and U.S. Published Application No. 2004/0175733, the disclosures of which are herein incorporated by reference in their entireties), followed by a second single-plex (i.e., cast-PCR) amplification reaction.

In some preferred embodiments, the first step involves a multiplex reaction which uses at least two complete sets of primers (e.g., one forward allele-1-specific primer, one forward allele-2-specific primer and one reverse locus-specific primer), each set of which is suitable or operative for amplifying a specific polynucleotide of interest. In other embodiments, the resultant multiplex products acquired in the first step are divided into optimized secondary single-plex cast-PCR amplification reactions, each containing at least one primer set previously used in the first multiplexing step and then PCR amplified using the cast-PCR methods described herein.

In other preferred embodiments, the first multiplex reaction is a cast-PCR amplification reaction (although other well known amplification methods such as, but not limited to PCR, RT-PCR, NASBA, SDA, TMA, CRCA, Ligase Chain Reaction, etc. can be used). In certain embodiments, the first multiplex reaction comprises a plurality of allele-specific primers, and locus-specific primers, each group of which is specific for a particular allele of interest and designed according to the cast-PCR methods described herein. Unlike single-plex cast-PCR reactions that generate a single amplified sequence, multiplex cast-PCR amplification reactions, by virtue of utilizing a plurality of different primer sets, can permit the simultaneous amplification of a plurality of different sequences of interest in a single reaction. Because a plurality of different sequences is amplified simultaneously in a single reaction, the multiplex amplifications can effectively increase the concentration or quantity of a sample available for downstream cast-PCR assays. Thus, in some preferred embodiments, significantly more analyses or assays can be performed with a pre-amplified cast-PCR sample than could have been performed with the original sample.

The number of different amplification primer pairs utilized in the multiplex amplification is not critical and can range from as few as two, to as many as tens, hundreds, thousands, or even more. Thus, depending upon the particular conditions, the multiplex amplifications permit the simultaneous amplification of from as few as two to as many as tens, hundreds, thousands, or even more polynucleotide sequences of interest.

The number of amplification cycles performed with a multiplex amplification may depend upon, among other factors, the degree of amplification desired. The degree of amplification desired, in turn, may depend upon such factors as the amount of polynucleotide sample to be amplified or the number of alleles or mutations to be detected using subsequent cast-PCR assays.

In preferred embodiments, it may be desirable to keep the multiplex amplification from progressing beyond the exponential phase or the linear phase. Indeed, in some embodiments, it may be desirable to carry out the multiplex amplification for a number of cycles suitable to keep the reaction within the exponential or linear phase. Utilization of a truncated multiplex amplification round can result in a sample having a boosted product copy number of about 100-1000 fold increase.

In many embodiments, pre-amplification permits the ability to perform cast-PCR assays or analyses that require more sample, or a higher concentration of sample, than was originally available. For example, after a 10×, 100×, 1000×, 10,000×, and so on, multiplex amplification, subsequent cast-PCR single-plex assays can then be performed using, respectively, a 10×, 100×, 1000×, 10,000×, and so on, less sample volume. In some embodiments, this allows each single-plex cast-PCR reaction to be optimized for maximum sensitivity and requires only one method of detection for each allele analyzed. This can be a significant benefit to cast-PCR analysis since, in some embodiments, it allows for the use of off-the-shelf commercially available cast-PCR reagents and kits to be pooled together and used in a multiplex amplification reaction without extensive effort toward or constraints against redesigning and/or re-optimizing cast-PCR assays for any given target sequence. Moreover, in some embodiments, the ability to carry out a multiplex amplification with reagents and kits already optimized for cast-PCR analysis permits the creation of multiplex amplification reactions that are ideally correlated or matched with subsequent single-plex cast-PCR assays.

The following examples are intended to illustrate but not limit the invention.

EXAMPLES

I. General Cast-PCR Assay Design:

The general schema for the cast-PCR assays used in the following examples is illustrated in FIG. 1. For each SNP that was analyzed, allele-specific primers (ASPs) were designed to target a first allele (i.e. allele-1) and a second allele (i.e. allele-2). The cast-PCR assay reaction mixture for allele-1 analysis included a 5'-tailed allele-1-specific primer (ASP1), one MGB allele-2 blocker probe (MGB2), one common locus-specific TaqMan probe (LST) and one common locus-specific primer (LSP). The cast-PCR assay reaction mixture for analysis of allele-2 included a 5'-tailed allele-2-specific primer (ASP2), one MGB allele-1 blocker probe (MGB1), one common locus-specific TaqMan probe (LST) and one common locus-specific primer (LSP).

II. Reaction Conditions:

Each assay reaction mixture (10 µl total) contained 1× TaqMan Genotyping Master Mixture (Applied Biosystems, Foster City, Calif.; P/N 437135), 0.5 ng/µL genomic DNA or 1 million copies of plasmid DNA (or as indicated otherwise), 300 nM (unless specified otherwise) tailed-, or in some cases untailed-, allele-specific primer (ASP1 for detection of allele-1 or ASP2 for detection of allele-2), 200 nM TaqMan probe (LST), 900 nM locus-specific primer (LSP), 150 nM allele-specific MGB blocker probe (MGB1 for detection of allele-2 or MGB2 for detection of allele-1). The reactions were incubated in a 384-well plate at 95° C. for 10 minutes, then for 5 cycles at 95° C. for 15 seconds and 58° C. for 1 minute, then by 45 cycles at 95° C. for 15 seconds and 60° C. for 1 minute. All reactions were run in duplicate or higher replication in an ABI PRISM 7900HT® Sequence Detection System, according to the manufacturer's instructions.

The 2-stage cycling protocol used in the following examples for cast-PCR amplification reactions is different from conventional allele-specific PCR (AS-PCR). The 2-stage cycling protocol comprises an initial 5 cycles at a lower annealing/extension temperature (e.g., 58° C.), followed by 45 standard cycles at a higher annealing/extension temperature (e.g., 60° C.). Due to the lower Tm of cast-PCR allele-specific primers (e.g., 53-56° C.), PCR is not optimal at standard annealing/extension conditions (e.g., 60° C.). Consequently, lower annealing/extension temperatures used during the initial 5 cycles increases overall cast-PCR efficiency.

III. Nucleic Acid Samples:

Plasmids containing specific SNP sequences were designed and ordered from BlueHeron (Bothell, Wash.). (See Table 1 for a list of plasmids comprising SNPs used in some of the following examples.) The plasmids were quantified using TaqMan RNase P Assay (Applied Biosystems, Foster City, Calif.; P/N 4316838) according to the manufacturer's instructions and were used as templates (See Table 1, RNase P Control) to validate sensitivity, linear dynamic range, specificity, and selectivity of the given assays.

Genomic DNAs were purchased from Coriell Institute for Medical Research (Camden, N.J.; NA17203, NA17129, NA17201). The genotypes of target SNPs were validated with TaqMan SNP Genotyping Assays (Applied Biosystems, Foster City, Calif.; P/N 4332856) according to the manufacturer's instructions.

IV. Modified Oligonucleotides:

Modified bases were purchased from Berry and Associates (ppA: P/N BA 0239; ppG: P/N BA 0242; fdU: P/N BA 0246; and iso dC: P/N BA 0236) or Exicon (LNA-T Amidite: P/N EQ-0064; LNA-mC Amidite: P/N EQ-0066; LNA-G Amidite: P/N EQ-0082; and LNA-A Amidite: P/N EQ-0063). Oligonucleotides comprising the modified nucleotides at their 3'ends were synthesized according to the manufacturer's instructions.

TABLE 1

Plasmid SNP Sequences (target alleles are indicated in brackets). Table 1 discloses SEQ ID NOS 1-27, respectively, in order of appearance.

| SNP ID | Sequence |
| --- | --- |
| CV11201742 | GCTCTGCTTCATTCCTGTCTGAAGAAGGGCAGATAGTTTGGCTGCTCCTGTG[C/T]TGTCACCTGCAATTCTCC CTTATCAGGGCCATTGGCCTCTCCCTTCTCTCTGTGAGGGATATTTTCTCTGACTTGTCAATCCACATCTTCC |
| CV11349123 | GGCTTGCAATGGCTCCAACCGGAAGGGCGGTGCTCGAGCTGTGGTGCGTGC[C/T]GCTAAGTTGTGCGTTCCA GGGTGCACTCGC |
| CV1207700 | GCAACTATACCCTTGATGGATGGAGATTTA[C/T]GCAATGTGTTTTACTGGGTAGAGTGACAGACCTT |
| CV25594064 | CCTGAACTTATTTGGCAAGAGCGATGAGTACTCTTAAAATTACTATCTGGAAATTATATTATTTAGAATCTGCC AATTACCTAGATCCCCCCT[C/G]AACAATTGTTTCACCAAGGAACTTCCTGAA |
| CV25639181 | GAATTGGTTGTCTCCTTATGGGAACTGGAAGTATTTTGACA[G/T]CTTTACCACATTTCTTCATGGGATAGTAA GTGTTAAACAGCTCTGAGCCATTTATTATCAGCTACTTGTAAATTAGCAGTAGAATTTTATTTTTATACTTGTAA GTGGGCAGTTACCTTTTGAGAGGAATACCTATAG |
| RNaseP Control | GCGGAGGGAAGCTCATCAGTGGGGCCACGAGCTGAGTGCGTCCTGTCACTCCACTCCCATGTCCCTTGGGAAG GTCTGAGACTAGGG |
| BRAF-1799TA | TACTACACCTCAGATATATTTCTTCATGAAGACCTCACAGTAAAAATAGGTGATTTTGGTCTAGCTACAG [T/A]GAAATCTCGATGGAGTGGGTCCCATCAGTTTGAACAGTTGTCTGGATCCATTTTGTGGATGGTAAGAATT GAGGCTATTTTTCCACTGATTAAATTTTTGGCCCTGAGATGCTGCTGAGTT |
| CTNNB1-121AG | TGCTAATACTGTTTCGTATTTATAGCTGATTTGATGGAGTTGGACATGGCCATGGAACCAGACAGAAAGCGG CTGTTAGTCACTGGCAGCAACAGTCTTACCTGGACTCTGGAATCCATTCTGGTGCCACT[A/G]CCACAGCTCCT TCTCTGAGTGGTAAAGGCAATCCTGAGGAAGAGGATGTGGATACCTCCCAAGTC |
| CTNNB1-134CT | TTTGATGGAGTTGGACATGGCCATGGAACCAGACAGAAAGCGGCTGTTAGTCACTGGCAGCAACAGTCTTAC CTGGACTCTGGAATCCATTCTGGTGCCACTACCACAGCTCCTT[C/T]TCTGAGTGGTAAAGGCAATCCTGAGG AAGAGGATGTGGATACCTCCCAAGTCCTGTATGAGTGGGAA |
| EGFR-2369CT | GTGGACAACCCCCACGTGTGCCGCCTGCTGGGCATCTGCCTCACCTCCACCGTGCAGCTCATCA[C/T]GCAGC TCATGCCCTTCGGCTGCCTCCTGGACTATGTCCGGGAACACAAAGACAATATTGGCTCCCAGTACCTGCTCAAC TGGTGTGTGCAGATCGCAAAGGTAATCAGGGAAGGGA |
| EGFR-2573TG | GCATGAACTACTTGGAGGACCGTCGCTTGGTGCACCGCGACCTGGCAGCCAGGAACGTACTGGTGAAAACACC GCAGCATGTCAAGATCACAGATTTTGGGC[T/G]GGCCAAACTGCTGGGTGCGGAAGAGAAAGAATACCATGC AGAAGGAGGCAAAGTAAGGAGGTG |
| KRAS-176CG | CAGGATTCCTACAGGAAGCAAGTAGTAATTGATGGAGAAACCTGTCTCTTGGATATTCTCGACACAG[C/G]AG GTCAAGAGGAGTACAGTGCAATGAGGGACCAGTACATGAGGACTGGGGAGGGCTTTCTTTGTGTATTTGCCAT AAATAATACTAAATCATTTGAAGATATTC |
| KRAS-183AC | ACAGGAAGCAAGTAGTAATTGATGGAGAAACCTGTCTCTTGGATATTCTCGACACAGCAGGTCA[A/C]GAGG AGTACAGTGCAATGAGGGACCAGTACATGAGGACTGGGGAGGGCTTTCTTTGTGTATTTGCCATAAATAATAC TAAATCATTTGAAGATATTCACCATTATAGGTGGGTTTAAATTGAATATAATAAGCTGACATTAA |
| KRAS-34GA | TATTAACCTTATGTGTGACATGTTCTAATATAGTCACATTTTCATTATTTTTATTATAAGGCCTGCTGAAAATGA CTGAATATAAACTTGTGGTAGTTGGAGCT[G/A]GTGGCGTAGGCAAGAGTGCCTTGACGATACAGCTAATTCA GAATCATTTTGTGGACGAATATGA |
| KRAS-35GA | TATTAACCTTATGTGTGACATGTTCTAATATAGTCACATTTTCATTATTTTTATTATAAGGCCTGCTGAAAATGA CTGAATATAAACTTGTGGTAGTTGGAGCTG[G/A]TGGCGTAGGCAAGAGTGCCTTGACGATACAGCTAATTCA GAATCATTTTGTGGACGAATATGATC |
| KRAS-38GA | CATTATTTTTATTATAAGGCCTGCTGAAAATGACTGAATATAAACTTGTGGTAGTTGGAGCTGGTG[G/A]CGTA GGCAAGAGTGCCTTGACGATACAGCTAATTCAGAATCATTTTGTGGACGAATATGATCCAACAATAGAGGTAA |

TABLE 1-continued

Plasmid SNP Sequences (target alleles are indicated in brackets). Table 1 discloses SEQ ID NOS 1-27, respectively, in order of appearance.

| SNP ID | Sequence |
|---|---|
| | ATCTTGTTTTAATATGCATATTACTGGTGCAGGACCATTCTTTGATACAGATAAAGGTTTCTCTGACCATTTTCA TGAGTACTTAT |
| NRAS-181CA | ATTCTTACAGAAAACAAGTGGTTATAGATGGTGAAACCTGTTTGTTGGACATACTGGATACAGCTGGA[C/A]A AGAAGAGTACAGTGCCATGAGAGACCAATACATGAGGACAGGCGAAGGCTTCCTCTGTGTATTTGCCATCAAT AATAGCAAGTCATTTGCGGATATTAACCTCTACAGGTACTAGGAGCATTATTTTCTCTGAAAGGATG |
| NRAS-183AT | TTACAGAAAACAAGTGGTTATAGATGGTGAAACCTGTTTGTTGGACATACTGGATACAGCTGGACA[A/T]GAA GAGTACAGTGCCATGAGAGACCAATACATGAGGACAGGCGAAGGCTTCCTCTGTGTATTTGCCATCAATAATA GCAAGTCATTTGCGGATATTAACCTCTACAGGTACTAGGAGCATTATTTTCTCTGAAAGGATG |
| NRAS-35GA | TGGTTTCCAACAGGTTCTTGCTGGTGTGAAATGACTGAGTACAAACTGGTGGTGGTTGGAGCAG[G/A]TGGTG TTGGGAAAAGCGCACTGACAATCCAGCTAATCCAGAACCACTTTGTAGATGAATATGATCCCACCATAGAGGT GAGGCCCAGTGGTAGCCCG |
| NRAS-38GA | TTTCCAACAGGTTCTTGCTGGTGTGAAATGACTGAGTACAAACTGGTGGTGGTTGGAGCAGGTG[G/A]TGTTG GGAAAAGCGCACTGACAATCCAGCTAATCCAGAACCACTTTGTAGATGAATATGATCCCACCATAGAGGTGAG GCCCAGTGGTAGCCC |
| TP53-524GA | GGCACCCGCGTCCGCGCCATGGCCATCTACAAGCAGTCACAGCACATGACGGAGGTTGTGAGGC[G/A]CTGC CCCCACCATGAGCGCTGCTCAGATAGCGATGGTGAGCAGCTGGGGCTGGAGAGACGACAGGGCTGGTTGCCCA GGGTCCCCAGGCCTCTGATTCCTCACTGATTGCTCTTAGGTCTGGCC |
| TP53-637CT | CCTCCTCAGCATCTTATCCGAGTGGAAGGAAATTTGCGTGTGGAGTATTTGGATGACAGAAACACTTTT[C/T] GACATAGTGTGGTGGTGCCCTATGAGCCGCCTGAGGTCTGGTTTGCAACTGGGGTCTCTGGGAGGAGGGGTTA AGGGTGGTTGTCAGTGGCCCTC |
| TP53-721TG | CTTGGGCCTGTGTTATCTCCTAGGTTGGCTCTGACTGTACCACCATCCACTACAACTACATGTGTAACAGT[T/ G]CCTGCATGGGCGGCATGAACCGGAGGCCCATCCTCACCATCATCACACTGGAAGACTCCAGGTCAGGAGCCA CTTGCCACCCTGCACACTGGCCTGCTGTGCCCCAGCCTC |
| TP53-733GA | TAGGTTGGCTCTGACTGTACCACCATCCACTACAACTACATGTGTAACAGTTCCTGCATGGGC[G/A]GCATGA ACCGGAGGCCCATCCTCACCATCATCACACTGGAAGACTCCAGGTCAGGAGCCACTTGCCACCCTGCACACTG GCCTGCTGTGCCCCAGCCTC |
| TP53-742CT | CTGACTGTACCACCATCCACTACAACTACATGTGTAACAGTTCCTGCATGGGCGGCATGAAC[C/T]GGAGGCC CATCCTCACCATCATCACACTGGAAGACTCCAGGTCAGGAGCCACTTGCCACCCTGCACACTGGCCTGCTGTGC CCCAGCCTCTGCTTGCCTC |
| TP53-743GA | TGACTGTACCACCATCCACTACAACTACATGTGTAACAGTTCCTGCATGGGCGGCATGAACC[G/A]GAGGCCC ATCCTCACCATCATCACACTGGAAGACTCCAGGTCAGGAGCCACTTGCCACCCTGCACACTGGCCTGCTGTGCC CCAGCCTCTGCTTGCCTC |
| TP53-817CT | CCTCTTGCTTCTCTTTTCCTATCCTGAGTAGTGGTAATCTACTGGGACGGAACAGCTTTGAGGTG[C/T]GTGTTT GTGCCTGTCCTGGGAGAGACCGGCGCACAGAGGAAGAGAATCTCCGCAAGAAAGGGGAGCCTCACCACGAGC TGCCCCCAGGGAGCACTAAGCGAGGTAAGCAA |

Data Analysis:

An automatic baseline and manual threshold of 0.2 were used to calculate the threshold cycle ($C^t$) which is defined as the fractional cycle number at which the fluorescence passes the fixed threshold. PCR reactions were run for a total of 50 cycles. For cast-PCR reactions, there was a pre-run of five cycles at a lower annealing/extension temperature followed by an additional 45 cycles at a higher annealing/extension temperature. The ΔCt between amplification reactions for matched vs. mismatched sequences is defined as the specificity of cast-PCR ($\Delta Ct = Ct_{mismatch} - Ct_{match}$). The larger the ΔCt between mismatched and matched targets, the better assay specificity. The $2^{\Delta Ct}$ value was used to estimate the power of discrimination (or selectivity) which is equal to $\frac{1}{2}^{\Delta Ct}$ or, in some cases, calculated as % ($\frac{1}{2}^{\Delta Ct} \times 100$).

Example 1

Tailed Primers Improve Discrimination of Allelic Variants

The following example demonstrates that the application of allele-specific primers comprising tails significantly improves the discrimination of allelic variants.

In conventional AS-PCR, the discrimination of 3' nucleotide mismatches is largely dependent on the sequence surrounding the SNP and the nature of the allele. The ΔCt between the amplification reactions for matched and mismatched primers varies. To improve the discrimination between the amplification of matched and mismatched sequences, allele-specific primers were designed to comprise tails at their 5' termini and then tested for their suitability in AS-PCR assays.

Assays were performed using the general experimental design and reaction conditions indicated above (with the exception that no blocker probes were included and either tailed or non-tailed allele-specific primers were added), using 0.5 ng/uL genomic DNA containing the hsv11711720 SNP comprising one of three alleles (A, C, or T) as the nucleic acid template (see Table 2A). The three genotypes are indicated in Table 2B. Primers and probes were designed according to the sequences shown in Table 3.

TABLE 2A

Genomic DNA Sequence for hsv11711720 SNP
(SEQ ID NO. 28) (target alleles are
indicated in brackets).

AGAAAATAACTAAGGGAAGGAGGAAAGTGGGGAGGAAGGAAGAACAGTGTGAAG

ACAATGGCCTGAAAACTGAAAAGTCTGTTAAAGTTAATTATCAGTTTTTGAGTCCA

AGAACTGGCTTTGCTACTTTCTGTAAGTTTCTAATTTACTGAATAAGCATGAAAAAG

ATTGCTTTGAGGAATGGTTATAAACACATTCTTAGAGCATAGTAAGCAGTAGGGAGT

AACAAAATAACACTGATTAGAATACTTTACTCTACTTAATTAATCAATCATATTTAG

TTTGACTCACCTTCCCAG[A/C/T]ACCTTCTAGTTCTTTCTTATCTTTCAGTGCTTGTC

CAGACAACATTTTCATTTCAACAACTCCTGCTATTGCAATGATGGGTACAATTGCTA

AGAGTAACAGTGTTAGTTGCCAACCATAGATGAAGGATATAATTATTCCTGTCCCAA

GATTTGCTATATTCTGGGTAATTACAGCAAGCCTGGAACCTATAGCCTGCAAAACAA

AACAAATTAGAGAAATTTTAAAAATATTATCTTCACAACTCATGCTTCTATTTTCTGA

AAACTCACCTTCATGAGACTATATTCATTATTTTAT

TABLE 2B

Genotypes of Genomic DNA Sequence for hsv11711720 SNP

| Genomic DNA ID | Genotype |
|---|---|
| NA17203 | AA |
| NA17129 | CC |
| NA17201 | TT |

TABLE 3

List and Sequences of Primers and Probes
(SEQ ID NOS 29-36, respectively, in
order of appearance) for genomic DNA:
conventional allele-specific primers
("ASP"); tailed allele-specific primers
("tailASP"); locus-specific TaqMan probe
(LST); locus-specific primer (LSP). The
nucleotides shown in lower case are the
tailed portion of the primers. The
nucleotide-specific portion of each
allele-specific primer is at the 3'-most
terminus of each primer (indicated in
bold).

| Primer/Probe ID | Sequence (5' to 3') | Tm (° C.) |
|---|---|---|
| 17129-ASP | ATATTTAGTTTGACTCACCTTCCCAGC | 63.2 |
| 17129-tailASP | accACTCACCTTTCCCAGC | 63.0 |
| 17203-ASP | ATATTTAGTTTGACTCACCTTCCCAGA | 62.0 |
| 17203-tailASP | accACTCACCTTTCCCAGA | 63.7 |
| 17201-ASP | ATATTTAGTTTGACTCACCTTCCCAGT | 62.2 |
| 17201-tailASP | accACTCACCTTTCCCAGT | 64.0 |
| LST | (6-FAM)-TGGACAAGCACTGAAAGA-(MGB) | 67.4 |
| LSP | GCAGGAGTTGTTGAAATGAAAATGTTG | 62.5 |

As shown in Table 4, when using non-tailed ASPs ("ASP-tail"), the discrimination of 3' nucleotide mismatch is largely dependent on the nature of the allele, as a considerable range of ΔCt values is observed depending on the identity of the 3'-terminal base. The range of ΔCt values between matched and mismatched nucleotides ("NT") were from −0.1 to 10. However, with tailed ASPs (ASP+tail), the discrimination of 3' nucleotide mismatch was significantly improved. In fact, as Table 4 shows, the ΔCt value between matched and mismatched nucleotides was consistently equal to or greater than 10 when tailed ASPs were used. The Ct values for amplification of matched sequences using tailed ASPs were comparable to those using conventional or non-tailed ASPs. These results indicate that tailed ASP, can improve the specificity of AS-PCR, but may not improve the sensitivity of detection.

TABLE 4

Tailed allele-specific primers ("ASP") significantly improve discrimination of allelic variants. The specificity ("fold difference") was calculated based on the difference between Ct values using tailed vs. untailed primers ($2^{(\Delta Ct(ASP+tail)-(\Delta Ct(ASP-tail))}$). The mismatched nucleotides of the 3' allele-specific nucleotide portion of the ASPs (+/−tail) and the target allele are also indicated ("NT mismatch").

| NT mismatch | ΔCt (ASP − tail) | ΔCt (ASP + tail) | Specificity Improvement (fold difference) |
|---|---|---|---|
| C-A | 0.9 | 11.5 | 1552.1 |
| C-T | 1.2 | 11.5 | 1278.3 |
| A-C | 10.0 | 11.9 | 3.7 |
| A-G | 9.8 | 11.9 | 4.3 |
| T-G | 2.3 | 11.5 | 588.1 |
| T-C | −0.1 | 11.5 | 3104.2 |
| Average | 4.0 | 11.6 | 1088.5 |

Example 2

Low Primer Concentrations Improve Discrimination of Allelic Variants

Assays were performed using the general experimental design and reaction conditions indicated above, in the presence of 1 million copies of plasmid DNA containing various SNP target sequences (see Table 1) and 200 nM or 800 nM tailed ASP (as indicated). Assay primers and probes were designed according to the sequences shown in FIG. 11A.

The effect of tailed ASP concentration on discrimination of allelic variants is summarized in Table 5. The ΔCt between the amplification reactions for matched and mismatched primers demonstrate that lower tailed ASP concentrations improve discrimination of allelic variants.

TABLE 5

Assay Results Using Different Concentrations of Tailed Allele-specific Primers

| Plasmid SNP ID | ΔCt (ASP @ 800 nM) | ΔCt (ASP @ 200 nM) | Specificity Improvement (fold difference) |
|---|---|---|---|
| CV11201742 | 14.1 | 15.2 | 2.14 |
| CV11349123 | 8.2 | 10 | 3.48 |
| CV1207700 | 5.2 | 6.6 | 2.64 |
| CV25594064 | 20.1 | 19.1 | 0.5 |
| CV25639181 | 11.9 | 12.9 | 2 |
| Average | 12.6 | 13.44 | 2.14 |

Example 3

Primers Designed with Reduced Tms Improves Discrimination of Allelic Variants

Assays were performed using the general experimental design and reaction conditions indicated above, in the presence of 1 million copies of plasmid DNA containing various SNP target sequences (see Table 1) using tailed ASP with a higher Tm (~57° C.) or tailed ASP with a lower Tm (~53° C.). Assay primers and probes were designed according to the sequences shown in FIG. 11B-E (see FIG. 11B for higher Tm ASP and FIG. 11C or lower Tm ASP).

The effect of allele-specific primer Tm on discrimination of allelic variants is summarized in Table 6. The ΔCt of allele-specific primers with a lower Tm are significantly higher than those of allele-specific primers with a higher Tm. Allele-specific primers designed with reduced Tms improved discrimination of allelic variants by as much as 118-fold in some cases or an average of about 13-fold difference.

TABLE 6

ΔCt Values Using Tailed ASPs with Lower Tm (~53° C.) or with Higher Tm (~57° C.)

| Plasmid SNP ID | ΔCt (ASP w/ Tm ~57° C.) | ΔCt (ASP w/ Tm ~53° C.) | Specificity Improvement (fold difference) |
|---|---|---|---|
| BRAF-1799TA | 12.2 | 19.1 | 118.9 |
| CTNNB1-121AG | 11.6 | 14.9 | 10.0 |
| KRAS-176CG | 18.8 | 22.5 | 13.1 |
| NRAS-35GA | 13.0 | 14.0 | 1 |
| TP53-721TG | 14.7 | 19.1 | 20.6 |
| CTNNB1-134CT | 8.6 | 14.1 | 44.8 |
| EGFR-2369CT | 9.7 | 10.7 | 2 |
| KRAS-183AC | 22.2 | 23.1 | 1.8 |
| NRAS-38GA | 14.0 | 14.3 | 1.2 |
| TP53-733GA | 13.6 | 13.5 | 1.0 |
| EGFR-2573TG | 16.7 | 20.2 | 10.9 |
| KRAS-34GA | 14 | 14.8 | 1.8 |
| KRAS-38GA | 11.2 | 14.4 | 8.9 |
| NRAS-181CA | 24.0 | 27.1 | 8.6 |
| TP53-742CT | 9.1 | 8.0 | 0.5 |

TABLE 6-continued

ΔCt Values Using Tailed ASPs with Lower Tm (~53° C.) or with Higher Tm (~57° C.)

| Plasmid SNP ID | ΔCt (ASP w/ Tm ~57° C.) | ΔCt (ASP w/ Tm ~53° C.) | Specificity Improvement (fold difference) |
|---|---|---|---|
| KRAS-35GA | 11.5 | 15.1 | 12.3 |
| NRAS-183AT | 23.6 | 22.7 | 0.5 |
| TP53-524GA | 11.4 | 13.5 | 4.6 |
| TP53-637CT | 11.4 | 14.4 | 7.8 |
| TP53-743GA | 10.1 | 13.2 | 8.4 |
| TP53-817CT | 13.6 | 13.9 | 1.2 |
| Average | 14.1 | 16.3 | 13.3 |

Example 4

Use of Blocker Probes Improves Discrimination of Allelic Variants

The following example illustrates that the use of MGB blocker probes improves the discrimination between 3' nucleotide mismatched and matched primers to target sequences in AS-PCR reactions.

Assays were performed using the general cast-PCR schema and reaction conditions indicated above, using 1 million copies of plasmid DNA containing various SNP target sequences (see Table 1) in the presence of MGB blocker probes or in the absence of MGB blocker probes. Assay primers and probes were designed according to the sequences shown in FIG. 11C-E.

To improve the selectivity of AS-PCR, blocker probes were synthesized to comprise an MGB group at their 3' terminus. (See, for example, Kutyavin, I. V., et al., Nucleic Acids Research, 2000, Vol. 28, No. 2: 655-661, U.S. Pat. Nos. 5,512,677; 5,419,966; 5,696,251; 5,585,481; 5,942,610 and 5,736,626.)

The results of cast-PCR using MGB blocker probes are summarized in Table 7. The ΔCt between cast-PCR with MGB blocker probes is larger than that without MGB blocker probes. As shown, MGB blocker probes improve the discrimination of allelic variants.

TABLE 7

MGB Blocker Probes Improve Discrimination of Allelic Variants

| SNP ID | ΔCt (no MGB blocker) | ΔCt (+MGB blocker) | Specificity Improvement (fold difference) |
|---|---|---|---|
| BRAF-1799TA | 11.4 | 14.9 | 11.5 |
| CTNNB1-121AG | 11.6 | 14.1 | 5.4 |
| KRAS-176CG | 17.8 | 20.9 | 9 |
| NRAS-35GA | 13.9 | 14.3 | 1.4 |
| TP53-721TG | 12.5 | 14.7 | 4.4 |
| CTNNB1-134CT | 6.7 | 10.2 | 11.6 |
| EGFR-2369CT | 7.7 | 10.1 | 5.3 |
| KRAS-183AC | 22.4 | 23 | 1.5 |
| NRAS-38GA | 14.5 | 14.6 | 1.1 |
| TP53-733GA | 13.2 | 14.4 | 2.3 |
| EGFR-2573TG | 18.2 | 21.8 | 11.6 |
| KRAS-34GA | 14.4 | 15.1 | 1.7 |
| KRAS-38GA | 11.9 | 15.1 | 1.7 |
| NRAS-181CA | 19.3 | 24.2 | 30.2 |
| TP53-742CT | 12.7 | 13.6 | 1.9 |
| KRAS-35GA | 11.0 | 13.7 | 6.5 |
| NRAS-183AT | 20.2 | 21.7 | 2.9 |
| TP53-524GA | 13.5 | 13.5 | 1 |
| TP53-637CT | 9.3 | 12.1 | 7.0 |
| TP53-743GA | 9.9 | 11.5 | 3.1 |

TABLE 7-continued

MGB Blocker Probes Improve Discrimination of Allelic Variants

| SNP ID | ΔCt (no MGB blocker) | ΔCt (+MGB blocker) | Specificity Improvement (fold difference) |
|---|---|---|---|
| TP53-817CT | 12.6 | 13.2 | 1.5 |
| Average | 13.6 | 15.5 | 6.0 |

Example 5

Primers Designed to Target Discriminating Bases Improves Discrimination of Allelic Variants Assays were performed using the general cast-PCR schema and reaction conditions indicated above, in the presence of 1 million copies of plasmid DNA containing SNP target sequences (see Table 1). Assay primers and probes were designed according to the sequences shown in FIG. 11C-E.

According to the data summarized in Table 8, the discrimination of cast-PCR was dependent on the nature of the allele being analyzed. As Table 8 indicates, the ΔCt between mismatched and matched sequences for allele-1 were different from ΔCt between mismatched and matched sequences for allele-2. However, both A and G bases, as compared to a T base, were highly discriminating for allele-1 and allele-2 in all four SNPs examined.

TABLE 8

Primers Designed to Target Discriminating Bases Improve Discrimination of Allelic Variants

| | ASP design | | SNP allele-1 | | | SNP allele-2 | |
|---|---|---|---|---|---|---|---|
| SNP ID | 3' NT of ASP1 | 3' NT of ASP2 | Allele NT | ΔCt (Ct_mismatch − Ct_match) | Specificity (fold difference) | Allele NT | ΔCt (Ct_mismatch − Ct_match) | Specificity (fold difference) |
| KRAS-38GA | G | A | C | 13.4 | 10809 | T | 8.2 | 294 |
| NRAS-181CA | C | A | G | 27.5 | 189812531 | T | 9.8 | 891 |
| NRAS-183AT | A | T | T | 17.9 | 244589 | A | 23.4 | 11068835 |
| TP53-742CT | C | T | G | 12.3 | 5043 | A | 8.3 | 315 |

Example 6

Determination of the Sensitivity and Dynamic Range for Cast-PCR

In this example, the sensitivity and dynamic range of cast-PCR was determined by performing cast-PCR using various copy numbers of a target plasmid.

Assays were performed using the general cast-PCR schema and reaction conditions indicated above, using $1\times10^0$ (1 copy) to $1\times10^7$ copies of plasmid DNA containing the NRAS-181CA SNP target sequence (see Table 1). Assay primers and probes were designed according to the sequences shown in FIG. 11C-E.

Figure 5:
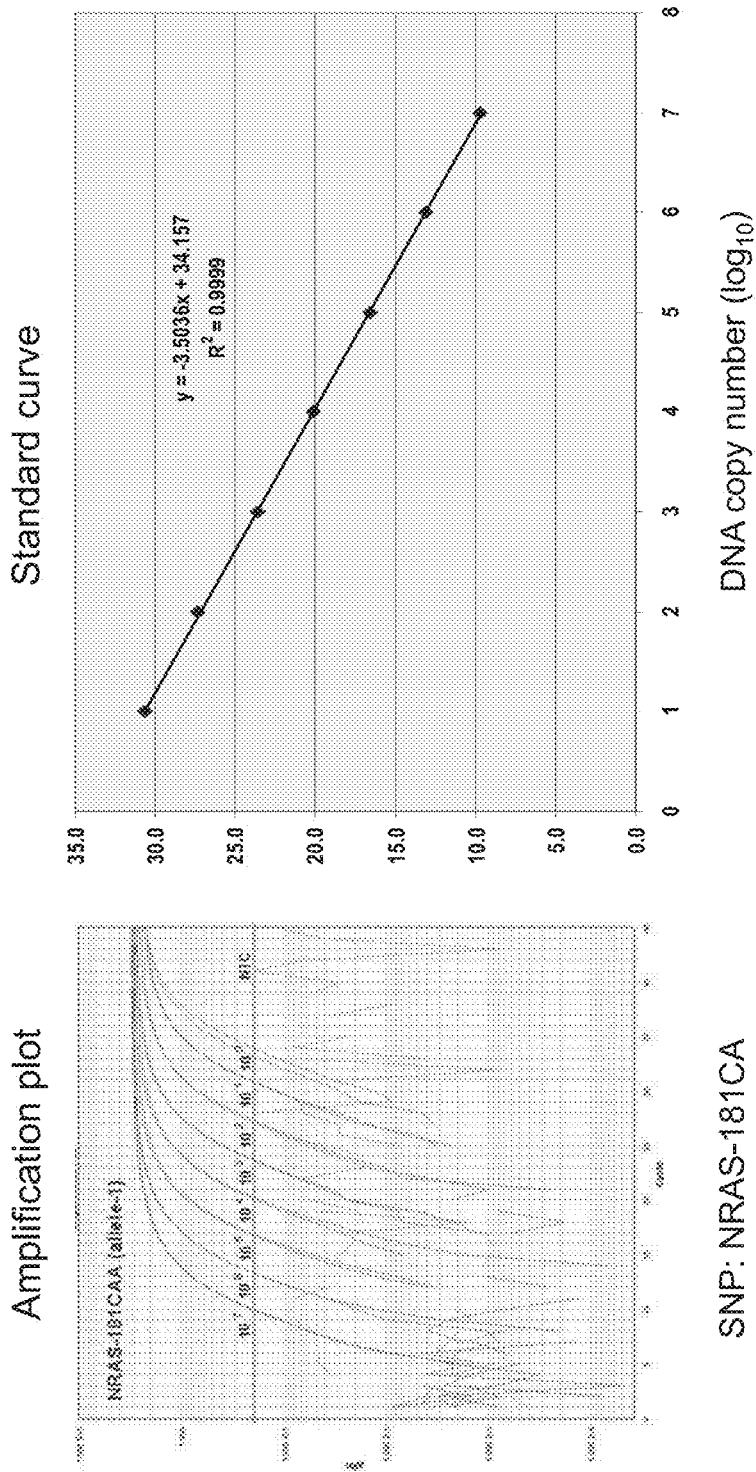
FIG. 5 depicts the TaqMan-like sensitivity and dynamic range of one exemplary embodiment of cast-PCR.

As shown in FIG. 5, the use of tailed primers and MGB-blocker probes does not adversely affect the sensitivity of cast-PCR, as the sensitivity of cast-PCR is comparable to TaqMan assays which do not utilize tailed primers or blocker probes. Furthermore, FIG. 5 shows that the cast-PCR assay shows a linear dynamic range over at least 7 logs.

Example 7

Determination of the Specificity of Cast-PCR

In this example, the specificity of cast-PCR was determined by comparing the amplification of particular alleles of KRAS using either matched or mismatched ASPs to a given allele in the presence of their corresponding blocker probes.

Assays were performed using the general cast-PCR schema and reaction conditions indicated above, using $1\times10^6$ copies of plasmid DNA containing either one of two alleles of the KRAS-183AC SNP target sequence (see Table 1). Assay primers and probes were designed according to the sequences shown in FIG. 11C-E.

The left panel of FIG. 7 shows the an amplification plot of cast-PCR on allele-1 DNA using matched (A1) primers in the presence of A2 blocker probes or mismatched (A2) primers in the presence of A1 blocker probes. The right hand panel shows a similar experiment in which cast-PCR was performed on allele-2 DNA. As indicated in the data summary in FIG. 7, a robust ΔCt values of over 20 were observed for cast-PCR on both alleles of KRAS-183AC tested. This corresponds to a specificity as determined by a calculation of $2^{\Delta Ct}$ of $9\times10^6$, and $2\times10^6$, respectively, for allele-1 and allele-2. Furthermore, a calculation of selectivity ($\frac{1}{2}^{\Delta ct}$) indicates that values of $1/1.1\times10^7$ and $1/5.0\times10^7$ are observed for allele-1 and allele-2, respectively.

Example 8

Cast-PCR is Able to Detect a Single Copy Mutant DNA in One Million Copies of Wild Type DNA In this example, the selectivity of cast-PCR, i.e., the ability of cast-PCR to detect a rare mutant DNA in an excess of wild type DNA, was determined.

Assays were performed using the general cast-PCR schema and reaction conditions indicated above, using various copy numbers of mutant KRAS-183AC plasmid DNA (1 copy to $1\times10^6$ copies) mixed with $1\times10^6$ copies of wild type KRAS-183AC plasmid DNA (see Table 1). Assay primers and probes were designed according to the sequences shown in FIG. 11C-E, and cast-PCR reactions were performed using wild type or mutant allele-specific primers and the corresponding MGB blocker probes.

Figure 8:
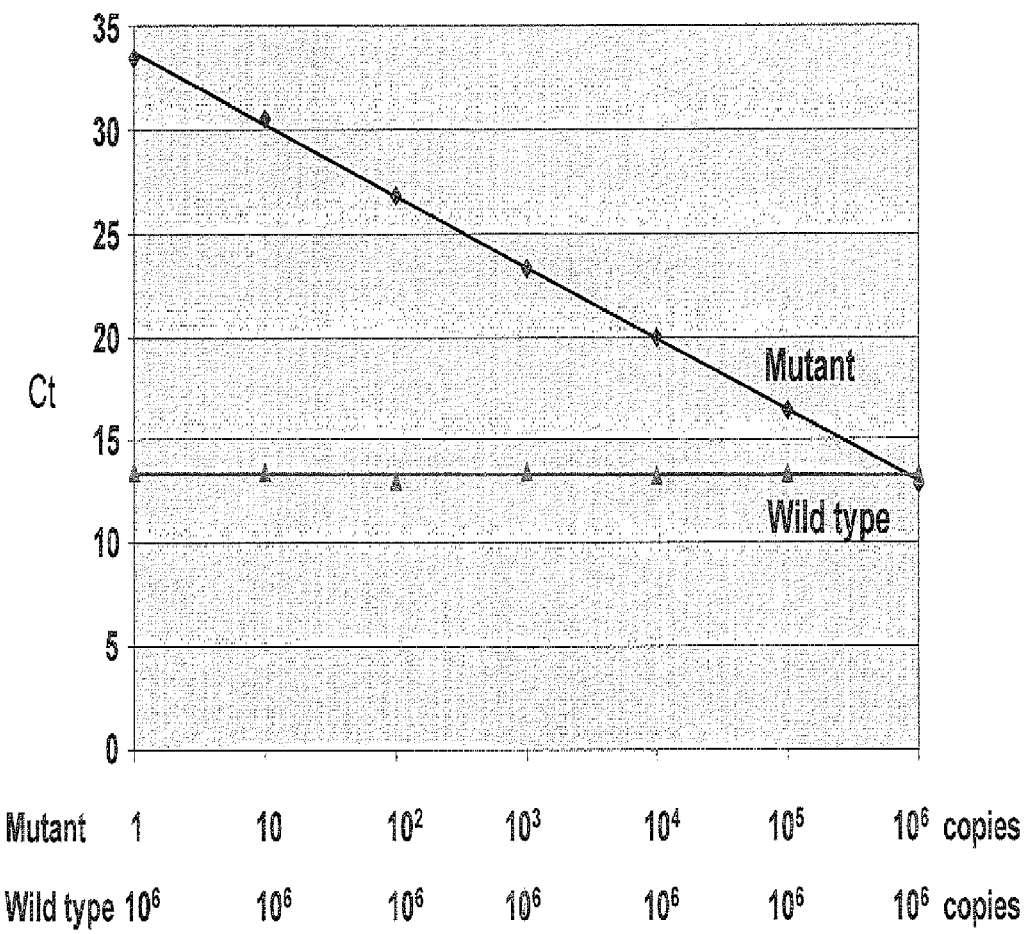
FIG. 8 depicts one exemplary embodiment using cast-PCR methods to detect a single copy of mutant DNA in $10^6$ copies of wild-type DNA.

FIG. 8 shows that cast-PCR is able to detect as little as one copy of a mutant DNA sequence, even when surrounded by a million-fold excess of a wild type sequence.

Example 9

Selectivity of Cast-PCR in Discriminating Tumor Cell DNA from Normal Cell DNA In this example, the selectivity of cast-PCR was determined by performing assays on samples in which various amounts of tumor cell genomic DNA were mixed with or "spiked" into genomic DNA from normal cells. DNA samples were extracted using QIAmp DNA Mini Prep Kits (Qiagen). Wild type DNA was extracted from the SW48 cell line and mutant DNA was extracted the H1573 cell line. The mutant DNA contained the KRAS-G12A mutation (See FIG. 6). The percentage of tumor cell DNA in the spiked samples varied from 0.5 to 100%. cast-PCR was used to detect the presence of tumor cell DNA when present in these percentages.

Assays were performed using the general cast-PCR schema and reaction conditions indicated above, using 30 ng of gDNA per reaction. Assay primers and probes were designed according to the sequences corresponding to KRAS-G12A SNP ID, as shown in FIGS. 18A and 18B.

Figure 9:
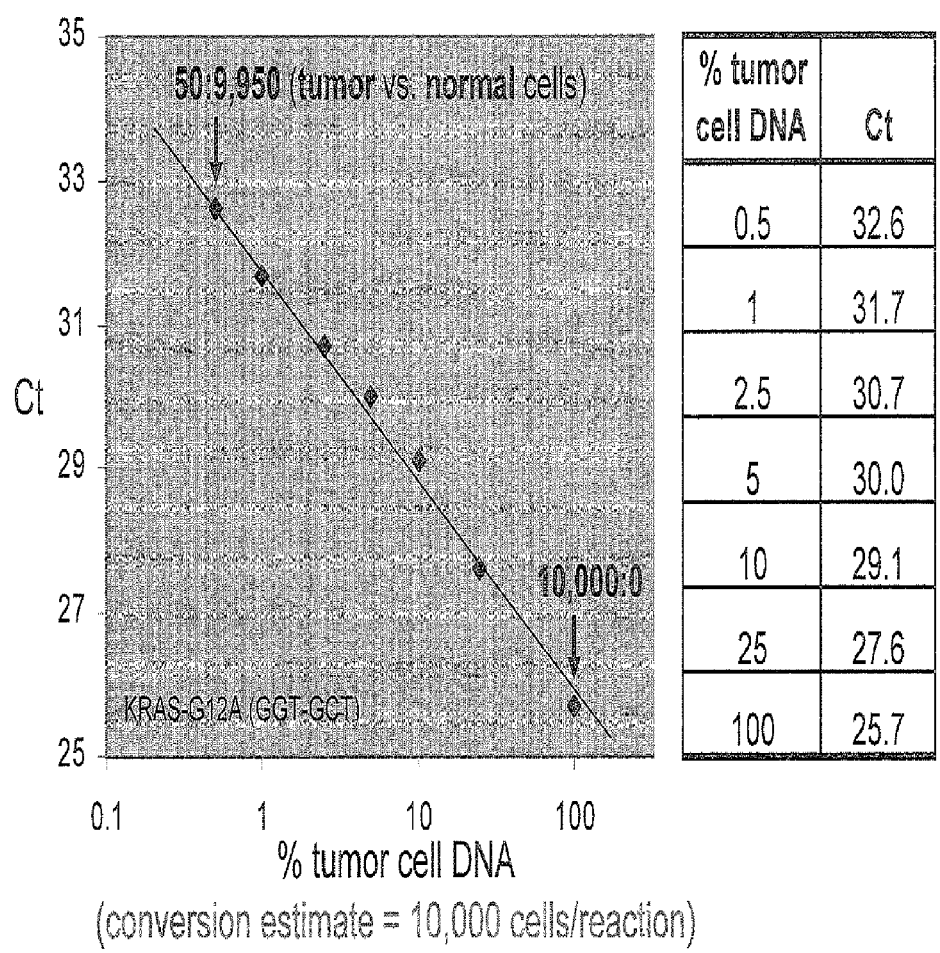
FIG. 9 depicts detection of the relative copy number of mutant samples (KRAS-G12A) spiked in wild type samples using cast-PCR methods.

As shown in FIG. 9, tumor cell DNA, even when present only at a level of 0.5% as compared to normal cell DNA, is easily detected using cast-PCR.

Example 10

Use of Cast-PCR to Detect Tumor Cells in Tumor Samples

In this example, cast-PCR was used to detect and determine the percentage of tumor cells in tumor samples. Various normal and tumor samples were obtained and assayed by cast-PCR for the presence of a number of SNPs associated with cancer as shown in FIG. 10.

Assays were performed using the general cast-PCR schema and reaction conditions indicated above, using 5 ng of gDNA or 1.5 ng cDNA derived from either normal or tumor samples. Assay primers and probes corresponding to the SNPs shown in FIG. 10 were designed according to the sequences as shown in FIG. 11C-E.

The results shown in FIG. 10 indicate that cast-PCR has a low false positive rate as indicated by the failure of cast-PCR to detect the presence of mutant cells in normal samples. In contrast, cast-PCR was able to provide a determination of the percentage of tumor cells in various tumor samples that ranged from just under 2% for a tumor sample containing the NRAS-183AT SNP to greater than 80% for a sample containing the CTNNB1-134CT SNP.

Example 11

Use of Pre-Amplification in Cast-PCR

The following example demonstrates that pre-amplification combined with cast-PCR methods enables detection of multiple alleles from a limited amount of genomic DNA template.

Prior to conducting cast-PCR amplification, multiplex reactions were performed for 7 different KRAS mutations (see Table 9).

10 µl multiplex reactions were prepared in a single tube by combining into one reaction 45 nM of each allele-specific primer (including the allele-1-specific primer and the allele-2-specific primer) and 45 nM of each locus-specific primer for each of the seven different KRAS SNPs, as listed in FIGS. 18A and 18B, 0.1 ng/µL genomic DNA, and 1× Preamp Master Mix (Applied Biosystems, Foster City, Calif.; P/N 437135). The 10 µl pre-amplification reactions were then incubated in an Applied Biosystems 9700 Thermocyler in a 96- or 384-well plate for 95° C. for 10 minutes, followed by 10 cycles of 95° C. for 15 seconds, 60° C. for 4 minutes, and 99.9° C. for 10 minutes, and then held at 4° C. Next, 190 µl of 0.1×TE pH 8.0 was added to each 10 µl pre-amplification reaction (20× dilution). The diluted pre-amplification reaction products were then directly used in subsequent cast-PCR reactions or stored at −20° C. for at least one week prior to use.

TABLE 9

KRAS SNP Sequences (SEQ ID NOS 37-42, respectively, in order of appearance) (target alleles are indicated in brackets).

| SNP ID | SNP Sequence |
| --- | --- |
| KRAS-G12A_GC | TGACTGAATATAAACTTGTGGTAGTTGGAGCTG[G/C]TGGCGTAGGCAAGAGTGCCTTGACGATACAGCTAAT TCAGAATCATTTTGTGGACGAATATGATCCAACAATAGAGGTAAATCTTGTTTTAATATGCATATTACTGGTGC AGGACCATTCTTTGATACA |
| KRAS-G12R_GC | TGACTGAATATAAACTTGTGGTAGTTGGAGCT[G/C]GTGGCGTAGGCAAGAGTGCCTTGACGATACAGCTAAT TCAGAATCATTTTGTGGACGAATATGATCCAACAATAGAGGTAAATCTTGTTTTAATATGCATATTACTGGTGC AGGACCATTCTTTGATACA |
| KRAS-G12D_GA | TGACTGAATATAAACTTGTGGTAGTTGGAGCTG[G/A]TGGCGTAGGCAAGAGTGCCTTGACGATACAGCTAAT TCAGAATCATTTTGTGGACGAATATGATCCAACAATAGAGGTAAATCTTGTTTTAATATGCATATTACTGGTGC AGGACCATTCTTTGATACA |
| KRAS-G12S_GA | TGACTGAATATAAACTTGTGGTAGTTGGAGCT[G/A]GTGGCGTAGGCAAGAGTGCCTTGACGATACAGCTAAT TCAGAATCATTTTGTGGACGAATATGATCCAACAATAGAGGTAAATCTTGTTTTAATATGCATATTACTGGTGC AGGACCATTCTTTGATACA |
| KRAS-G13D_GA | TGACTGAATATAAACTTGTGGTAGTTGGAGCTGGTG[G/A]CGTAGGCAAGAGTGCCTTGACGATACAGCTAAT TCAGAATCATTTTGTGGACGAATATGATCCAACAATAGAGGTAAATCTTGTTTTAATATGCATATTACTGGTGC AGGACCATTCTTTGATACA |
| KRAS-G12C_GT | GTGAGTTTGTATTAAAAGGTACTGGTGGAGTATNNGATAGTGTATTAACCTTATGTGTGACATGTTCTAATATA GTCACATTTTCATTATTTTTATTATAAGGCCTGCTGAAAATGACTGAATATAAACTTGTGGTAGTTGGAGCT[G/ T]GTGGCGTAGGCAAGAGT |

Following pre-amplification, the diluted pre-amplification products were aliquoted into single-plex cast-PCR reactions. Individual assays were performed for each of the 7 different KRAS mutations using the general experimental design and reaction conditions indicated above (see section II of Examples). 10 µL cast-PCR reactions were run for assays containing, as the nucleic acid template, either 1 µL 20× diluted pre-amplification reaction product (as prepared above) or, as a comparison, 0.07 ng genomic DNA. All assay primers and probes were designed according to the sequences shown in FIGS. 18A and 18B.

As shown in FIG. 12, for assays without pre-amplification the average ΔCt of the 7 tested KRAS mutations was 12.0, whereas for assays using pre-amplification the average ΔCt was 17.0. Thus, the ΔΔCt between the two gave about a 5 fold improvement for the pre-amplified reactions over those without pre-amplification.

In an ideal situation (where PCR efficiency=100%), the copy number of the target gene increases about 1000 fold in 10 cycles. Under these conditions, if the starting copy number in a pre-amplification reaction is 0.1 ng/µL (or approximately 33 copies/µL), then after 10 cycles the copy number increases to approximately 33,000 copies/µL. In the example above, the copy number of a 20 fold diluted pre-amplification product is estimated to be approximately 1,650 copies/µL. Therefore, after adding 1 µL of 1,650 copies/µL diluted pre-amplification product into a cast-PCR reaction (final volume of 10 µL), the concentration of the cast-PCR products is approximately 165 copies/µL. Based on this estimation, 10 µL of pre-amplification products from 1 ng/µL genomic DNA can be diluted by as much as 200 fold, and still provide up to 2000 µL of nucleic acid template for use in subsequent cast-PCR reactions.

Example 12

Effect of Tailed ASP on Cast-PCR Specificity

Assays were performed using the general cast-PCR schema and reaction conditions indicated above (see section II of Examples), using 1 million copies of plasmid DNA containing various SNP target sequences (see Table 10). Assay primers and probes were designed according to the sequences shown in FIG. 19A-D. For each SNP analyzed, the blocker probes, locus-specific probes and locus-specific primers were the same and only the allele-specific primers varied (e.g., tailed or non-tailed).

TABLE 10

Plasmid SNP Sequences (SEQ ID NOS 43-78, respectively, in order of appearance) (target alleles are indicated in brackets).

| SNP ID | Sequence |
| --- | --- |
| BRAF-1799TA_TP | ATATTTCTTCATGAAGACCTCACAGTAAAAATAGGTGATTTTGGTCTAGCTACAG[T/A]GAAATCTCGAT GGAGTGGGTCCCATCAGTTTGAACAGTTGTCTGGATCCATTTTG |
| CTNNB1-121AG_TP | GTATCCACATCCTCTTCCTCAGGATTGCCTTTACCACTCAGAGAAGGAGCTGTGG[A/G]AGTGGCACCAG AATGGATTNCAGAGTNCAGGTAAGACTGTTGCTGCCAGTGACTA |
| CTNNB1-134CT_TP | CAGGACTTGGGAGGTATCCACATCCTCTTCCTCAGGATTGCCTTTACCACTCAGA[C/T]AAGGAGCTGTG GTAGTGGCACCAGAATGGATTNCAGAGTNCAGGTAAGACTGTTG |
| EGFR-2369CT_TP | CCCACGTGTGCCGCCTGCTGGGCATCTGCCTCACCTCCACCGTGCAGCTCATCA[C/T]GCAGCTCATGCC CTTCGGCTGCCTCCTGGACTATGTCCGGGAACACAAAGACAATA |
| EGFR-2573TG_TP | TTACTTTGCCTCCTTCTGCATGGTATTCTTTCTCTTCCGCACCCAGCAGTTTGGCC[T/G]GCCCAAAATCT GTGATCTTGACATGCTGCGGTGTTTTCACCAGTACGTTCCTGG |
| KRAS-176CG_TP | AGGAAGCAAGTAGTAATTGATGGAGAAACCTGTCTCTTGGATATTCTCGACACAG[C/G]AGGTCANGAG GAGTACAGTGCAATGAGGGACCAGTACATGAGGACTGGGGAGGGC |
| KRAS-183AC_TP | AAGTAGTAATTGATGGAGAAACCTGTCTCTTGGATATTCTCGACACAGCAGGTCA[A/C]GAGGAGTACA GTGCAATGAGGGACCAGTACATGAGGACTGGGGAGGGCTTTCTTT |
| KRAS-34GA_TP | CCACAAAATGATTCTGAATTAGCTGTATCGTCAAGGCACTCTTGCCTACGCCAC[G/A]AGCTCCAACTAC CACAAGTTTATATTCAGTCATTTTCAGCAGGCCTTATAATAAAA |
| KRAS-35GA_TP | TCCACAAAATGATTCTGAATTAGCTGTATCGTCAAGGCACTCTTGCCTACGCCA[G/A]CAGCTCCAACTA CCACAAGTTTATATTCAGTCATTTTCAGCAGGCCTTATAATAAA |
| KRAS-3GA_TP | ATTATAAGGCCTGCTGAAAATGACTGAATATAAACTTGTGGTAGTTGGAGCTGGTG[G/A]CGTAGGCAA GAGTGCCTTGACGATACAGCTAATTCAGAATCATTTTGTGGACGA |
| NRAS-181CA_TP | AACAAGTGGTTATAGATGGTGAAACCTGTTTGTTGGACATACTGGATACAGCTGGA[C/A]AAGAAGAGT ACAGTGCCATGAGAGACCAATACATGAGGACAGGCGAAGGCTTCC |
| NRAS-183AT_TP | CAAGTGGTTATAGATGGTGAAACCTGTTTGTTGGACATACTGGATACAGCTGGACA[A/T]GAAGAGTAC AGTGCCATGAGAGACCAATACATGAGGACAGGCGAAGGCTTCCTC |
| BRAF-1799TA_TP | ATATTTCTTCATGAAGACCTCACAGTAAAAATAGGTGATTTTGGTCTAGCTACAG[T/A]GAAATCTCGAT GGAGTGGGTCCCATCAGTTTGAACAGTTGTCTGGATCCATTTTG |
| CTNNB1-121AG_TP | GTATCCACATCCTCTTCCTCAGGATTGCCTTTACCACTCAGAGAAGGAGCTGTGG[A/G]AGTGGCACCAG AATGGATTNCAGAGTNCAGGTAAGACTGTTGCTGCCAGTGACTA |
| CTNNB1-134CT_TP | CAGGACTTGGGAGGTATCCACATCCTCTTCCTCAGGATTGCCTTTACCACTCAGA[C/T]AAGGAGCTGTG GTAGTGGCACCAGAATGGATTNCAGAGTNCAGGTAAGACTGTTG |
| EGFR-2369CT_TP | CCCACGTGTGCCGCCTGCTGGGCATCTGCCTCACCTCCACCGTGCAGCTCATCA[C/T]GCAGCTCATGCC CTTCGGCTGCCTCCTGGACTATGTCCGGGAACACAAAGACAATA |

TABLE 10-continued

Plasmid SNP Sequences (SEQ ID NOS 43-78, respectively, in order of appearance) (target alleles are indicated in brackets).

| SNP ID | Sequence |
|---|---|
| EGFR-2573TG_TP | TTACTTTGCCTCCTTCTGCATGGTATTCTTTCTCTTCCGCACCCAGCAGTTTGGCC[T/G]GCCCAAAATCT GTGATCTTGACATGCTGCGGTGTTTTCACCAGTACGTTCCTGG |
| KRAS-176CG_TP | AGGAAGCAAGTAGTAATTGATGGAGAAACCTGTCTCTTGGATATTCTCGACACAG[C/G]AGGTCANGAG GAGTACAGTGCAATGAGGGACCAGTACATGAGGACTGGGGAGGGC |
| KRAS-183AC_TP | AAGTAGTAATTGATGGAGAAACCTGTCTCTTGGATATTCTCGACACAGCAGGTCA[C/G]GAGGAGTACA GTGCAATGAGGGACCAGTACATGAGGACTGGGGAGGGCTTTCTTT |
| KRAS-34GA_TP | CCACAAAATGATTCTGAATTAGCTGTATCGTCAAGGCACTCTTGCCTACGCCAC[G/A]AGCTCCAACTAC CACAAGTTTATATTCAGTCATTTTCAGCAGGCCTTATAATAAAA |
| KRAS-35GA_TP | TCCACAAAATGATTCTGAATTAGCTGTATCGTCAAGGCACTCTTGCCTACGCCA[G/A]CAGCTCCAACTA CCACAAGTTTATATTCAGTCATTTTCAGCAGGCCTTATAATAAA |
| KRAS-3GA_TP | ATTATAAGGCCTGCTGAAAATGACTGAATATAAACTTGTGGTAGTTGGAGCTGGTG[G/A]CGTAGGCAA GAGTGCCTTGACGATACAGCTAATTCAGAATCATTTTGTGGACGA |
| NRAS-181CA_TP | AACAAGTGGTTATAGATGGTGAAACCTGTTTGTTGGACATACTGGATACAGCTGGA[C/A]AAGAAGAGT ACAGTGCCATGAGAGACCAATACATGAGGACAGGCGAAGGCTTCC |
| NRAS-183AT_TP | CAAGTGGTTATAGATGGTGAAACCTGTTTGTTGGACATACTGGATACAGCTGGACA[A/T]GAAGAGTAC AGTGCCATGAGAGACCAATACATGAGGACAGGCGAAGGCTTCCTC |
| BRAF-1799TA_TP | ATATTTCTTCATGAAGACCTCACAGTAAAAATAGGTGATTTTGGTCTAGCTACAG[T/A]GAAATCTCGAT GGAGTGGGTCCCATCAGTTTGAACAGTTGTCTGGATCCATTTTG |
| CTNNB1-121AG_TP | GTATCCACATCCTCTTCCTCAGGATTGCCTTTACCACTCAGAGAAGGAGCTGTGG[A/G]AGTGGCACCAG AATGGATTNCAGAGTNCAGGTAAGACTGTTGCTGCCAGTGACTA |
| CTNNB1-134CT_TP | CAGGACTTGGGAGGTATCCACATCCTCTTCCTCAGGATTGCCTTTACCACTCAGA[C/T]AAGGAGCTGTG GTAGTGGCACCAGAATGGATTNCAGAGTNCAGGTAAGACTGTTG |
| EGFR-2369CT_TP | CCCACGTGTGCCGCCTGCTGGGCATCTGCCTCACCTCCACCGTGCAGCTCATCA[C/T]GCAGCTCATGCC CTTCGGCTGCCTCCTGGACTATGTCCGGGAACACAAAGACAATA |
| EGFR-2573TG_TP | TTACTTTGCCTCCTTCTGCATGGTATTCTTTCTCTTCCGCACCCAGCAGTTTGGCC[C/T]GCCCAAAATCT GTGATCTTGACATGCTGCGGTGTTTTCACCAGTACGTTCCTGG |
| KRAS-176CG_TP | AGGAAGCAAGTAGTAATTGATGGAGAAACCTGTCTCTTGGATATTCTCGACACAG[T/G]AGGTCANGAG GAGTACAGTGCAATGAGGGACCAGTACATGAGGACTGGGGAGGGC |
| KRAS-183AC_TP | AAGTAGTAATTGATGGAGAAACCTGTCTCTTGGATATTCTCGACACAGCAGGTCA[A/C]GAGGAGTACA GTGCAATGAGGGACCAGTACATGAGGACTGGGGAGGGCTTTCTTT |
| KRAS-34GA_TP | CCACAAAATGATTCTGAATTAGCTGTATCGTCAAGGCACTCTTGCCTACGCCAC[G/A]AGCTCCAACTAC CACAAGTTTATATTCAGTCATTTTCAGCAGGCCTTATAATAAAA |
| KRAS-35GA_TP | TCCACAAAATGATTCTGAATTAGCTGTATCGTCAAGGCACTCTTGCCTACGCCA[G/A]CAGCTCCAACTA CCACAAGTTTATATTCAGTCATTTTCAGCAGGCCTTATAATAAA |
| KRAS-3GA_TP | ATTATAAGGCCTGCTGAAAATGACTGAATATAAACTTGTGGTAGTTGGAGCTGGTG[G/A]CGTAGGCAA GAGTGCCTTGACGATACAGCTAATTCAGAATCATTTTGTGGACGA |
| NRAS-181CA_TP | AACAAGTGGTTATAGATGGTGAAACCTGTTTGTTGGACATACTGGATACAGCTGGA[C/A]AAGAAGAGT ACAGTGCCATGAGAGACCAATACATGAGGACAGGCGAAGGCTTCC |
| NRAS-183AT_TP | CAAGTGGTTATAGATGGTGAAACCTGTTTGTTGGACATACTGGATACAGCTGGACA[A/T]GAAGAGTAC AGTGCCATGAGAGACCAATACATGAGGACAGGCGAAGGCTTCCTC |

The results of cast-PCR using non-tailed ASP and cast-PCR using tailed-ASP are summarized in FIG. 13. In the cast-PCR reactions having no tailed primers, the average ΔCt of the 12 tested mutations was 10.3, whereas in the cast-PCR reactions with tailed primers the average ΔCt of 12 tested assays is 16.3. Thus, the average ΔΔCt between cast-PCR comprising tailed ASP versus cast-PCR comprising non-tailed ASP was about 6.0, which is about a 64 fold improvement in specificity for reactions comprising ASP+ tail primers.

Example 13

Comparison of Cast-PCR and ASB-PCR

Allelic discrimination for assays using cast-PCR methods was compared to assays using other Allele-Specific PCR with a Blocking reagent (ASB-PCR) methods (see, e.g., Morlan et al., 2009).

cast-PCR assays were performed using the general schema and reaction conditions indicated above, using 1 million copies of plasmid DNA containing various SNP target sequences (see Table 10). Assays were performed using the general experimental design and reaction conditions indicated above (see section II of Examples). Assay primers and probes were designed according to the sequences shown in FIG. 19B-D.

ASB-PCR assays were performed using 1 million copies of plasmid DNA containing various SNP target sequences (see Table 10), 900 nM non-tailed allele-specific primers (Tm 58~62° C.), 3600 nM allele-specific phosphate blocker (Tm 58~62° C.), 200 nM locus-specific TaqMan probe (Tm 70~74° C.), and 900 nM locus-specific primers (Tm 60~63° C.).

ASB-PCR assay primers and probes were designed according to the sequences shown in FIG. 20A-C. The ASB-PCR reactions were incubated in a 384-well plate at 95° C. for 10 minutes, followed by 50 cycles of at 92° C. for 20 seconds, 60° C. for 45 seconds. All reactions were run in 4 replications in an ABI PRISM 7900HT® Sequence Detection System, according to the manufacturer's instructions.

The results for this example are summarized in FIG. 14. In the ASB-PCR assays, the average ΔCt of 12 different mutations was 14.1. In cast-PCR assays, the average ΔCt of the same 12 mutations was 16.3. The ΔΔCt between ASB-PCR and cast-PCR was 2.2, which indicates that the specificity of cast-PCR was approximately 4.6 fold higher than that of the ASB-PCR assay.

Example 14

Comparison of MGB and Phosphate Blocker Probes in Cast-PCR

The use of MGB blocker probes was compared to the use of other types of blocker probes, such as $PO_4$ blocker probes (e.g., Morlan et al., 2009), in cast-PCR assays.

All assays were performed using the general cast-PCR schema and reaction conditions indicated above (see Section II in Examples), using 1 million copies of plasmid DNA containing various SNP target sequences (see Table 10), except that reactions contained either 150 nm allele-specific MGB blocker probes or 150 nm allele-specific 3'-phosphate blocker probes. Assay primers and probes were designed according to the sequences shown in FIG. 19B-D (for cast-PCR using MGB blocker probes) or FIGS. 19B-C and FIG. 20C (for cast-PCR using phosphate blocker probes; "PHOS1" to block allele-1 and "PHOS2" to block allele-2).

The results of assays with phosphate blocker probes or with MGB blocker probes are summarized in FIG. 15. In cast-PCR assays performed using phosphate blocker probes the average ΔCt of 12 different mutations was 15.1. In comparison, the average ΔCt for the same 12 mutations using cast-PCR assays performed with MGB blocker probes was slightly higher and gave a ΔCt of 15.8.

Example 15

Improving the Specificity of Cast-PCR Using LNA Modified ASP

LNA-modified cast-PCR assays were performed using the general experimental design and reaction conditions indicated above (see Section II in Examples), using 0.5 ng/μL of genomic DNA. Assay primers and probes were designed according to the sequences shown in FIGS. 21A-C. For each SNP analyzed, the blocker probes, locus-specific probes and locus-specific primers were the same and only the allele-specific primers varied (i.e., with or without an LNA-modification at the 3'end).

The effect of LNA modification of the ASP on the specificity of cast-PCR is summarized in FIG. 16. For the 12 cast-PCR assays performed using LNA-modified allele-specific primers, the average ΔCt was 16.3. In comparison, the average ΔCt for the same 12 mutations using cast-PCR assays performed allele-specific primers having no modifications the ΔCt was noticeably higher at 18.5. Based on the ΔΔCt the assay specificity increased by approximately 4 fold for those assays that used LNA-modified allele-specific primers.

Example 16

Improving the Specificity of Cast-PCR Using Other Modified ASP cast-PCR assays using other chemically-modified ASPs were performed using the general experimental design and reaction conditions indicated above conditions indicated above (see Section II in Examples), performed in the presence of 1 million copies of plasmid DNA containing various SNP target sequences (see Table 10). Assay primers and probes were designed according to the sequences shown in FIG. 22. For each SNP analyzed, the blocker probes, locus-specific probes and locus-specific primers were the same and only the allele-specific primers varied (i.e., with or without chemical modifications, i.e., ppA, ppG, iso dC or fdU, at the 3'end).

The results of cast-PCR assays using unmodified ASP and cast-PCR assays with modified ASP are summarized in FIG. 17. As shown, allele-specific primers having pyrophosphate modifications (ppA or ppG) at their 3'-ends increased ΔCt by 2-3, which is approximately a 4-6 fold increase in assay specificity.

It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

All references cited herein, including patents, patent applications, papers, text books, and the like, and the references cited therein, to the extent that they are not already, are hereby incorporated by reference in their entirety. In the event that one or more of the incorporated literature and similar materials differs.

We claim:

1. A method for detecting a first allelic variant of a target sequence in a nucleic acid sample suspected of comprising at least a second allelic variant of the target sequence, comprising:
   a) forming a first reaction mixture by combining:
      i) the nucleic acid sample;
      ii) a first allele-specific primer, wherein an allele-specific nucleotide portion of the first allele-specific primer is complementary to the first allelic variant of the target sequence, and wherein the melting temperature Tm of the first allele-specific primer ranges from about 50° C. to 67° C.;
      iii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a non-extendable blocker moiety, wherein the non-extendable blocker moiety comprises a minor groove binder (MGB);
      iv) a first locus-specific primer that is complementary to a region of the target sequence that is 3' from the first allelic variant and on the opposite strand; and
      v) a first detector probe;
   b) carrying out an amplification reaction on the first reaction mixture using the first locus-specific primer and the first allele-specific primer to form a first amplicon; and
   c) detecting the first amplicon by detecting a change in a detectable property of the first detector probe, thereby detecting the first allelic variant of the target gene in the nucleic acid sample,
   wherein the selectivity is at a level whereby a single copy of a given allele in about 1 million copies of another allele or alleles can be detected.

2. The method of claim 1, further comprising using the change in a detectable property of the first detector probe to quantitate the first allelic variant.

3. The method of claim 1, further comprising:
   d) forming a second reaction mixture by combining:
      i) the nucleic acid sample;
      ii) a second allele-specific primer, wherein an allele-specific nucleotide portion of the second allele-specific primer is complementary to the second allelic variant of the target sequence, and wherein the melting temperature Tm of the first allele-specific primer ranges from about 50° C. to 67° C.;
      iii) a second allele-specific blocker probe that is complementary to a region of the target sequence comprising the first allelic variant, wherein said region encompasses a position corresponding to the binding position of the allele-specific nucleotide portion of the second allele-specific primer, and wherein the second allele-specific blocker probe comprises a non-extendable blocker moiety;
      iv) a second locus-specific primer that is complementary to a region of the target sequence that is 3' from the second allelic variant and on the opposite strand; and
      v) a second detector probe;

e) carrying out an amplification reaction on the second reaction mixture using the second allele-specific primer and the locus-specific primer, to form a second amplicon; and f) detecting the second amplicon by detecting a change in a detectable property of the detector probe, thereby detecting the second allelic variant of the target gene in the nucleic acid sample.

4. The method of claim 3, further comprising comparing the change in a detectable property of the first detector probe in the first reaction mixture to the change in a detectable property of the second detector probe in the second reaction mixture.

5. The method of claim 3, wherein said first, second or first and second allele-specific primer and/or said first, second, or first and second allele-specific blocker probe comprises at least one modified base.

6. The method of claim 5, wherein said modified base is selected from an 8-aza-7-deaza-dN (ppN) base analog, where N is adenine (A), cytosine (C), guanine (G), or thymine (T); a locked nucleic acid (LNA) base; a fdU; and an iso dC base.

7. The method of claim 5, wherein said modified base is any modified base that increases the Tm between matched and mismatched target sequences or nucleotides.

8. The method of claim 5, wherein said modified base is located at (a) the 3'-end, (b) the 5'-end, (c) at an internal position or at any combination of (a), (b) or (c) within said allele-specific primer and/or allele-specific blocker probe.

9. The method of claim 3, wherein said first, second or first and second allele-specific primer has a tail at the 5' end.

10. The method of claim 9, wherein the tail of the said first, second or first and second allele-specific primer is GC rich.

11. The method of claim 1, wherein the MGB is located at the 3'-end, the 5'-end and/or at an internal position within said allele-specific blocker probe.

12. The method of claim 1, wherein the allele-specific blocker probe is not cleaved during PCR amplification.

13. The method of claim 1, wherein the allele-specific blocker probe has a Tm that ranges from about 58° C. to 66° C.

14. The method of claim 3, wherein the first, second or first and second allele-specific primer concentration is between about 50-400 nM.

15. The method of claim 3, wherein the first, or second or first and second allele-specific primer concentration is between about 100-300 nM.

16. The method of claim 3, wherein the Tm of the allele-specific primers is about 3° C. to 6° C. higher than the anneal/extend temperature of the PCR cycling conditions employed during amplification.

17. The method of claim 3, wherein said carrying out an amplification reaction comprises a 2-stage cycling protocol comprising a first stage of amplification that employs an initial number of cycles at a lower annealing/extension temperature, followed by a second stage of amplification that employs a number of cycles at a higher annealing/extension temperature.

18. The method of claim 1, wherein the annealing/extension temperature used during the first cycling stage of the 2-stage cycling protocol is between 1-3° C. lower than the annealing/extension temperature used during the second stage.

19. The method of claim 1, wherein the annealing/extension temperature used during the first cycling stage of the 2-stage cycling protocol is between 56-59° C. and the annealing/extension temperature used during the second stage is between 60-62° C.

20. The method of claim 1, wherein the detector probe is a 5' nuclease probe.

21. The method of claim 1, wherein the detector probe can comprises an MGB moiety, a reporter moiety, a quencher moiety, and/or a passive reference.

* * * * *